(12) United States Patent
Pelrine et al.

(10) Patent No.: US 7,064,472 B2
(45) Date of Patent: Jun. 20, 2006

(54) ELECTROACTIVE POLYMER DEVICES FOR MOVING FLUID

(75) Inventors: Ronald E. Pelrine, Boulder, CO (US); Roy David Kornbluh, Palo Alto, CA (US); Scott E. Stanford, Palo Alto, CA (US); Qibing Pei, Fremont, CA (US); Richard Heydt, Palo Alto, CA (US); Joseph S. Eckerle, Redwood City, CA (US); Jonathan R. Heim, Pacifica, CA (US)

(73) Assignee: SRI International, Menlo Park, CA (US)

( * ) Notice: Subject to any disclaimer, the term of this patent is extended or adjusted under 35 U.S.C. 154(b) by 204 days.

(21) Appl. No.: 10/393,506

(22) Filed: Mar. 18, 2003

(65) Prior Publication Data

US 2004/0008853 A1    Jan. 15, 2004

Related U.S. Application Data

(63) Continuation-in-part of application No. 10/154,449, filed on May 21, 2002, now Pat. No. 6,891,317, and a continuation-in-part of application No. 10/090,430, filed on Feb. 28, 2002, now Pat. No. 6,806,621, and a continuation-in-part of application No. 10/066,407, filed on Jan. 31, 2002, and a continuation-in-part of application No. 10/053,511, filed on Jan. 16, 2002, now Pat. No. 6,882,086, and a continuation-in-part of application No. 10/007,705, filed on Dec. 6, 2001, now Pat. No. 6,809,462, and a continuation-in-part of application No. 09/828,496, filed on Apr. 4, 2001, now Pat. No. 6,586,859, and a continuation-in-part of application No. 09/792,431, filed on Feb. 23, 2001, now Pat. No. 6,628,040, and a continuation-in-part of application No. 09/779,203, filed on Feb. 7, 2001, now Pat. No. 6,664,718, and a continuation-in-part of application No. 09/619,847, filed on Jul. 20, 2000, now Pat. No. 6,812,624.

(60) Provisional application No. 60/365,472, filed on Mar. 18, 2002, provisional application No. 60/327,846, filed on Oct. 5, 2001, provisional application No. 60/293,003, filed on May 22, 2001, provisional application No. 60/293,004, filed on May 22, 2001, provisional application No. 60/293,005, filed on May 22, 2001, provisional application No. 60/273,108, filed on Mar. 2, 2001, provisional application No. 60/194,817, filed on Apr. 5, 2000, provisional application No. 60/192,237, filed on Mar. 27, 2000, provisional application No. 60/190,713, filed on Mar. 17, 2000, provisional application No. 60/187,809, filed on Mar. 8, 2000, provisional application No. 60/184,217, filed on Feb. 23, 2000, provisional application No. 60/181,404, filed on Feb. 9, 2000, provisional application No. 60/161,325, filed on Oct. 25, 1999, provisional application No. 60/153,329, filed on Sep. 10, 1999, provisional application No. 60/144,556, filed on Jul. 20, 1999.

(51) Int. Cl.
*F04B 45/02* (2006.01)
*H01L 41/08* (2006.01)

(52) U.S. Cl. .................. 310/324; 417/472; 417/474

(58) Field of Classification Search ................ 310/324, 310/337; 417/472, 474
See application file for complete search history.

(56) References Cited

U.S. PATENT DOCUMENTS

| | | | | |
|---|---|---|---|---|
| 2,430,013 | A * | 11/1947 | Hansell | ...................... 367/152 |
| 3,050,034 | A | 8/1962 | Benton | |
| 3,303,750 | A * | 2/1967 | Powell | ........................ 91/273 |
| 3,403,234 | A | 9/1968 | Barnes, Jr. | |
| 3,832,580 | A | 8/1974 | Yamamuro et al. | |
| 4,283,461 | A * | 8/1981 | Wooden et al. | ............. 428/422 |
| 4,284,921 | A | 8/1981 | Lemonon et al. | ........... 310/328 |
| 4,290,983 | A | 9/1981 | Sasaki et al. | ................ 264/435 |
| 4,297,394 | A * | 10/1981 | Wooden et al. | ............. 427/100 |
| 4,342,936 | A | 8/1982 | Marcus et al. | .............. 310/330 |
| 4,344,743 | A * | 8/1982 | Bessman et al. | ............ 417/317 |
| 4,384,394 | A | 5/1983 | Lemonon et al. | |
| 4,400,634 | A | 8/1983 | Micheron | |
| 4,401,911 | A | 8/1983 | Ravinet et al. | |
| 4,442,372 | A | 4/1984 | Roberts | |
| 4,518,555 | A | 5/1985 | Ravinet et al. | |
| 4,588,998 | A * | 5/1986 | Yamamuro et al. | ........... 347/68 |

| | | | |
|---|---|---|---|
| 4,733,121 A | 3/1988 | Herbert | |
| 4,843,275 A | 6/1989 | Radice | |
| 4,877,988 A | 10/1989 | McGinniss et al. | |
| 4,885,783 A | 12/1989 | Whitehead et al. | |
| 4,969,197 A | 11/1990 | Takaya | |
| 5,024,872 A | 6/1991 | Wilson et al. | |
| 5,119,840 A * | 6/1992 | Shibata | 134/184 |
| 5,229,979 A | 7/1993 | Scheinbeim et al. | |
| 5,250,784 A | 10/1993 | Muller et al. | |
| 5,254,296 A | 10/1993 | Perlman | |
| 5,356,500 A | 10/1994 | Scheinbeim et al. | |
| 5,430,565 A | 7/1995 | Yamanouchi et al. | |
| 5,440,194 A | 8/1995 | Beurrier | |
| 5,481,152 A | 1/1996 | Buschulte | 310/328 |
| 5,509,888 A | 4/1996 | Miller | 600/29 |
| 5,642,015 A | 6/1997 | Whitehead et al. | |
| 5,682,075 A | 10/1997 | Bolleman et al. | |
| 5,751,090 A | 5/1998 | Henderson | 310/328 |
| 5,835,453 A | 11/1998 | Wynne et al. | |
| 5,902,836 A | 5/1999 | Bennet et al. | |
| 5,915,377 A | 6/1999 | Coffee | |
| 5,933,170 A | 8/1999 | Takeuchi et al. | 347/71 |
| 5,977,685 A | 11/1999 | Kurita et al. | |
| 6,048,622 A | 4/2000 | Hagood et al. | |
| 6,060,811 A | 5/2000 | Fox et al. | |
| 6,084,321 A | 7/2000 | Hunter et al. | |
| 6,093,995 A | 7/2000 | Lazarus et al. | 310/328 |
| 6,184,608 B1 | 2/2001 | Cabuz et al. | |
| 6,184,609 B1 | 2/2001 | Johansson et al. | |
| 6,198,203 B1 * | 3/2001 | Hotomi | 310/324 |
| 6,249,076 B1 | 6/2001 | Madden et al. | |
| 6,255,758 B1 | 7/2001 | Cabuz et al. | |
| 6,321,428 B1 * | 11/2001 | Toda et al. | 29/25.35 |
| 6,343,129 B1 | 1/2002 | Pelrine et al. | 381/194 |
| 6,376,971 B1 | 4/2002 | Pelrine et al. | |
| 6,385,021 B1 | 5/2002 | Takeda et al. | |
| 6,411,013 B1 | 6/2002 | Horning | |
| 6,435,840 B1 | 8/2002 | Sharma et al. | 417/322 |
| 6,543,110 B1 | 4/2003 | Pelrine et al. | |
| 6,545,384 B1 | 4/2003 | Pelrine et al. | |
| 6,617,765 B1 * | 9/2003 | Lagier et al. | 310/330 |
| 6,664,718 B1 | 12/2003 | Pelrine et al. | |
| 6,720,710 B1 * | 4/2004 | Wenzel et al. | 310/328 |

FOREIGN PATENT DOCUMENTS

| | | | | |
|---|---|---|---|---|
| DE | 199 52 062 A1 | | 10/1999 | |
| EP | 59-126689 | | 7/1984 | |
| EP | 7-111785 | | 4/1995 | |
| JP | 4-353279 | * | 12/1992 | 417/474 |
| JP | 5-202707 | * | 8/1993 | 123/188.1 |
| JP | 2001-286162 | * | 10/2001 | |
| WO | WO 87/07218 | * | 12/1987 | |
| WO | WO 89/02658 | | 3/1989 | |
| WO | WO 94/18433 | | 8/1994 | |
| WO | WO 95/08905 | | 3/1995 | |
| WO | WO 97/15876 | | 5/1997 | |
| WO | WO 98/35529 | | 8/1998 | |
| WO | WO 99/17929 | | 4/1999 | |
| WO | WO 99/23749 | | 5/1999 | |
| WO | WO 01/06575 | | 1/2001 | |

OTHER PUBLICATIONS

Ajluni, Cheryl, "Pressure Sensors Strive to Stay on Top, New Silicon Micromatchining Techniques and Designs Promise Higher Performance", *Electronic Design—Advanced Technology Series*, Oct. 3, 1994, pp. 67-74.

Anderson, R. A., "Mechanical Stress in a Dielectric Solid From a Uniform Electric Field", *The American Physical Society*, 1986, pp. 1302-1307.

Aramaki, S., S. Kaneko, K. Arai, Y. Takahashi, H. Adachi, and K. Yanagisawa. 1995. "Tube Type Micro Manipulator Using Shape Memory Alloy (SMA)," *Proceedings of the IEEE Sixth International Symposium on Micro Machine and Human Science*, Nagoya, Japan, pp. 115-120.

Ashley, S., "Smart Skis and Other Adaptive Structures", *Mechanical Engineering*, Nov. 1995, pp. 77-81.

Bar-Cohen, Yoseph, JPL, *WorldWide ElectroActive Polymers, EAP (Artificial Muscles) Newsletter*, vol. 1, No. 1, Jun. 1999.

Bar-Cohen, Yoseph, JPL, *WorldWide ElectroActive Polymers, EAP (Artificial Muscles) Newsletter*, vol. 1, No. 2, Dec. 1999.

Bar-Cohen, Yoseph, JPL, *WorldWide ElectroActive Polymers, EAP (Artificial Muscles) Newsletter*, vol. 2, No. 1, Jul. 2000.

Bar-Cohen, Yoseph, JPL, *WorldWide ElectroActive Polymers, EAP (Artificial Muscles) Newsletter*, vol. 2, No. 2, Dec. 2000.

Bar-Cohen, Yoseph, JPL, *WorldWide ElectroActive Polymers, EAP (Artificial Muscles) Newsletter*, vol. 3, No. 1, Jun. 2001.

Bar-Cohen, Yoseph, JPL, *WorldWide ElectroActive Polymer Actuators Webhub* webpages 1-7, http://ndeaa.jpl.nasa.gov/nasa-nde/lommas/eap/EAP-web.htm, downloaded Jul. 23, 2001.

Baughman, R., L. Shacklette, R. Elsenbaumer, E. Plichta, and C. Becht "Conducting Polymer Electromechanical Actuators," *Conjugated Polymeric Materials: Opportunities in Electronics, Optoelectronics and Molecular Electronics*, eds. J.L. Bredas and R.R. Chance, Kluwer Academic Publishers, The Netherlands, pp. 559-582, 1990.

Baughman, R.H., L.W. Shacklette, and R.L. Elsenbaumer, E.J. Plichta, and C. Becht, "Micro electromechanical actuators based on conducting polymers", in *Molecular Electronics, Materials and Methods*, P.I. Lazarev (ed.), Kluwer Academic Publishers, pp. 267-289 (1991).

Bharti, V., Y. Ye, T.-B. Xu and Q. M. Zhang, "Correlation Between Large Electrostrictive Strain and Relaxor Behavior with Structural Changes Induced in P(VDF-TrFE) Copolymer by electron Irradiation," Mat. Res. Soc. Symp. Proc. vol. 541, pp. 653-659 (1999).

Bharti, V., Z.-Y. Cheng, S. Gross, T.-B. Xu, and Q. M. Zhang, "High electrostrictive strain under high mechanical stress in electron-irradiated poly(vinylidene fluoride-trifluoroethylene) copolymer," Appl. Phys. Lett. vol. 75, 2653-2655 (Oct. 25, 1999).

Bharti, V., H. S. Xu, G. Shanthi, and Q. M. Zhang, "Polarization and Structural Properties of High Energy Electron Irradiated Poly(vinylidene fluoride-trifluoroethylene) Copolymer Films," to be published in J. Appl. Phys. (2000).

Bharti, V., X.-Z. Zhao, Q. M. Zhang, T. Romotowski, F. Tito, and R. Ting, "Ultrahigh Field Induced Strain And Polarization Response In Electron Irradiated Poly(Vinylidene Fluoride-Trifluoroethylene) Copolymer," *Mat. Res. Innovat.* vol. 2, 57-63 (1998).

Bobbio, S., M Kellam, B. Dudley, S. Goodwin Johansson, S. Jones, J. Jacobson, F. Tranjan, and T. DuBois, "Integrated Force Arrays," in Proc. IEEE Micro ElectroMechanical Systems Workshop, Fort Lauderdale, Florida Feb. 1993.

Bohon, K., and S. Krause, "An Electrorheological Fluid and Siloxane Gel Based Electromechanical Actuator: Working Toward an Artificial Muscle," to be published in *J. Polymer Sci., Part B. Polymer Phys.* (2000).

Brock, D. L., "Review of Artificial Muscle based on Contractile Polymers," MIT Artificial Intelligence Laboratory, A.I. Memo No. 1330, Nov. 1991.

Caldwell, D., G. Medrano-Cerda, and M. Goodwin, "Characteristics and Adaptive Control of Pneumatic Muscle Actuators for a Robotic Elbow," Proc. IEEE Int. Conference on Robotics and Automation, San Diego, California (May 8-13, 1994).

Calvert, P. and Z. Liu, "Electrically stimulated bilayer hydrogels as muscles," Proceedings of the SPIE International Symposium on Smart Structures and Materials: Electro-Active Polymer Actuators and Devices, Mar. 1-2, 1999, Newport Beach, California, USA, pp. 236-241.

Cheng, Z.-Y., H. S. Xu, J. Su, Q. M. Zhjang, P.-C. Wang, and A. G. MacDiarmid, "High performance of all-polymer electrostrictive systems," Proceedings of the SPIE International Symposium on Smart Structures and Materials: Electro-Active Polymer Actuators and Devices, Mar. 1-2, 1999, Newport Beach, California, USA., pp. 140-148.

Cheng, Z.-Y., T.-B. Xu, V. Bharti, S. Wang, and Q. M. Zhang, "Transverse Strain Responses In The Electrostrictive Poly(Vinylidene Fluoride-Trifluorethylene) Copolymer," *Appl. Phys. Lett.* vol. 74, No. 13, pp. 1901-1903, Mar. 29, 1999.

Chiarelli, P., A. Della Santa, D. DeRossi, and A. Mazzoldi. 1995. "Actuation Properties of Electrochemically Driven Polypyrrole Free-standing Films," *Journal of Intelligent Material Systems and Structures,* vol. 6, pp. 32-37, Jan. 1995.

De Rossi, D., and P. Chiarelli. 1994. "Biomimetic Macromolecular Actuators," *Macro-Ion Characterization, American Chemical Society Symposium Series,* vol. 548, Ch. 40, pp. 517-530.

Dowling, K., *Beyond Faraday-Non Traditional Actuation,* available on the World Wide Web at http://www.frc.ri.cmu.edu/~nivek/OTH/beyond-faraday/beyondfaraday.html, 9 pages, 1994.

Egawa, S. and T. Higuchi, "Multi-Layered Electrostatic Film Actuator," Proc. IEEE Micro Electra Mechanical Systems, Napa Valley, California, pp. 166-171 (Feb. 11-14, 1990).

Elhami, K., and B. Gauthier-Manuel, "Electrostriction Of The Copolymer Of Vinylidene-Fluoride And Trifluoroethylene," *J. Appl. Phys.* vol. 77 (8), 3987-3990, Apr. 15, 1995.

Flynn, Anita M., L.S. Tavrow, S.F. Bart, R.A. Brooks, D.J. Ehrlich, K.R. Udayakumar, and L.E. Cross. 1992. "Piezoelectric Micromotors for Microrobots," *IEEE Journal of Microelectromechanical Systems,* vol. 1, No. 1, pp. 44-51 (Mar. 1992); also published as *MIT Al Laboratory Memo 1269,* Massachusetts Institute of Technology (Feb. 1991).

Full, R. J. and K. Meijer, "Artificial Muscles Versus Natural Actuators From Frogs To Flies," Proceedings of the 7th SPIE Symposium on Smart Structures and Materials-Electroactive Polymers and Devices (EAPAD) Conference, Mar. 6-8, 2000, Newport Beach, California, USA, pp. 2-9.

Furuhata, T., T. Hirano, and H. Fujita, "Array-Driven Ultrasonic Microactuators," Solid State Sensors and Actuators, 1991, Digest of Tech. Papers, Transducers, pp. 1056-1059.

Furukawa, T., and N. Seo., "Electrostriction as the Origin of Piezoelectricity in Ferroelectric Polymers," *Japanese J. Applied Physics,* vol. 29, No. 4, pp. 675-680 (Apr. 1990).

Gilbertson, R.G., and J.D. Busch. 1994. "Survey of Micro-Actuator Technologies for Future Spacecraft Missions," presented at the conference entitled "Practical Robotic Interstellar Flight: Are We Ready?" New York University and The United Nations, New York. (Aug. 29 and Sep. 1, 1994); also published on the World Wide Web at http://nonothinc.com/nanosci/microtech/mems/ten-actuators/gilbertson.html.

Goldberg, Lee, Adaptive-Filtering Developments Extend Noise-Cancellation Applications, *Electronic Design,* Feb. 6, 1995, pp. 34 and 36.

M. Greene and J. A. Willett, and Kornbluh, R., "Robotic systems," in ONR Report 32198-2, Ocean Engineering and Marine Systems 1997 Program (Dec. 1997).

Greenland, P., Allegro Microsystems Inc., and Carsten, B., Bruce Carsten Associates, "Stacked Flyback Converters Allow Lower Voltage MOSFETs for High AC Line Voltage Operation", *Feature PCIM Article, PCIM,* Mar. 2000.

Heydt, R., R. Pelrine, J. Joseph, J. Eckerle, and R. Kornbluh. "Acoustical Performance of an Electrostrictive Polymer Film Loudspeaker", *Journal of the Acoustical Society of America* vol. 107, pp. 833-839 (Feb. 2000).

Heydt, R., R. Kornbluh, R. Pelrine, and B. Mason, "Design and Performance of an Electrostrictive Polymer Film Acoustic Actuator", *Journal of Sound and Vibration* (1998)215(2), 297-311.

Hirano, M., K. Yanagisawa, H. Kuwano, and S. Nakano, "Microvalve with Ultra-low Leakage," Tenth Annual International Workshop on Micro Electromechanical Systems, Nagoya, Japan, *IEEE Proceedings* (Jan. 26-30, 1997), pp. 323-326.

Hirose, S., Biologically Inspired Robots: Snake-like Locomotors and Manipulators, *"Development of the ACM as a Manipulator",* Oxford University Press, New York, 1993, pp. 170-172.

Hunter, I., S. Lafontaine, J. Hollerbach, and P. Hunter, "Fast Reversible NiTi Fibers for Use in MicroRobotics," *Proc. 1991 IEEE Micro Electro Mechanical Systems-MEMS '91,* Nara, Japan, pp. 166-170.

Hunter, I.W., and S. Lafontaine, "A Comparison of Muscle with Artificial Actuators", *Technical Digest of the IEEE Solid-state Sensor and Actuator Workshop,* Hilton Head, South Carolina, Jun. 22-25, 1992, pp. 178-185.

Jacobsen, S., Price, R., Wood, J, Rytting, T., and Rafaelof, M., "A Design Overview of an Eccentric-Motion Electrostatic Microactuator (the Wobble Motor)", *Sensors and Actuators,* 20 (1989) pp. 1-16.

Kaneto, K., M. Kaneko, Y. Min, and A.G. MacDiarmid. 1995. "'Artificial Muscle': Electromechanical Actuators Using Polyaniline Films," *Synthetic Metals 71,* pp. 2211-2212, 1995.

Kawamura, S., K. Minani, and M. Esashi, "Fundamental Research of Distributed Electrostatic Micro Actuator," Technical Digest of the 11th Sensor Symposium, pp. 27-30(1992).

Kondoh Y., and T. Ono. 1991. "Bimorph Type Actuators using Lead Zinc Niobate-based Ceramics," *Japanese Journal of Applied Physics,* vol. 30, No. 9B, pp. 2260-2263, Sep. 1991.

Kornbluh, R., R. Pelrine, R. Heydt, and Q. Pei, "Acoustic Actuators Based on the Field-Activated Deformation of Dielectric Elastomers," (2000).

Kornbluh, R., G. Andeen, and J. Eckerle, "Artificial Muscle: The Next Generation of Robotic Actuators," presented at the Fourth World Conference on Robotics Research, SME Paper M591-331, Pittsburgh, PA, Sep. 17-19, 1991.

Kornbluh, R., R. Pelrine, J. Joseph, "Elastomeric Dielectric Artificial Muscle Actuators for Small Robots," *Proceedings of the Third IASTED International Conference on Robotics and Manufacturing,* Jun. 14-16, 1995, Cancun, Mexico.

Kornbluh, R., Pelrine, R., Eckerie, J., Joseph, J., "Electrostrictive Polymer Artificial Muscle Actuators", IEEE International Conference on Robotics and Automation, Leuven, Belgium, 1998.

Kornbluh, R., R. Pelrine, Jose Joseph, Richard Heydt, Qibing Pei, Seiki Chiba, 1999. "High-Field Electrostriction Of Elastomeric Polymer Dielectrics For Actuation", Proceedings of the SPIE International Symposium on Smart Structures and Materials: Electro-Active Polymer Actuators and Devices, Mar. 1-2, 1999, Newport Beach, California, USA. pp. 149-161.

Kornbluh, R. D and R. E. Pelrine., "Dexterous Multiarticulated Manipulator with Electrostrictive Polymer Artificial Muscle," ITAD-7247-QR-96-175, SRI Project No. 7247, Prepared for: Office of Naval Research, Nov. 1996.

Kornbluh, R., R. Pelrine, Q. Pei, S. Oh, and J. Joseph, 2000. "Ultrahigh Strain Response of Field-Actuated Elastomeric Polymers," Proceedings of the 7th SPIE Symposium on Smart Structures and Materials-Electroactive Polymers and Devices (EAPAD) Conference, Mar. 6-8, 2000, Newport Beach, California, USA, pp. 51-64.

Kornbluh, R. Pelrine, R. Joseph, J., Pei, Q. and Chiba, S., "Ultra-High Strain Response of Elastomeric Polymer Dielectrics", Proc. Materials Res. Soc., Fall meeting, Boston, MA, pp. 1-12, Dec. 1999.

Ktech's PVDF Sensors, http://www.ktech.com/pvdf.htm, Jun. 6, 2001, pp. 1-5.

Lang, J, M. Schlect, and R. Howe, "Electric Micromotors: Electromechanical Characteristics," Proc. IEEE Micro Robots and Teleoperators Workshop, Hyannis, Massachusetts (Nov. 9-11, 1987).

Liu, Y., T. Zeng, Y.X. Wang, H. Yu, and R. Claus, "Self-Assembled Flexible Electrodes on Electroactive Polymer Actuators," Proceedings of the SPIE International Symposium on Smart Structures and Materials: Electro-Active Polymer Actuators and Devices, Mar. 1-2, 1999, Newport Beach, California, USA., pp. 284-288.

Liu, C., Y. Bar-Cohen, and S. Leary, "Electro-statically stricted polymers (ESSP)," Proceedings of the SPIE International Symposium on Smart Structures and Materials: Electro-Active Polymer Actuators and Devices, Mar. 1-2, 1999, Newport Beach, California, USA., pp. 186-190.

Lawless, W. and R. Arenz, "Miniature Solid-state Gas Compressor," *Rev. Sci Instrum.,* 58(8), pp. 1487-1493, Aug. 1987.

Martin, J. and R. Anderson, 1999. "Electrostriction In Field-Structured Composites: Basis For A Fast Artificial Muscle?", *Journal of Chemical Physics,* vol. 111, No. 9, pp. 4273-4280, Sep. 1, 1999.

Measurements Specialties, Inc.—Piezo Home, http://www.msiusa.com/piezo/index.htm, Jun. 6, 2001.

T.B. Nguyen, C. K. DeBolt, Shastri, S. V., and A. Mann, "Advanced Robotic Search," in ONR Ocean, Atmosphere, and Space Fiscal Year 1999 Annual Reports (Dec. 1999).

Nguyen, T., J. A. Willett and Kornbluh, R., "Robotic systems," in ONR Ocean, Atmosphere, and Space Fiscal Year 1998 Annual Reports (Dec. 1998).

Nguyen, T., Green, M., and Kornbluh, R., "Robotic Systems," in ONR Ocean, Atmosphere, and Space Fiscal Year 1999 Annual Reports (Dec. 1999).

Ohara, K., M. Hennecke, and J. Fuhrmann, "Electrostriction of polymethylmethacrylates," *Colloid & Polymer Sci.* vol. 280, 164-168 (1982).

Olsson, A., O. Larsson, J. Holm, L. Lundbladh, O. Ohinan, and G. Stemme. 1997. "Valve-less Diffuser Micropumps Fabricated using Thermoplastic Replication," *Proc. IEEE Micro Electro Mechanical Systems,* Nagoya, Japan, pp. 305-310 (Jan. 26-30, 1997).

Olsson, A., G. Stemme, and E. Stemme, "The First Valveless Diffuser Gas Pump," Tenth Annual International Workshop on Micro Electromechanical Systems, Nagoya, Japan, *IEEE Proceedings* (Jan. 26-30, 1997), pp. 108-113.

Otero, T.F., J. Rodriguez, E. Angulo and C. Santamaria, "Artificial Muscles from Bilayer Structures," *Synthetic Metals,* vol. 55-57, pp. 3713-3717 (1993).

Otero, T.F., J. Rodriguez, and C. Santamaria, "Smart Muscle Under Electrochemical Control of Molecular Movement in Polypyrrole Films," *Materials Research Society Symposium Proceedings,* vol. 330, pp. 333-338, 1994.

Park, S.E., and T. Shrout., "Ultrahigh Strain and Piezoelectric Behavior in Relaxor Based Ferroelectric Single Crystals," *J Applied Physics,* vol. 82, pp. 1804-1811, Aug. 15, 1997.

Pei, Q., O. Inganäs, and I. Lundström, "Bending Bilyaer Strips Built From Polyaniline For Artificial Electrochemical Muscles," *Smart Materials and Structures,* vol. 2, pp. 16., Jan. 22, 1993.

Pei et al., "Improved Electroactive Polymers", U.S. Appl. No. 09/619,847, filed Jul. 20, 2000, 70 pages.

R. Pelrine and Kornbluh, R., and. 1995. *"Dexterous Multiarticulated Manipulator with Electrostrictive Polymer Artificial Muscle Actuator,"* EMU 95-023, SRI International, Menlo Park, California, Apr. 28, 1995.

Pelrine, R., R. Kornbluh, and Q. Pei. "Electroactive Polymer Transducers And Actuators", U.S. Appl. No. 09/620,025, filed Jul. 20, 2001, 58 pages.

Pelrine, R., R. Kornbluh, and J. Joseph, "Electrostriction of Polymer Dielectrics with Compliant Electrodes as a Means of Actuation," *Senros and Actuators A: Physical,* vol. 64, 1998, pp. 77-85.

Pelrine, R, R. Kornbluh, J. Joseph, and S. Chiba, "Electrostriction of Polymer Films for Microactuators," *Proc. IEEE Tenth Annual International Workshop on Micro Electro Mechanical Systems,* Nagoya, Japan, Jan. 26-30, 1997, pp. 238-243.

Pelrine et al. "Electroactive Polymer Generators", U.S. Appl. No. 09/619,848, filed Jul. 20, 2000, 69 pages.

Pelrine, R., and J. Joseph, *FY 1992 Final Report on Artificial Muscle for Small Robots,* ITAD-3393-FR-93-063, SRI International, Menlo Park, California, Mar. 1993.

Pelrine, R., and J. Joseph. 1994. *FY 1993 Final Report on Artificial Muscle for Small Robots,* ITAD-4570-FR-94-076, SRI International, Menlo Park, California.

Pelrine, R., R. Kornbluh, and J. Joseph, *FY 1994 Final Report on Artificial Muscle for Small Robots,* ITAD-5782-FR-95-050, SRI International, Menlo Park, California, 1995.

Pelrine, R., R. Kornbluh, and J. Joseph, *FY 1995 Final Report on Artificial Muscle for Small Robots,* ITAD-7071-FR-96-047, SRI International, Menlo Park, California, 1996.

Pelrine, R., R. Kornbluh, and J. Joseph, FY 1996 *Final Report on Artificial Muscle for Small Robots,* ITAD-7228-FR-97-058, SRI International, Menlo Park, California, 1997.

Pelrine, R., R. Kornbluh, and J. Joseph, FY 1997 *Final Report on Artificial Muscle for Small Robots*, ITAD-1612-FR-98-041, SRI International, Menlo Park, California, 1998.

Pelrine, R., R. Kornbluh, and J. Joseph, FY 1998 *Final Report on Artificial Muscle for Small Robots*, ITAD-3482-FR-99-36, SRI International, Menlo Park, California, 1999.

Pelrine, R., R. Kornbluh, and J. Joseph, FY 1999 *Final Report on Artificial Muscle for Small Robots*, ITAD-10162-FR-00-27, SRI International, Menlo Park, California, 2000.

Pelrine, R., R. Kornbluh, Q. Pei, and J. Joseph. "High-Speed Electrically Actuated Elastomers with Strain Greater Than 100%", *Science,* Reprint Series, Feb. 4, 2000, vol. 287, pp. 836-839.

Pelrine, R., R. Kornbluh, Q. Pei, and J. Joseph, "High Speed Electrically Actuated Elastomers with Over 100% Strain," *Science,* vol. 287, No. 5454, pp. 1-21, 2000.

Pelrine, R., R. Kornbluh, and G. Kofod, "High Strain Actuator Materials Based on Dielectric Elastomers," submitted to *Advanced Materials* (May 2000).

Pelrine, R., Roy Kornbluh, Jose Joseph, Qibing Pei, Seiki Chiba "Recent Progress in Artificial Muscle Micro Actuators,", SRI International, Tokyo, 1999 MITI/NEEDOIMNIC, 1999.

Pelrine, R., J. Eckerle, and S. Chiba, "Review of Artificial Muscle Approaches," invited paper, in *Proc. Third International Symposium on Micro Machine and Human Science*, Nagoya, Japan, Oct. 14-16, 1992.

Pelrine, R., R. Kornbluh, and J. Eckerle. "Energy Efficient Electroactive Polymers and Electroactive Polymer Devices", U.S. Appl. No. 09/779,373, filed Feb. 7, 2001.

Pelrine, R., R. Kornbluh, J. Eckerle, S. Stanford, S. Oh, and P. Garcia. "Biologically Powered Electroactive Polymer Generators", U.S. Appl. No. 09/792,877, filed Feb. 23, 2001, 92 pages.

Piezoflex™ PVDF Polymer Sensors, http://www.airmar.com/piezo/pvdf.htm, Jun. 6, 2001.

Scheinbeim, J., B. Newman, Z. Ma, and J. Lee, "Electrostrictive Response of Elastomeric Polymers," *ACS Polymer Preprints*, 33(2), pp. 385-386, 1992.

Schlaberg, H. I., and J. S. Duffy, "Piezoelectric Polymer Composite Arrays For Ultrasonic Medical Imaging Applications," *Sensors and Actuators*, A 44, pp. 111-117, Feb. 22, 1994.

Shahinpoor, M., "Micro-electro-mechanics of Ionic Polymer Gels as Electrically Controllable Artificial Muscles," *J. Intelligent Material Systems and Structures*, vol. 6, pp. 307-314, May 1995.

Shkel, Y., and D. Klingenberg, "Material Parameters for Electrostriction," *J. Applied Physics*, vol. 80(8), pp. 4566-4572, Oct. 15, 1996.

Smela, E., O. Inganäs, and I. Lundström, "Controlled Folding of Micrometer-size Structures," *Science*, vol. 268, pp. 1735-1738 (Jun. 23, 1995).

Su, J., Z. Ounaies, J. S. Harrison, Y. Bara-Cohen and S. Leary, "Electromechanically Active Polymer Blends for Actuation," Proceedings of the 7th SPIE Symposium on Smart Structures and Materials-Electroactive Polymers and Devices (EAPAD) Conference, Mar. 6-8, 2000, Newport Beach, California, USA, pp. 65-72.

Technology, http://www.micromuscle.com/html/technology.html, Jun. 6, 2001.

Tobushi, H., S. Hayashi, and S. Kojima, "Mechanical Properties of Shape Memory Polymer of Polyurethane Series," in *JSME International Journal*, Series I, vol. 35, No. 3, 1992.

Treloar, L.R.G, "Mechanics of Rubber Elasticity," *J Polymer Science, Polymer Symposium*, No. 48, pp. 107-123, 1974.

Uchino, K. 1986. "Electrostrictive Actuators: Materials and Applications," *Ceramic Bulletin*, 65(4), pp. 647-652, 1986.

Wade, W. L., Jr., R. J. Mammone and M. Binder, "Increased Dielectric Breakdown Strengths Of Melt-Extruded Polyporpylene Films," *Polymer*, vol. 34, No. 5, pp. 1093-1094 (1993).

Yam, P., "Plastics Get Wired", *Scientific American*, vol. 273, pp. 82-87, Jul. 1995.

Zhang, Q. M., V. Bharti, Z.-Y. Cheng, T.-B. Xu, S. Wang, T. S. Ramotowski, F. Tito, and R. Ting, "Electromechanical Behavior of Electroactive P(VDF-TrFE) Copolymers," Proceedings of the SPIE International Symposium on Smart Structures and Materials: Electro-Active Polymer Actuators and Devices, Mar. 1-2, 1999, Newport Beach, California, USA., pp. 134-139.

Zhang, Q., V. Bharti, and X. Zhao, "Giant Electrostriction and Relaxor Ferroelectric Behavior in Electron-irradiated Poly(vinylidene fluoride-trifluoroethylene) Copolymer," *Science*, vol. 280, pp. 2101-2104 (Jun. 26, 1998).

Zhang, Q. M., Z.-Y. Cheng, V. Bharti, T.-B. Xu, H. Xu, T. Mai, and S. J. Gross, "Piezoelectric And Electrostrictive Polymeric Actuator Materials," Proceedings of the 7th SPIE Symposium on Smart Structures and Materials-Electroactive Polymers and Devices (EAPAD) Conference, Mar. 6-8, 2000, Newport Beach, California, USA, pp. 34-50.

Zhenyi, M., J.I. Scheinbeim, J.W. Lee, and B.A. Newman. 1994. "High Field Electrostrictive Response of Polymers," *Journal of Polymer Sciences, Part B-Polymer Physics*, vol. 32, pp. 2721-2731, 1994.

Smela, E., O. Inganäs, Q. Pei, and I. Lundström, "Electrochemical Muscles: Micromachining Fingers and Corkscrews,"*Advanced Materials*, vol. 5, No. 9, pp. 630-632, Sep. 1993.

Su, J., Q. M. Zhang, C. H. Kim, R. Y. Ting, and R. Capps, "Effects of Transitional Phenomena on the Electric Field induced Strain-electrostrictive Response of a Segmented Polyurethane Elastomer," pp. 1363-1370, Jan. 20, 1997.

Pelrine R. E., et al.: "Electrostriction of Polymer Dielectrics with Compliant Electrodes As A Means of Actuation", Sensors and Actuators A., Elsevier Sequoia S.A., Lausanne, Ch, vol. 64, No. 1, 1998, pp. 77-85, XP004102141, ISSN: 0924-4247.

Ron Pelrine, Roy Kornbluh, Qibing Pei, Jose Joseph: High-Speed ElectricallyActuated Elastomers With Strain Greater Than 100% Science, vol. 287, Feb. 4, 2000, pp. 836-839, XP002288990, USA the whole document.

\* cited by examiner

*Primary Examiner*—Thomas M. Dougherty
(74) *Attorney, Agent, or Firm*—Beyer Weaver & Thomas, LLP

(57) ABSTRACT

The invention describes devices for performing thermodynamic work on a fluid, such as pumps, compressors and fans. The thermodynamic work may be used to provide a driving force for moving the fluid. Work performed on the fluid may be transmitted to other devices, such as a piston in a hydraulic actuation device. The devices may include one or more electroactive polymer transducers with an electroactive polymer that deflects in response to an application of an electric field. The electroactive polymer may be in contact with a fluid where the deflection of the electroactive polymer may be used to perform thermodynamic work on the fluid. The devices may be designed to efficiently operate at a plurality of operating conditions, such as operating conditions that produce an acoustic signal above or below the human hearing range. The devices may be used in thermal control systems, such as refrigeration system, cooling systems and heating systems.

12 Claims, 23 Drawing Sheets

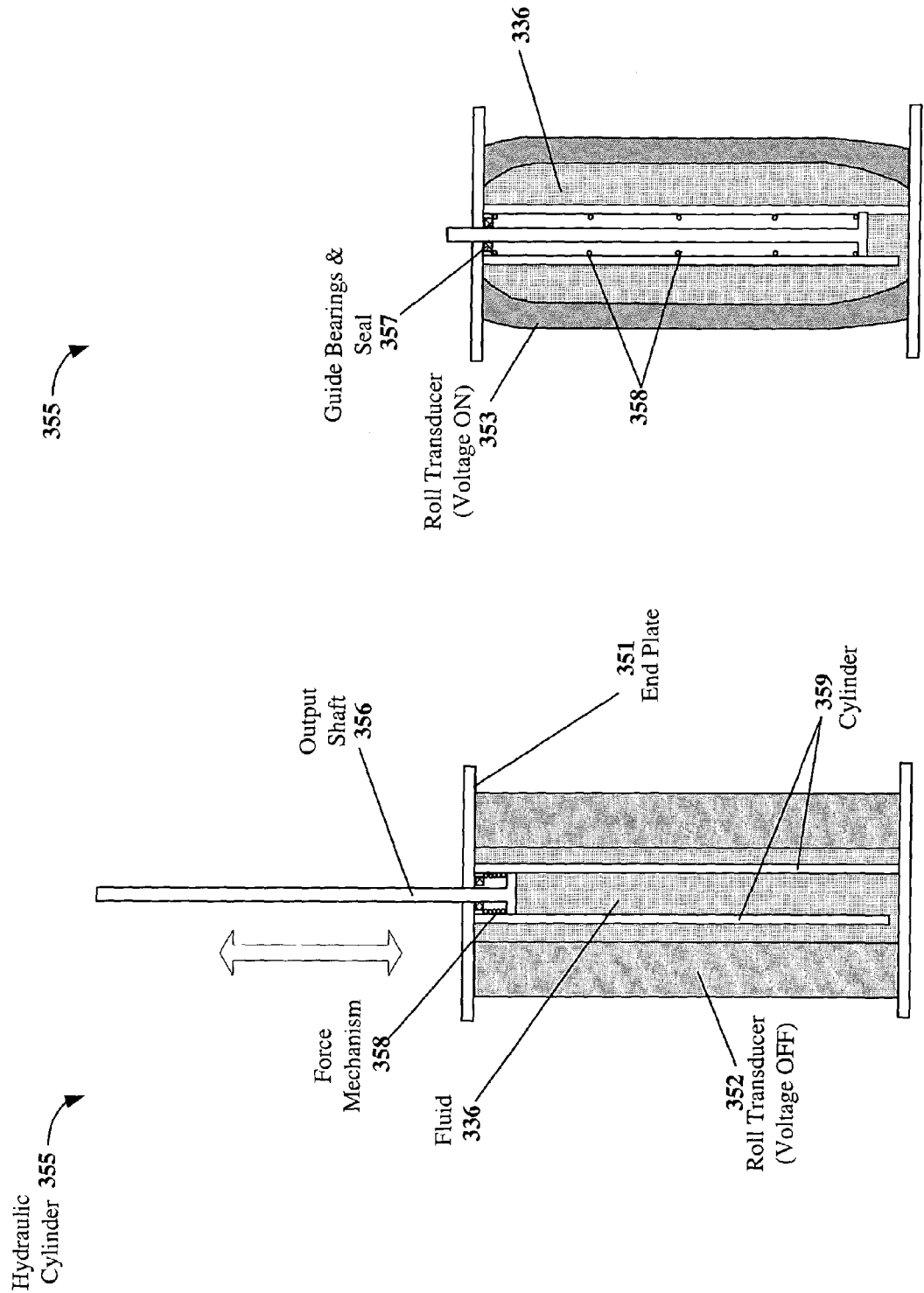

ELECTROACTIVE POLYMER DEVICES FOR MOVING FLUID

CROSS-REFERENCE TO RELATED APPLICATION

This application claims priority under 35 U.S.C. §119(e) from co-pending; U.S. Provisional Patent Application No. 60/365,472, by Pelrine, et al., "Electroactive Polymer Devices For Moving Fluid," filed Mar. 18, 2002 which is incorporated by reference for all purposes;

and the application is a continuation-in-part and claims priority from U.S. patent application Ser. No. 09/792,431 entitled "Electroactive Polymer Thermal Electric Generators," filed Feb. 23, 2001 now U.S. Pat. No. 6,628,040, which is incorporated herein by reference in its entirety for all purposes which claims priority under 35 U.S.C. §119(e) from U.S. Provisional Patent Application No. 60/184,217 filed Feb. 23, 2000, naming Q. Pei et al. as inventors, and titled "Electroelastomers And Their Use For Power Generation", which is incorporated by reference herein for all purposes and which also claims priority under 35 U.S.C. §119(e) from U.S. Provisional Patent Application No. 60/190,713 filed Mar. 17, 2000, naming J. S. Eckerle et al. as inventors, and titled "Artificial Muscle Generator", which is incorporated by reference herein for all purposes;

and the application is a continuation-in-part and claims priority from U.S. patent application Ser. No. 10/154,449 entitled "Rolled Electroactive Polymers," filed May 21, 2002 now U.S. Pat. No. 6,891,317 which is incorporated herein by reference in its entirety for all purposes which claims priority under 35 U.S.C. §119(e) from U.S. Provisional Patent Application No. 60/293,003 filed on May 22, 2001, which is incorporated by reference for all purposes;

and the application is a continuation-in-part and claims priority from U.S. patent application Ser. No. 10/053,511 entitled "Variable Stiffness Electroactive Polymer Systems," filed Jan. 16, 2002 now U.S. Pat. No. 6,882,086 which is incorporated herein by reference in its entirety for all purposes which claims priority under 35 U.S.C. §119(e) from U.S. Provisional Patent Application No. 60/293,005 filed May 22, 2001, which is incorporated by reference herein for all purposes; and which claims priority under 35 U.S.C. §119(e) from U.S. Provisional Patent Application No. 60/327,846 entitled Enhanced Multifunctional Footwear and filed Oct. 5, 2001, which is incorporated by reference herein for all purposes;

and the application is a continuation-in-part and claims priority from U.S. patent application Ser. No. 09/619,847 entitled "Improved Electroactive Polymers," filed Jul. 20, 2000 now U.S. Pat. No. 6,812,624 which is incorporated herein by reference in its entirety for all purposes which claims priority under 35 U.S.C. §119(e) from U.S. Provisional Patent Application No. 60/144,556 filed Jul. 20, 1999, naming R. E. Pelrine et al. as inventors, and titled "High-speed Electrically Actuated Polymers and Method of Use", which is incorporated by reference herein for all purposes and which claims priority under 35 U.S.C. §119(e) from U.S. Provisional Patent Application No. 60/153,329 filed Sep. 10, 1999, naming R. E. Pelrine et al. as inventors, and titled "Electrostrictive Polymers As Microactuators", which is incorporated by reference herein for all purposes and which claims priority under 35 U.S.C. §119(e) from U.S. Provisional Patent Application No. 60/161,325 filed Oct. 25, 1999, naming R. E. Pelrine et al. as inventors, and titled "Artificial Muscle Microactuators", which is incorporated by reference herein for all purposes and which claims priority under 35 U.S.C. §119(e) from U.S. Provisional Patent Application No. 60/181,404 filed Feb. 9, 2000, naming R. D. Kornbluh et al. as inventors, and titled "Field Actuated Elastomeric Polymers", which is incorporated by reference herein for all purposes and which claims priority under 35 U.S.C. §119(e) from U.S. Provisional Patent Application No. 60/187,809 filed Mar. 8, 2000, naming R. E. Pelrine et al. as inventors, and titled "Polymer Actuators and Materials", which is incorporated by reference herein for all purposes; and which claims priority under 35 U.S.C. §119(e) from U.S. Provisional Patent Application No. 60/192,237 filed Mar. 27, 2000, naming R. D. Kornbluh et al. as inventors, and titled "Polymer Actuators and Materials II", which is incorporated by reference herein for all purposes and which claims priority under 35 U.S.C. §119(e) from U.S. Provisional Patent Application No. 60/184,217 filed Feb. 23, 2000, naming R. E. Pelrine et al. as inventors, and titled "Electroelastomers and their use for Power Generation", which is incorporated by reference herein for all purposes;

and this application is a continuation-in-part and claims priority from U.S. patent application Ser. No. 10/007,705 entitled "Electroactive Polymer Sensors," filed Dec. 6, 2001 now U.S. Pat. No. 6,809,462, which claims priority under 35 U.S.C. §119(e) from U.S. Provisional Patent Application No. 60/293,004 filed May 22, 2001, which is incorporated by reference herein for all purposes and which is also a continuation in part of U.S. patent application Ser. No. 09/828,496 filed Apr. 4, 2001, now U.S. Pat. No. 6,586,859, which claims priority from U.S. Provisional Application No. 60/194,817 filed Apr. 5, 2000, all of which are incorporated by reference herein for all purposes;

and this application is a continuation-in-part and claims priority from co-pending U.S. patent application Ser. No. 10/066,407 entitled "Devices and Methods for Controlling Fluid Flow Using Elastic Sheet Deflection," filed Jan. 31, 2002, which is incorporated by reference herein for all purposes an this application is a continuation-in-pat and claims priority from U.S. patent application Ser. No. 09/779,203, filed Feb. 7, 2001 now U.S. Pat. No. 6,664,718, by Pelrine, et al, and entitled, "Monolithic Electroactive Polymers," which claims priority under 35 U.S.C. §119(e) from U.S. Provisional Patent Application No. 60/181,404, which is incorporated by reference for all purposes and this application is a continuation-in-part and claims priority from U.S. patent application Ser. No. 10/090,430, filed on Feb. 28, 2002 now U.S. Pat. No. 6,806,621, by Heim, et al. and titled, "Electroactive Polymer Rotary Motors," which claims priority under 35 U.S.C. §119(e) from U.S. Provisional Patent Application No. 60/273,108, filed Mar. 2, 2001 and titled, "Electroactive Polymer Motors," both of which are incorporated by reference for all purposes.

This application is related to co-pending U.S. application Ser. No. 10/383,005, filed on Mar. 5, 2003, by Heim, et al., and entitled, "Electroactive Polymer Devices for Controlling Fluid Flow," which is incorporated herein in its entirety and for all purposes.

and the application is a continuation-in-part and claims priority co-pending from U.S. patent application Ser. No. 10/047,485 entitled "Elastomeric Dielectric Polymer Film Sonic Actuator," filed Oct. 26, 2001; which is a continuation of U.S. patent application Ser. No. 09/356,801 filed Jul. 19, 1999 and now issued as U.S. Pat. No. 6,343,129 which claims the benefit of International Application No. PCT/US98/02311 filed on Feb. 2, 1998 which application is entitled to the priority benefit of co-pending U.S. provisional patent application No. 60/037,400, filed Feb. 7, 1997.

U.S. GOVERNMENT RIGHTS

This application was made in part with government support under contract number N00014-02-C-0252 awarded by the Defense Advanced Research Projects Agency and the Office of Naval Research. The government has certain fights in the invention.

BACKGROUND OF THE INVENTION

The present invention relates generally to electroactive polymer devices that convert between electrical energy and mechanical energy. More particularly, the present invention relates to pumping devices comprising one or more electroactive polymer transducers.

Fluid systems are ubiquitous. The automotive industry, the plumbing industry, chemical processing industry, computer industry, refrigeration/cooling industry, home appliance industry, and the aerospace industry are a few examples where fluid systems are of critical importance. In most fluid systems, it is often desirable to perform thermodynamic work on the fluid in the fluid system. The thermodynamic work, such as in the case of a pump or fan, may be used to provide the energy needed to move the fluid in the fluid system from one location to another location in the fluid system. As another example, the thermodynamic work may be used to place the fluid in a desirable thermodynamic state, such as compressing the fluid in a refrigeration system to convert it from a gas phase to a liquid or compressing the fluid in a combustion system prior to combustion such as in an automobile engine. In yet another example, thermodynamic work may be performed on a fluid as a means of energy transfer, such as in a hydraulic lift or hydraulic control system.

In general, pumps, fans and compressors have wide ranging applications in both the home and industrial environment. As examples, pumps, fans and/or compressors are used for circulating refrigerant and removing waste heat in cooling systems (e.g., air conditioning, refrigeration), pumping water in washing machine and dishwashers, removing waste heat from heat sources (e.g., CPU) in the computing industry, pressurizing air for pneumatic systems, transporting water for irrigation, transporting oil and gas in pipelines, and moving fluids between various unit operations in a chemical process plant. Pumps and compressors are also used widely in biomedical applications including, for example, circulating blood for dialysis or during surgical procedures.

Pumps, fans and compressors have been in existence for centuries for performing thermodynamic work on a fluid. Conventional pumps and compressors are predominantly piston-driven with an electric motor; these conventional devices tend to be heavy (bulky), noisy, inefficient at slow speeds (or require gearboxes to step down higher speeds), and can be mechanically complex and costly. Electric motors are generally designed to operate in the 50–500 Hz range. These motors usually operate in the audible range and need to be geared down (with the associated cost, weight, inefficiency, and complexity) to the proper pump or compressor frequency. For many applications, there is a need for pumps, fans, compressors and hydraulic devices that are more lightweight, higher power and efficiency, quieter, and lower cost.

New high-performance polymers capable of converting electrical energy to mechanical energy, and vice versa, are now available for a wide range of energy conversion applications. One class of these polymers, electroactive elastomers (also called dielectric elastomers, electroelastomers, or EPAM), is gaining wider attention. Electroactive elastomers may exhibit high energy density, stress, and electromechanical coupling efficiency. The performance of these polymers is notably increased when the polymers are pre-strained in area. For example, a 10-fold to 25-fold increase in area significantly improves performance of many electroactive elastomers. Actuators and transducers produced using these materials can be significantly cheaper, lighter and have a greater operation range as compared to conventional technologies used for performing thermodynamic work on a fluid in a fluid system.

Thus, improved techniques for implementing these high-performance polymers in devices used for performing thermodynamic work on a fluid in a fluid system would be desirable.

SUMMARY OF THE INVENTION

The invention describes devices for performing thermodynamic work on a fluid, such as pumps, compressors and fans. The thermodynamic work may be used to provide a driving force for moving the fluid. Work performed on the fluid may be transmitted to other devices, such as a piston in a hydraulic actuation device. The devices may include one or more electroactive polymer transducers with an electroactive polymer that deflects in response to an application of an electric field. The electroactive polymer may be in contact with a fluid where the deflection of the electroactive polymer may be used to perform thermodynamic work on the fluid. The devices may be designed to efficiently operate at a plurality of operating conditions, such as operating conditions that produce an acoustic signal above or below the human hearing range. The devices may be used in thermal control systems, such as refrigeration system, cooling systems and heating systems.

One aspect of the present invention provides a device for performing thermodynamic work on a fluid. The device may be generally characterized as comprising: i) one or more transducers, each transducer comprising at least two electrodes and an electroactive polymer in electrical communication with the at least two electrodes wherein a portion of the electroactive polymer is arranged to deflect from a first position to a second position in response to a change in electric field; and at least one surface in contact with a fluid and operatively coupled to the one or more transducers wherein the deflection of the portion of the electroactive polymer causes the thermodynamic work to be imparted to the fluid wherein the thermodynamic work is transmitted to the fluid via the one surface. The deflection of the one portion of the electroactive polymer may generate one of rotational motion, linear motion, vibrational motion or combinations thereof for the one surface. The thermodynamic work may provide a driving force to move the fluid from a first location to a second location.

The device may be one of a pump, a compressor, a hydraulic actuator and a fan. In particular, the device may be one of air compressor, a bellows bump, a fuel pump and a centrifugal pump. The device is one of a pump or a compressor for a refrigeration system.

The device may be a fan used in a ventilation system where the fluid is air. The device may be used in a thermal control system for controlling a temperature at one or more locations in a second device. As an example, the second device may be a computer and one of the locations is proximate to a microprocessor for the computer. The fluid may be used for conducting heat energy from a first location to a second location in the second device. In a particular embodiment, a portion of the fluid may be in a liquid phase.

In a particular embodiment, the device may further comprise a chamber for receiving the fluid where a bounding surface of the chamber includes the one surface. The deflection of the portion of the electroactive polymer causes a change in a volume of the chamber. The change in the volume in the chamber may compress the fluid in the chamber, may expand the fluid in the chamber, may draw fluid into the chamber or may expel fluid from the chamber. The change in the volume in the chamber may also cause a phase state change in at least a portion of the fluid, such as from a liquid to a gas or from a gas to a liquid.

In other embodiments, the chamber may be formed from one of a bladder or a bellows. The deflection of the portion of the electroactive polymer may squeeze the bladder or bellows to reduce a volume of the bladder or the bellows. The deflection of the portion of the electroactive polymer may also stretch the bladder or bellows to increase a volume of the bladder or the bellows. In yet another embodiment, the chamber may be formed from a cylinder and a piston wherein the one surface is a portion of a piston head.

In another embodiment, the device may further comprise a fan blade where the one surface is a portion of a surface of the fan blade. The deflection of the portion of the electroactive polymer may cause the fan blade to rotate. The deflection of the portion of the electroactive may cause 1) a shape of the fan blade to change to alter an aerodynamic performance of the fan blade, 2) a pitch of the fan blade to change and 3) a change in one of an aeroelastic property or an aeroacoustic property of the fan blade. The fan blade is a component in a fan, a pump or a compressor.

The device may also comprise one or more fluid conduits used to provide at least a portion of a flow path for allowing the fluid to travel through the device and one or more valves for controlling one of a flow rate, a flow direction and combinations thereof of the fluid through the flow path. The one or more valves may be a check valve. The device may further comprise a heat exchanger for adding or for removing heat energy from the fluid. In a particular embodiment, one or more portions of the electroactive polymer may act as the heat exchanger.

In other embodiment, the deflection of the portion of the polymer may induces a wave like motion in the one surface where the wave like motion imparts the thermodynamic work to the fluid. The device may further comprise a fluid conduit where the deflection of the portion of the electroactive polymer generates a peristaltic motion in the fluid conduit to move the fluid through the fluid conduit or where the deflection of the portion of electroactive polymer generates a wave-like motion in the fluid conduit to move fluid in the fluid conduit through the conduit. The fluid conduit may be comprised of an EPAM roll transducer.

The device may further comprise a force return mechanism where the force return mechanism provides at least a portion of a force for returning the portion of the electroactive polymer from the second position to the first position. The force return mechanism may be a spring. The device may also comprise a bias mechanism for biasing a direction of deflection of the portion of the electroactive polymer. The bias mechanism may be one of a spring or an insert. The device may also comprise an output shaft designed to receive a hydraulic force generated from a pressure in the fluid where the deflection in the portion of the electroactive polymer causes the pressure in the fluid to increase and provide the hydraulic force for moving the output shaft.

In yet other embodiment, the device may be a stage in one of a multi-stage pump or a multi-stage compressor. An acoustic signal generated by an operation of the device may be above or below a human hearing range. Further, an operating frequency at which the portion of the electroactive polymer deflects is above or below a human hearing range. For instance, the operating frequency may be below 30 Hz.

The device may further comprise a housing for enclosing the one or more transducers and the one surface. A flatness parameter defined as a height of the housing squared divided by a foot print area of the housing may be substantially less than 1. In particular, the flatness parameter may be less than about 0.1. Alternatively, the flatness parameter may be less than about 0.05. Further, the flatness parameter may be less than about 0.01.

In a particular embodiment, the device may further comprise a clamp plate with a plurality of apertures where the electroactive polymer is an electroactive polymer film designed to deflect into the plurality of apertures. Further, the device may comprise a lower chamber designed to mount to the clamp plate and to secure the film between the clamp plate and the lower chamber. A pumping chamber for receiving the fluid may be formed by a portion of a surface of the lower chamber and a portion of a surface of the film. The lower chamber may comprise one or more fluid conduits for conducting the fluid to the pumping chamber and for conducting the fluid away from the pumping chamber.

In particular embodiments, the deflection of the portion of the electroactive polymer may change the one surface from a first shape to a second shape. For instance, the one surface may expand to form one of a balloon-like shape, a hemispherical shape, a cylinder shape, or a half-cylinder shape. The one surface may be operatively coupled to the one or more transducers via a mechanical linkage. Further, the one surface may be an outer surface of the portion of the electroactive polymer.

The fluid may be compressible, incompressible or combinations thereof. The fluid may also be one of homogeneous or heterogeneous. Further, the fluid may behave as a Newtonian fluid or a non-Newtonian fluid. The fluid is selected from the group consisting of a mixture, a slurry, a suspension, a mixture of two or more immiscible liquids and combinations thereof. The fluid may include one or constituents in a state selected from the group consisting of a liquid, a gas, a plasma, a solid, a phase change and combinations thereof.

In other embodiments, the polymer may comprise a material selected from the group consisting of a silicone elastomer, an acrylic elastomer, a polyurethane, a copolymer comprising PVDF, and combinations thereof. The device may include an insulation barrier designed or configured to protect the one surface from constituents of the fluid in contact with the one surface or one or more support structures designed or configured to attach to the one or more transducers. The electroactive polymer may be elastically pre-strained at the first position to improve a mechanical response of the electroactive polymer between the first position and second position, may an elastic modulus below about 100 MPa and may have an elastic area strain of at least about 10 percent between the first position and the second position.

The polymer may comprise a multilayer structure where the multilayer structure comprises two or more layers of electroactive polymers. The device may be fabricated on a semiconductor substrate.

These and other features and advantages of the present invention will be described in the following description of the invention and associated figures.

BRIEF DESCRIPTION OF THE DRAWINGS

FIGS. 3C and 3D illustrate one embodiment of an EPAM hydraulic cylinder device

DETAILED DESCRIPTION OF THE PREFERRED EMBODIMENTS

The present invention is described in detail with reference to a few preferred embodiments as illustrated in the accompanying drawings. In the following description, numerous specific details are set forth in order to provide a thorough understanding of the present invention. It will be apparent, however, to one skilled in the art, that the present invention may be practiced without some or all of these specific details. In other instances, well known process steps and/or structures have not been described in detail in order to not unnecessarily obscure the present invention.

1. Electroactive Polymers

Figure 1A:
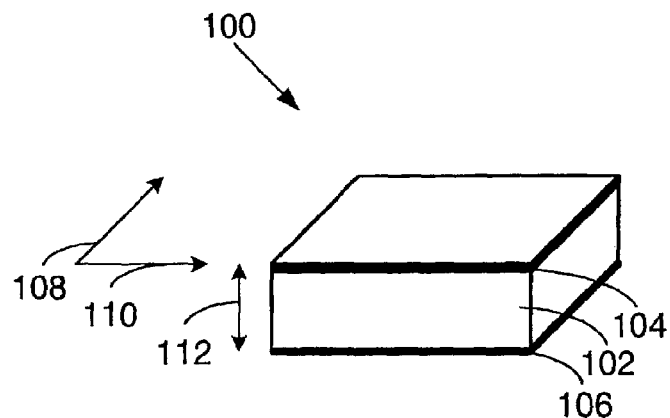
FIGS. 1A and 1B illustrate a top view of a transducer portion before and after application of a voltage, respectively, in accordance with one embodiment of the present invention.
Figure 1B:
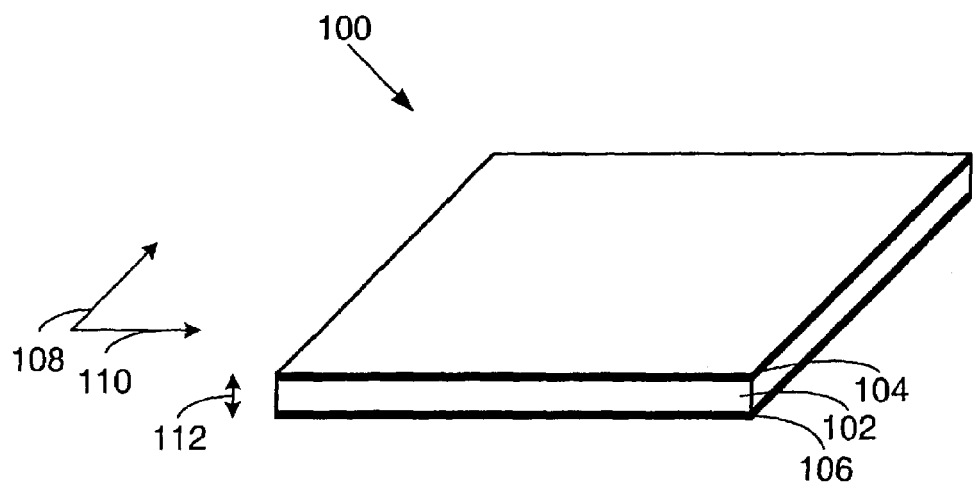

In section, before describing electroactive polymer (EPAM) devices of the present invention for performing thermodynamic work on a fluid, the basic principles of electroactive polymer construction and operation will first be illuminated in regards to FIG. 1A and FIG. 1B. In section 2, embodiments of devices and systems with EPAM transducers and their operation, such as pumps, compressors, fans and hydraulic cylinders are described with respect to FIGS. 2A–2K and 3A–3J. In section 3, embodiments of EPAM transducers of the present invention are described in regards to FIGS. 4A–4N. In section 4, sensing applications are described. In section 5, conditioning electronics of the present invention are described with respect to FIGS. 5A and 5B. In section 6, a few examples of applications such as biological applications, automobile applications and printing applications, are described.

The transformation between electrical and mechanical energy in devices of the present invention is based on energy conversion of one or more active areas of an electroactive polymer. Electroactive polymers are capable of converting between mechanical energy and electrical energy. In some cases, an electroactive polymer may change electrical properties (for example, capacitance and resistance) with changing mechanical strain.

To help illustrate the performance of an electroactive polymer in converting between electrical energy and mechanical energy, FIG. 1A illustrates a top perspective view of a transducer portion 10 in accordance with one embodiment of the present invention. The transducer portion 10 comprises a portion of an electroactive polymer 12 for converting between electrical energy and mechanical energy. In one embodiment, an electroactive polymer refers to a polymer that acts as an insulating dielectric between two electrodes and may deflect upon application of a voltage difference between the two electrodes (a 'dielectric elastomer'). Top and bottom electrodes 14 and 16 are attached to the electroactive polymer 12 on its top and bottom surfaces, respectively, to provide a voltage difference across polymer 12, or to receive electrical energy from the polymer 12. Polymer 12 may deflect with a change in electric field provided by the top and bottom electrodes 14 and 16. Deflection of the transducer portion 10 in response to a change in electric field provided by the electrodes 14 and 16 is referred to as 'actuation'. Actuation typically involves the conversion of electrical energy to mechanical energy. As polymer 12 changes in size, the deflection may be used to produce mechanical work.

Without wishing to be bound by any particular theory, in some embodiments, the polymer 12 may be considered to behave in an electrostrictive manner. The term electrostrictive is used here in a generic sense to describe the stress and strain response of a material to the square of an electric field. The term is often reserved to refer to the strain response of a material in an electric field that arises from field induced intra-molecular forces but we are using the term more generally to refer to other mechanisms that may result in a response to the square of the field. Electrostriction is distinguished from piezoelectric behavior in that the response is proportional to the square of the electric field, rather than proportional to the field. The electrostriction of a polymer with compliant electrodes may result from electrostatic forces generated between free charges on the electrodes (sometimes referred to as "Maxwell stress") and is proportional to the square of the electric field. The actual strain response in this case may be quite complicated depending on the internal and external forces on the polymer, but the electrostatic pressure and stresses are proportional to the square of the field.

FIG. 1B illustrates a top perspective view of the transducer portion 10 including deflection. In general, deflection refers to any displacement, expansion, contraction, torsion, linear or area strain, or any other deformation of a portion of the polymer 12. For actuation, a change in electric field corresponding to the voltage difference applied to or by the electrodes 14 and 16 produces mechanical pressure within polymer 12. In this case, the unlike electrical charges produced by electrodes 14 and 16 attract each other and provide a compressive force between electrodes 14 and 16 and an expansion force on polymer 12 in planar directions 18 and 20, causing polymer 12 to compress between electrodes 14 and 16 and stretch in the planar directions 18 and 20.

Electrodes 14 and 16 are compliant and change shape with polymer 12. The configuration of polymer 12 and electrodes 14 and 16 provides for increasing polymer 12 response with deflection. More specifically, as the transducer portion 10 deflects, compression of polymer 12 brings the opposite charges of electrodes 14 and 16 closer and the stretching of polymer 12 separates similar charges in each electrode. In one embodiment, one of the electrodes 14 and 16 is ground. For actuation, the transducer portion 10 generally continues to deflect until mechanical forces balance the electrostatic forces driving the deflection. The mechanical forces include elastic restoring forces of the polymer 12 material, the compliance of electrodes 14 and 16, and any external resistance provided by a device and/or load coupled to the transducer portion 10, etc. The deflection of the transducer portion 10 as a result of an applied voltage may also depend on a number of other factors such as the polymer 12 dielectric constant and the size of polymer 12.

Electroactive polymers in accordance with the present invention are capable of deflection in any direction. After application of a voltage between the electrodes 14 and 16, the electroactive polymer 12 increases in size in both planar directions 18 and 20. In some cases, the electroactive polymer 12 is incompressible, e.g. has a substantially constant volume under stress. In this case, the polymer 12 decreases in thickness as a result of the expansion in the planar directions 18 and 20. It should be noted that the present invention is not limited to incompressible polymers and deflection of the polymer 12 may not conform to such a simple relationship.

Application of a relatively large voltage difference between electrodes 14 and 16 on the transducer portion 10 shown in FIG. 1A will cause transducer portion 10 to change to a thinner, larger area shape as shown in FIG. 1B. In this manner, the transducer portion 10 converts electrical energy to mechanical energy. The transducer portion 10 may also be used to convert mechanical energy to electrical energy.

For actuation, the transducer portion 10 generally continues to deflect until mechanical forces balance the electrostatic forces driving the deflection. The mechanical forces include elastic restoring forces of the polymer 12 material, the compliance of electrodes 14 and 16, and any external resistance provided by a device and/or load coupled to the transducer portion 10, etc. The deflection of the transducer portion 10 as a result of an applied voltage may also depend on a number of other factors such as the polymer 12 dielectric constant and the size of polymer 12.

In one embodiment, electroactive polymer 12 is pre-strained. Pre-strain of a polymer may be described, in one or more directions, as the change in dimension in a direction after pre-straining relative to the dimension in that direction before pre-straining. The pre-strain may comprise elastic deformation of polymer 12 and be formed, for example, by stretching the polymer in tension and fixing one or more of the edges while stretched. Alternatively, as will be described in greater detail below, a mechanism such as a spring may be coupled to different portions of an electroactive polymer and provide a force that strains a portion of the polymer. For many polymers, pre-strain improves conversion between electrical and mechanical energy. The improved mechanical response enables greater mechanical work for an electroactive polymer, e.g., larger deflections and actuation pressures. In one embodiment, prestrain improves the dielectric strength of the polymer. In another embodiment, the pre-strain is elastic. After actuation, an elastically pre-strained polymer could, in principle, be unfixed and return to its original state.

In one embodiment, pre-strain is applied uniformly over a portion of polymer 12 to produce an isotropic pre-strained polymer. By way of example, an acrylic elastomeric polymer may be stretched by 200 to 400 percent in both planar directions. In another embodiment, pre-strain is applied unequally in different directions for a portion of polymer 12 to produce an anisotropic pre-strained polymer. In this case, polymer 12 may deflect greater in one direction than another when actuated. While not wishing to be bound by theory, it is believed that pre-straining a polymer in one direction may increase the stiffness of the polymer in the pre-strain direction. Correspondingly, the polymer is relatively stiffer in the high pre-strain direction and more compliant in the low pre-strain direction and, upon actuation, more deflection occurs in the low pre-strain direction. In one embodiment, the deflection in direction 18 of transducer portion 10 can be enhanced by exploiting large pre-strain in the perpendicular direction 20. For example, an acrylic elastomeric polymer used as the transducer portion 10 may be stretched by 10 percent in direction 18 and by 500 percent in the perpendicular direction 20. The quantity of pre-strain for a polymer may be based on the polymer material and the desired performance of the polymer in an application. Pre-strain suitable for use with the present invention is further described in commonly owned, co-pending U.S. patent application Ser. No. 09/619,848, which is incorporated by reference for all purposes.

Generally, after the polymer is pre-strained, it may be fixed to one or more objects or mechanisms. For a rigid object, the object is preferably suitably stiff to maintain the level of pre-strain desired in the polymer. A spring or other suitable mechanism that provides a force to strain the polymer may add to any prestrain previously established in the polymer before attachment to the spring or mechanisms, or may be responsible for all the prestrain in the polymer. The polymer may be fixed to the one or more objects or mechanisms according to any conventional method known in the art such as a chemical adhesive, an adhesive layer or material, mechanical attachment, etc.

Transducers and pre-strained polymers of the present invention are not limited to any particular rolled geometry or type of deflection. For example, the polymer and electrodes may be formed into any geometry or shape including tubes and multi-layer rolls, rolled polymers attached between multiple rigid structures, rolled polymers attached across a frame of any geometry—including curved or complex geometries, across a frame having one or more joints, etc. Similar structures may be used with polymers in flat sheets. Deflection of a transducer according to the present invention includes linear expansion and compression in one or more directions, bending, axial deflection when the polymer is rolled, deflection out of a hole provided on an outer cylindrical around the polymer, etc. Deflection of a transducer may be affected by how the polymer is constrained by a frame or rigid structures attached to the polymer.

Materials suitable for use as an electroactive polymer with the present invention may include any substantially insulating polymer or rubber (or combination thereof) that deforms in response to an electrostatic force or whose deformation results in a change in electric field. One suitable material is NuSil CF19-2186 as provided by NuSil Technology of Carpenteria, Calif. Other exemplary materials suitable for use as a pre-strained polymer include silicone elastomers, acrylic elastomers such as VHB 4910 acrylic elastomer as produced by 3M Corporation of St. Paul, Minn., polyurethanes, thermoplastic elastomers, copolymers comprising PVDF, pressure-sensitive adhesives, fluoroelastomers, polymers comprising silicone and acrylic moieties, and the like. Polymers comprising silicone and acrylic moieties may include copolymers comprising silicone and acrylic moieties, polymer blends comprising a silicone elastomer and an acrylic elastomer, for example. Combinations of some of these materials may also be used as the electroactive polymer in transducers of this invention.

Materials used as an electroactive polymer may be selected based on one or more material properties such as a high electrical breakdown strength, a low modulus of elasticity—(for large or small deformations), a high dielectric constant, etc. In one embodiment, the polymer is selected such that is has an elastic modulus at most about 100 MPa. In another embodiment, the polymer is selected such that is has a maximum actuation pressure between about 0.05 MPa and about 10 MPa, and preferably between about 0.3 MPa and about 3 MPa. In another embodiment, the polymer is selected such that is has a dielectric constant between about 2 and about 20, and preferably between about 2.5 and about 12. The present invention is not limited to these ranges. Ideally, materials with a higher dielectric constant than the ranges given above would be desirable if the materials had both a high dielectric constant and a high dielectric strength.

An electroactive polymer layer in transducers of the present invention may have a wide range of thicknesses. In one embodiment, polymer thickness may range between about 1 micrometer and 2 millimeters. Polymer thickness may be reduced by stretching the film in one or both planar directions. In many cases, electroactive polymers of the present invention may be fabricated and implemented as thin films. Thicknesses suitable for these thin films may be below 50 micrometers.

As electroactive polymers of the present invention may deflect at high strains, electrodes attached to the polymers should also deflect without compromising mechanical or electrical performance. Generally, electrodes suitable for use with the present invention may be of any shape and material provided that they are able to supply a suitable voltage to, or receive a suitable voltage from, an electroactive polymer. The voltage may be either constant or varying over time. In one embodiment, the electrodes adhere to a surface of the polymer. Electrodes adhering to the polymer are preferably compliant and conform to the changing shape of the polymer. Correspondingly, the present invention may include compliant electrodes that conform to the shape of an electroactive polymer to which they are attached. The electrodes may be only applied to a portion of an electroactive polymer and define an active area according to their geometry. Several examples of electrodes that only cover a portion of an electroactive polymer will be described in further detail below.

Various types of electrodes suitable for use with the present invention are described in commonly owned, co-pending U.S. patent application Ser. No. 09/619,848, which was previously incorporated by reference above. Electrodes described therein and suitable for use with the present invention include structured electrodes comprising metal traces and charge distribution layers, textured electrodes comprising varying out of plane dimensions, conductive greases such as carbon greases or silver greases, colloidal suspensions, high aspect ratio conductive materials such as carbon fibrils and carbon nanotubes, and mixtures of ionically conductive materials.

Materials used for electrodes of the present invention may vary. Suitable materials used in an electrode may include graphite, carbon black, colloidal suspensions, thin metals including silver and gold, silver filled and carbon filled gels and polymers, and ionically or electronically conductive polymers. In a specific embodiment, an electrode suitable for use with the present invention comprises 80 percent carbon grease and 20 percent carbon black in a silicone rubber binder such as Stockwell RTV60-CON as produced by Stockwell Rubber Co. Inc. of Philadelphia, Pa. The carbon grease is of the type such as NyoGel 756G as provided by Nye Lubricant Inc. of Fairhaven, Mass. The conductive grease may also be mixed with an elastomer, such as silicon elastomer RTV 118 as produced by General Electric of Waterford, N.Y., to provide a gel-like conductive grease.

It is understood that certain electrode materials may work well with particular polymers and may not work as well for others. By way of example, carbon fibrils work well with acrylic elastomer polymers while not as well with silicone polymers. For most transducers, desirable properties for the compliant electrode may include one or more of the following: low modulus of elasticity, low mechanical damping, low surface resistivity, uniform resistivity, chemical and environmental stability, chemical compatibility with the electroactive polymer, good adherence to the electroactive polymer, and the ability to form smooth surfaces. In some cases, a transducer of the present invention may implement two different types of electrodes, e.g. a different electrode type for each active area or different electrode types on opposing sides of a polymer.

2. EPAM Devices for Performing Thermodynamic Work on a Fluid

The invention describes devices for performing thermodynamic work on a fluid, such as pumps, compressors and fans (see FIGS. 2A–3J). The thermodynamic work may be used to provide a driving force for moving the fluid. Work performed on the fluid may be transmitted to other devices, such as a piston in a hydraulic actuation device (e.g., see FIGS. 3C and 3D). The devices may include one or more electroactive polymer transducers with an electroactive polymer that deflects in response to an application of an electric field (e.g., see FIGS. 1A–1B and 4A–4M). The electroactive polymer may be in contact with a fluid where the deflection of the electroactive polymer may be used to perform thermodynamic work on the fluid. The devices may be designed to efficiently operate at a plurality of operating conditions, such as operating conditions that produce an acoustic signal above or below the human hearing range. The devices may be used in thermal control systems (e.g., see FIGS. 2A–2D and 2I), such as refrigeration system, cooling systems and heating systems.

In the present invention, EPAM devices for providing thermodynamic work on a fluid are described. The laws of thermodynamics deal with interactions between a system and its surroundings. In one definition, thermodynamic work may be said to be done by a system on its surroundings if some other process can be found in which the system passes through the same series of states as in the original process, but in which the sole effect in the surroundings is the rise of a weight. For instance, a storage battery, which may be considered a system, may be discharged to light a light bulb. If the bulb were displaced by an electric motor having very large conductors and a pulley on which is wound a string suspending a weight, then the storage battery could pass through the same series of states with no net outside effect except the rise in the weight. Thus, the storage battery could be said to do thermodynamic work in the original process. When a system does work to its surrounding, then the surroundings receive the same amount of work from the system. Details of thermodynamic work by a system and in particular thermodynamic work in fluid systems are described in "The Dynamics and Thermodynamics of compressible fluid flow," by Shapiro, 1953, John Wiley and Sons, ISBN 047106691-5, which is incorporated herein in its entirety and for all purposes.

In the present invention, embodiments of EPAM devices with EPAM transducers for providing thermodynamic work on a fluid are described. The fluids of the present invention may include materials in states of a liquid, a gas, a plasma, a phase change, a solid or combinations thereof. The fluid may behave as a non-Newtonian fluid or a Newtonian fluid. Further, the fluid may be homogenous or non-homogeneous. Also, the fluid may be incompressible or compressible. Examples of fluids in the present invention include but are not limited to a gas, a plasma, a liquid, a mixture of two or more immiscible liquids, a supercritical fluid, a slurry, a suspension, and combinations thereof.

Figure 2A:
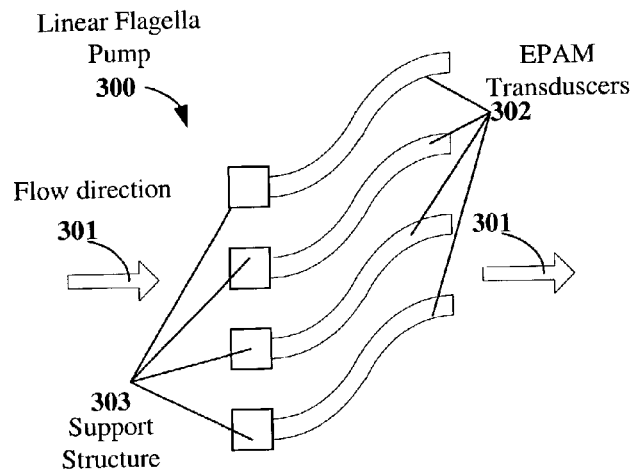
FIGS. 2A–2D illustrate Electroactive Polymer (EPAM) devices that use a flagella-like motion for performing thermodynamic work on a fluid.

FIGS. 2A–2D illustrate Electroactive Polymer (EPAM) devices that use a flagella-like motion for performing thermodynamic work on a fluid. In FIG. 2A, a linear flagella pump comprising four EPAM transducers attached to a support structure 303 are shown. The EPAM transducers 302 may be shaped in rolls as shown in FIG. 4M, or shaped in flat sheets as shown in FIGS. 4F and 4G. In general, the geometry of the EPAM transducer may be tailored to any general shape as required by the application. The EPAM transducers 302 may be controlled to perform a wave like motion from the support structure to the end of the transducers, such that a fluid moves in a generally parallel direction as indicated by the flow direction arrow 301. The bending element (such as a unimorph structure comprising a non-extensible element bonded to an electroactive polymer film with electrodes) is waved rapidly to create an air flow, similar to the way a human uses a manual fan. The wavelike motion can be amplified by operating at one of the fan's natural frequency.

The fluid may be stagnant prior to the activation of the EPAM transducers or the fluid may have an initial velocity profile. The EPAM transducers 303 may be controlled independently. For instance, the wave like motion on each transducer may be generally the same or may be different. Also, the transducers may be actuated in a time varying sequence. For instance, a wave like motion may be initiated on first pair of transducers while the other two remain inactive, followed by an initiation of a wave like motion on the other pair of transducers after the motion on the first pair of transducers is complete. The transducers may operate in phase or out of phase. In one embodiment, if the support structure 303 is unanchored, then the thermodynamic work done by the transducers on the fluid may be used to propel the support structure 303 and the transducers forward through the fluid.

Figure 2B:
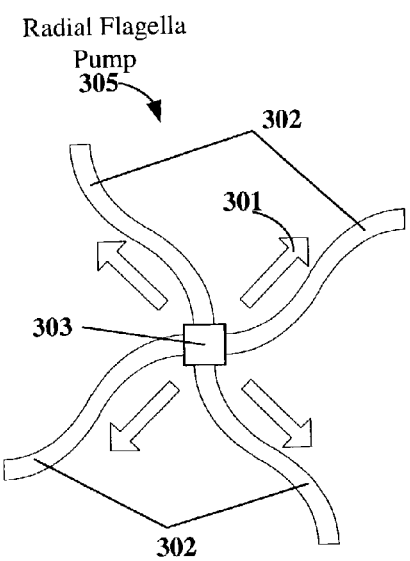
Figure 2C:
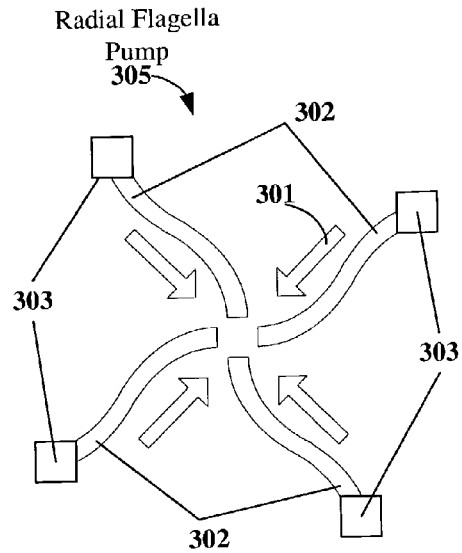

In FIGS. 2B and 2C, embodiments of radial flagella pumps are shown. Again, four EPAM transducers are attached to a support structure. The EPAM transducers may be controlled to move the fluid radially outward from the center of the support structure. For instance, if the support structures are located above a heat source, the radial motion generated by the pump 305 could be used to move a heated fluid away from the heat source.

In one embodiment, the support structure 303 may be mounted to a rotary shaft that allows the support structure 303 to rotate. In this embodiment, a motion of the transducers may be generated that provide an angular momentum to the support structure 303. In this case, the support structure and all of the transducers may start to rotate, like a fan, which may move the fluid in a direction that is proximately perpendicular to the radial motion of the direction of the fluid 301. When the transducers act as fan blades, their shape, such as their pitch, may be controlled to increase or decrease their aerodynamic efficiency. Further details of a dynamic EPAM fan blade are described with respect to FIG. 2H.

In FIG. 2C, four EPAM transducers 302 are arranged to direct a fluid radially inward to a location that is proximately central to the four transducers. For instance, the location between the four transducers may be a vent for a system, such as a vent in an enclosure for a computing system, such as a personal computer. In another embodiment, the four transducers may be used for thermal control and the location between the four transducers may be a cool spot where a warmer fluid is being directed.

In general, the EPAM devices for providing thermodynamic work of the present invention may be used as a component in a thermal control system. For instance, a plurality of the EPAM devices may be wired to a central controller, such as microcontroller or a microprocessor. The central controller may also be also connected to a plurality of sensors, such as flow rate sensors and temperature sensor. In some embodiments, the EPAM devices may also act as a sensor or part of a sensing system (see section 4). The central controller may monitor the temperature sensor and flow rate sensors and control the EPAM transducers to maintain a prescribed temperature distribution in a system that is being monitored. For instance, the system may be a fabricated article that needs to be cooled or heated with a very uniform thermal distribution to prevent thermal stresses from building inside the article during the cooling or heating process.

Figure 2D:
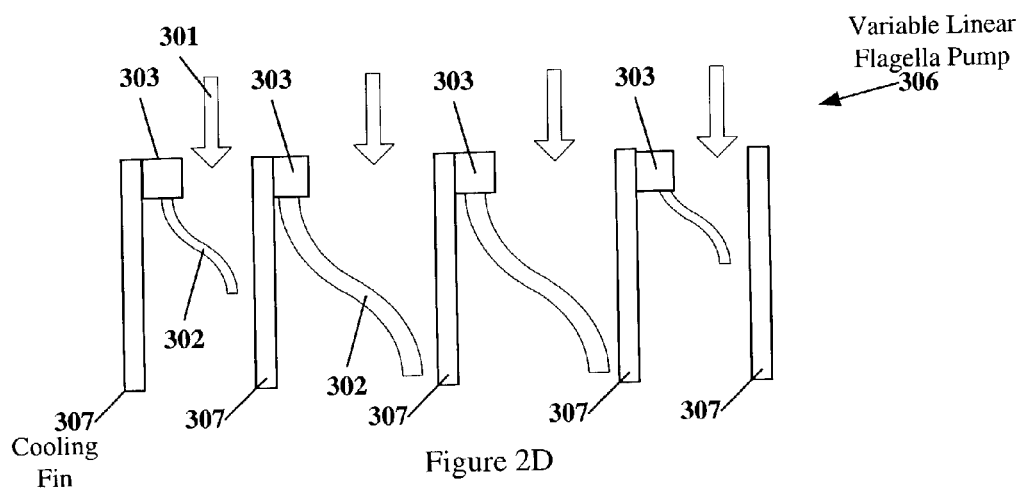

In FIG. 2D, a variable linear flagella pump is illustrated. In this embodiment, the size of the transducers is variable. The two middle transducers are larger than the two outside transducers. Thus, the flow rate in the middle may be greater than towards the outside. However, in some embodiments, this effect may also be achieved by simply moving identically shaped transducers faster or slower relative to one or another or in a different movement pattern. The transducers 302 are located next to cooling fins 307. The cooling fins may be used to conduct heat away from the fluid that is moved by the motion of the transducers 302 through the cooling fins. The cooling fins and the transducers may be part of a larger thermal control system.

In one embodiment, the transducers 302 may be used to conduct heat away from the fluid or add heat to the fluid as part of a thermal control system. For example, the transducers may be designed to conduct heat to the support structure 303. The support structure 303 may include a heat sink and a connection to a thermal conduit for removing heat from the heat sink in the support structure. The EPAM polymer may be used as a thermal conductor or thermal insulator. Thus, the material properties of the EPAM polymer in the transducer may be designed to increase or decrease the thermal conductivity of the material as required by a particular system.

In one embodiment, transducers with bending elements (i.e., flagella) of 1–20 mm may be used for microchip cooling. The EPAM transducers may be capable of large bending angles. For instance, the devices may generate over 270 degrees of bending at scales of 5–10 mm. The larger bending angle may enable a greater fluid flow for microchip cooling.

A microchip cooler using one more bending polymer fans/pumps offers a number of potential advantages. As shown in FIGS. 2A–2D, the bending fan can be easily configured in many different ways, thus allowing the fan to be optimized for the specific cooling requirements of the microchip. Polymer bending elements can be efficient at low speeds (unlike electric motors), allowing operation below acoustic frequencies and reducing or eliminating fan noise. For environments, such as home entertainment systems, low-noise may be advantageous. Bending elements also eliminate bearing noise and possible failure found in electromagnetic based microchip fans.

Figure 2E:
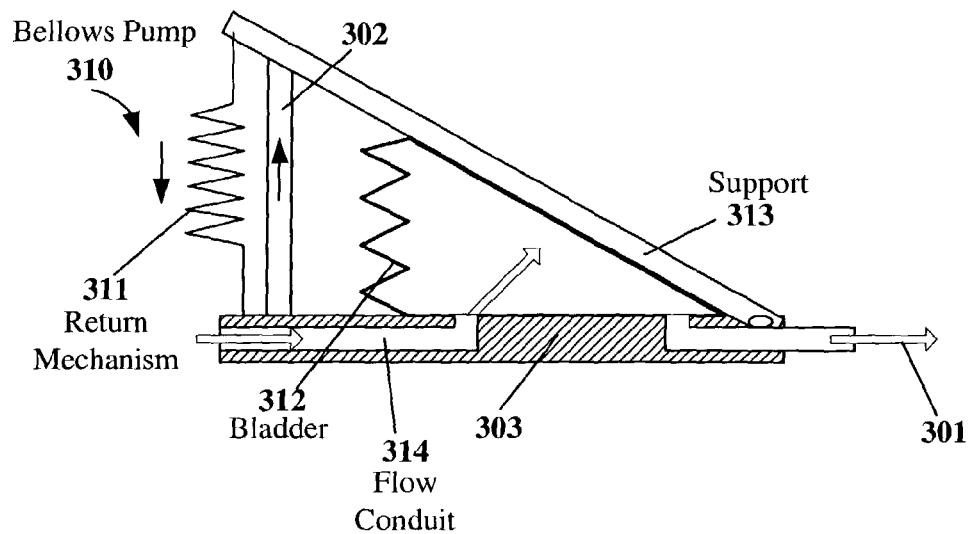
FIGS. 2E–2F illustrate Electroactive Polymer (EPAM) devices with a bellows for performing thermodynamic work on a fluid.
Figure 2F:
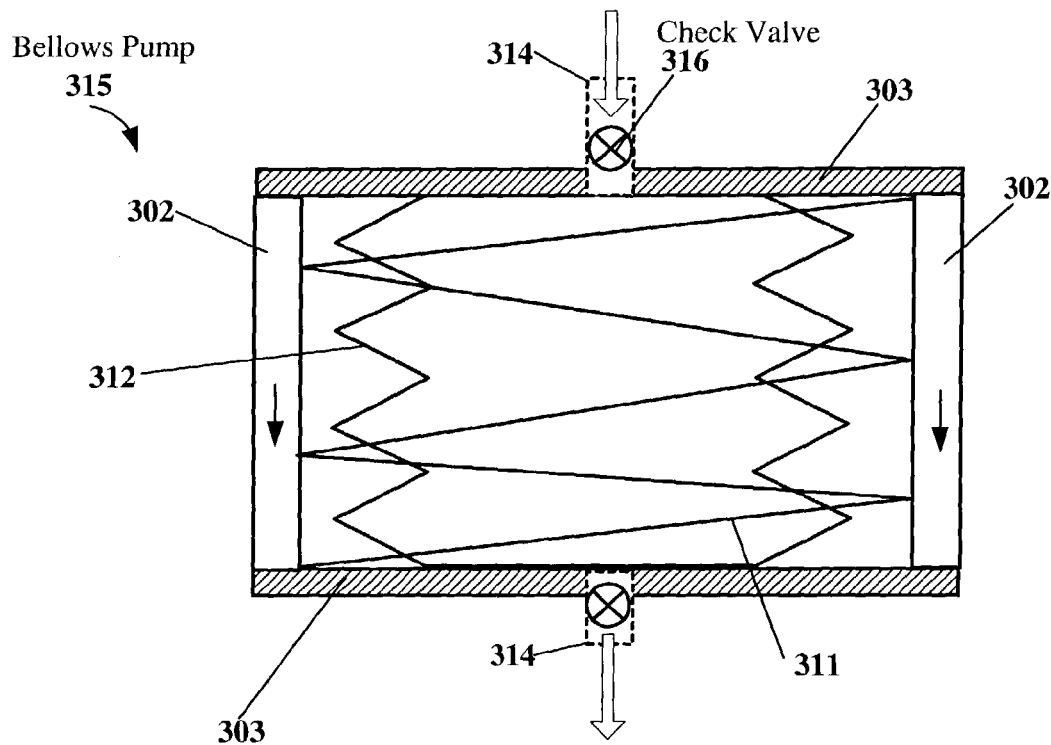

FIGS. 2E–2F illustrate Electroactive Polymer (EPAM) devices with a bellows for performing thermodynamic work on a fluid. In FIG. 2E, one embodiment of a bellows pump 310 is described. An EPAM transducer 302 is connected between a support 313 and a support structure 303 with a flow conduit. The support is attached to the support structure 303 by a linkage that allows the support 313 to pivot at a linkage point with the support structure. Between the support and the support structure is a bladder 312. Two flow conduits 314 are connected to a chamber that is bounded by the bladder 312.

When voltage is supplied to the EPAM transducer 302, the transducer extends and pushes the support 313 up and acts against a force return mechanism 311, such as a spring. The upward motion increases the volume of the bladder to draw fluid into the bladder from the flow conduit in the direction shown by the arrows. The fluid is drawn into the bladder via suction that arises from an increase in volume of the bladder. Check valves may be included in the flow conduit 314 to ensure that the fluid flows in the direction shown by the arrows. When voltage is reduced or removed from the transducer 302, the transducer 302 decreases in length, pulling the support downwards. As support is pulled downward, the bladder 312 is squeezed and fluid is expelled from the bladder and out the front of the device 310. The rate of flow out of the bladder 312 may be controlled by a rate at which voltage is decreased to the transducer 302 and by the force supplied to the support from the return mechanism 311.

FIG. 2F, a second embodiment of a bellows pump 315 is illustrated. The bellows pump includes a bladder 312 designed to fold in an accordion like manner when compressed. The bladder 312 is mounted between two support plates 303. A fluid conduit 314 passes through each of the support plates 303. The fluid conduits 314 include two check valves 316 that force the fluid to flow in the direction indicated by the arrows. The support plates are 303 are connected via a plurality of EPAM transducers 302. The bladder 312 is surrounding by a force return mechanism 311, such as a coil spring.

When energy is supplied to the EPAM transducers 302, the EPAM transducers 302 extend in length and the bladder 312 increases in volume drawing fluid into the bladder and lengthening the coil spring 311. When energy is removed or decreased to the EPAM transducers 302, the EPAM transducers contract and the support plates may be pulled together by the coil spring, reducing the volume of the bladder 312 and expelling fluid from the bladder 312 via the flow conduit. The force return mechanism (e.g., the spring) is not required and the EPAM device 315 may function without a force return mechanism. For instance, when it is stretched, mechanical forces generated in the EPAM polymer in the transducer 302 may provide a returning force when the voltage is removed or reduced on the EPAM polymer. Transducer 302 can also be a tubular transducer that completely encircles the bellows. Tubular transducers are described in more detail below. Besides a bellows pump, the present invention may be used in many types of pump designs. These pump designs include but are not limited to a centrifugal pump, a diaphragm pump, a rotary pump, a gear pump and an air-lift pump.

Figure 2G:
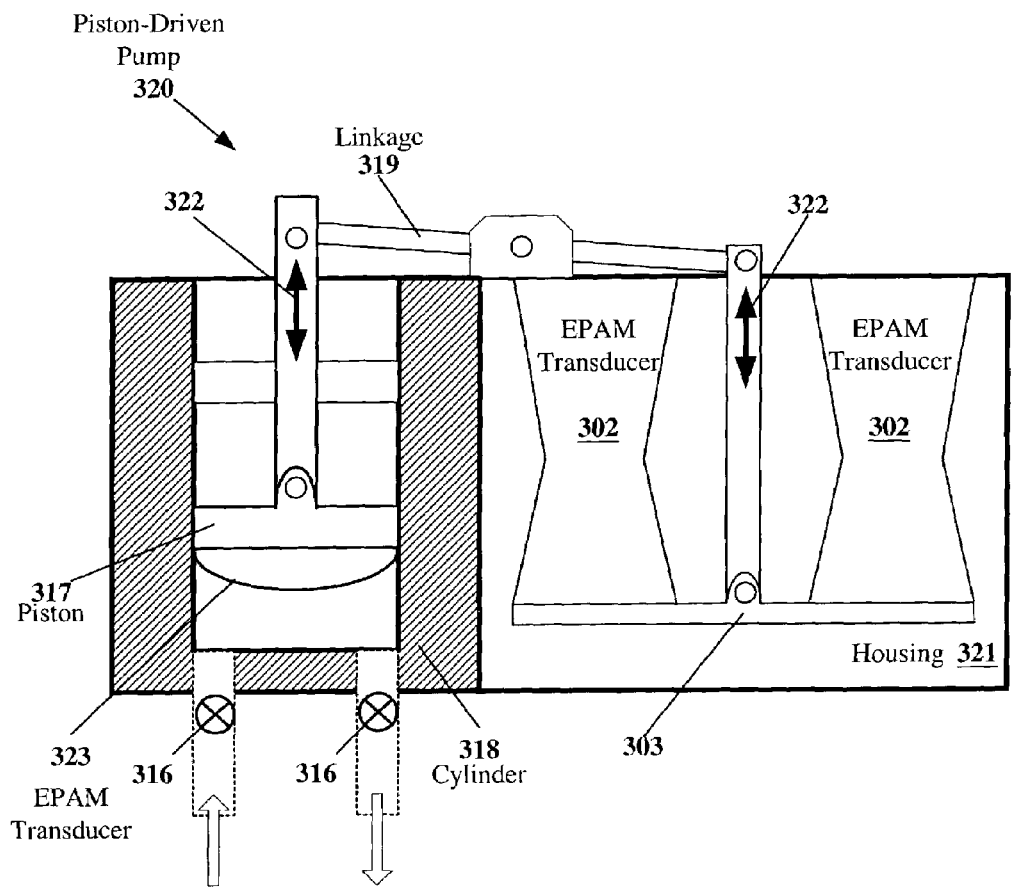
FIG. 2G illustrates an Electroactive Polymer (EPAM) device for performing thermodynamic work on a fluid with a piston driven by an EPAM transducer and an EPAM transducer for controlling a volume of the piston cylinder.

FIG. 2G illustrates an Electroactive Polymer (EPAM) device 320 for performing thermodynamic work on a fluid with a piston driven by an EPAM transducer and an EPAM transducer for controlling a volume of the piston cylinder. The piston driven pump 320 includes two fluid conduits with check valves 316 designed to limit a movement of the of the fluid to the directions of the arrow. A piston 317 is designed to move up and down 322 in a cylinder 318. When the piston moves up the volume of a pumping chamber formed by the cylinder and the piston is increased and the fluid is drawn into pumping chamber. When the piston moves downward, the volume of the pumping chamber decreases and the fluid is pushed out of the chamber.

In one embodiment of the present invention, a top surface of the piston 317 may include an EPAM transducer 323. For instance, when the piston is cylindrical, the EPAM transducer 323 may be a circular diaphragm. The EPAM transducer 323 may be deflected to change the volume of the pumping chamber. With traditional devices using pistons, the volume of the pumping chamber goes from a maximum when the piston is at the top of its stroke to minimum when the piston is at a bottom of its stroke. The maximum and minimum volumes as well as the volumes between the maximum and minimum are fixed at each location as the piston travels on its path in the cylinder. With the present invention, the EPAM transducer 323 may be deflected to allow the volume of the pumping chamber to vary at each location as the piston travels on its path in the cylinder.

By changing the volume of the pumping chamber by deflecting the EPAM transducer 323, the operating conditions of the pumping device, such as the amount of fluid pumped by the device may be changed. This effect could also be achieved by controlling the speed at which the piston operates. However, if it is advantageous to run the piston at a particular speed, such as for efficiency purposes or for noise considerations, the fluid pumping rate may be changed without changing the rate at which the piston moves by changing the volume of the pumping chamber by deflecting the EPAM transducer 323.

The piston 317 is driven by two EPAM transducers 302. The EPAM transducers 302 are connected to a housing 321 and a support structure 303. The transducers 302 may increase and decrease in length when a voltage is applied to the transducers as indicated by the direction arrows 322. Conditioning electronics and a power supply not shown (see FIGS. 5A, 5B and 6) may be used to supply power to the transducers 302. A force in the direction of motion 322 on the support structure 303 generated by the transducers 302 may be transferred by a mechanical linkage 319 to a generate the motion 322 of the piston 317 in the cylinder. There are a wide variety of mechanical linkages known in the prior art and the present invention is not limited to the example shown in FIG. 2G.

The use of the EPAM transducers to drive the piston 322 has many advantages over the use of conventional motors, such as electrical motors. One advantage is that EPAM transducers 302 are generally lighter in weight than electric motors. Another advantage is the EPAM transducers may operate efficiently at a larger number of operating conditions than an electric motor. The flexibility in operating conditions may be beneficial in regards to such issues as minimizing noise from the device 320 and controlling the devices output. For instance, the EPAM diaphragm transducers may be used to efficiently pump a fluid at an operating frequency below 30 Hz. Details of EPAM transducers used as motors and further advantages of these devices are described in co-pending U.S. application Ser. No. 10/090,430, filed on Feb. 28, 2002, by Heim, et al. and titled, "Electroactive Polymer Rotary Motors," previously incorporated herein.

In another embodiment, the piston driven pump 320 may be used as a compressor. To use the device 320 as a compressor, fluid is prevented from leaving the pumping chamber while the piston compressors the fluid in the pumping chamber is compressed by using an appropriate valve design. Details of EPAM valve designs that may be used with the piston-driven pump 320 and other embodiments of the present invention are described in co-pending U.S. application Ser. No. 10/383,005, filed on Mar. 5, 2003, by Heim, et al., and entitled, "Electroactive Polymer Devices for Controlling Fluid Flow," previously incorporated herein.

Figure 2H:
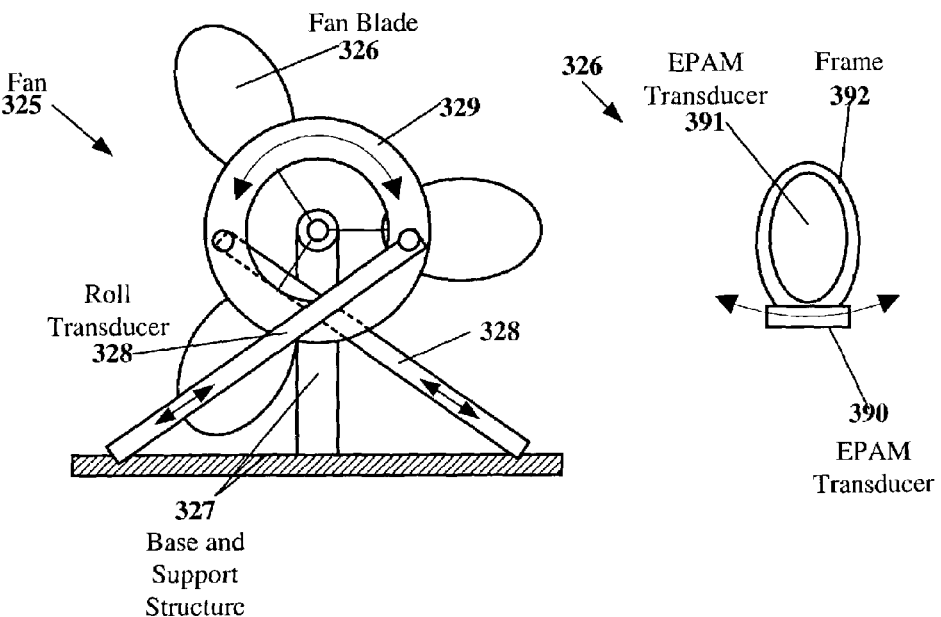
FIG. 2H illustrates an Electroactive Polymer (EPAM) device for performing thermodynamic work on a fluid with a fan driven by an EPAM transducer and an EPAM transducer for controlling a shape and attitude of the fan blades.

FIG. 2H illustrates an Electroactive Polymer (EPAM) device for performing thermodynamic work on a fluid with a fan 325 driven by an EPAM transducer 328 and an EPAM transducer for controlling a shape and attitude of the fan blades. The fan 325 includes two EPAM roll-type transducers 328 mounted to a circular plate 329 and a base 327. Other types of EPAM transducers may be used with the fan 325 and it is not limited to the use of a roll-type transducer 328 (see section 3 for further discussion of EPAM transducers). The circular plate is mounted to a support by linkage that allows the plate 329 to rotate. The support is mounted to the base 327. Three fan blades are mounted to the circular plate 329.

When a voltage is applied to the roll transducers, the transducers 328 lengthen and when the voltage is removed, the transducers contract. By supplying voltage to one of the transducers and removing or decreasing it on the opposite one, the circular plate may be made to rotate in a clock-wise or counter clock wise direction. A speed of the fan (e.g., a rotation rate of the circular plate) may be controlled by applying a time varying voltage to the transducers 328.

In one embodiment, an efficiency of the fan 325 may be controlled by changing a shape of the fan blade 326. For instance, each fan blade 391 may comprise a frame 329 with an EPAM transducer 391 with one or more active areas. The shape of the fan blade may be changed by deflecting one or more of the active areas on the EPAM transducer 391. EPAM transducers with a plurality of active areas are described with respect to FIGS. 4J–4M. The shape of the fan blade may be changed to increase or decrease its aerodynamic performance. Further, the shape of the fan blade may be changed to decrease noise and vibration emitted from the blade at a particular operating speed of the fan (aeroacoustic property) and the shape of the fan may be changed to limit or alter structural vibrational interactions within the fan blade (aeroelastic property).

The fan blade 326 may include a second EPAM transducer 390 that is designed to change a pitch of the fan blade by rotating the blade. The aerodynamic performance of the blade 326 may be a function of its pitch. In one embodiment, a single integrated EPAM transducer instead of the two transducers 391 and 392 may be used to change the shape of the blade and to change its pitch.

Figure 2I:
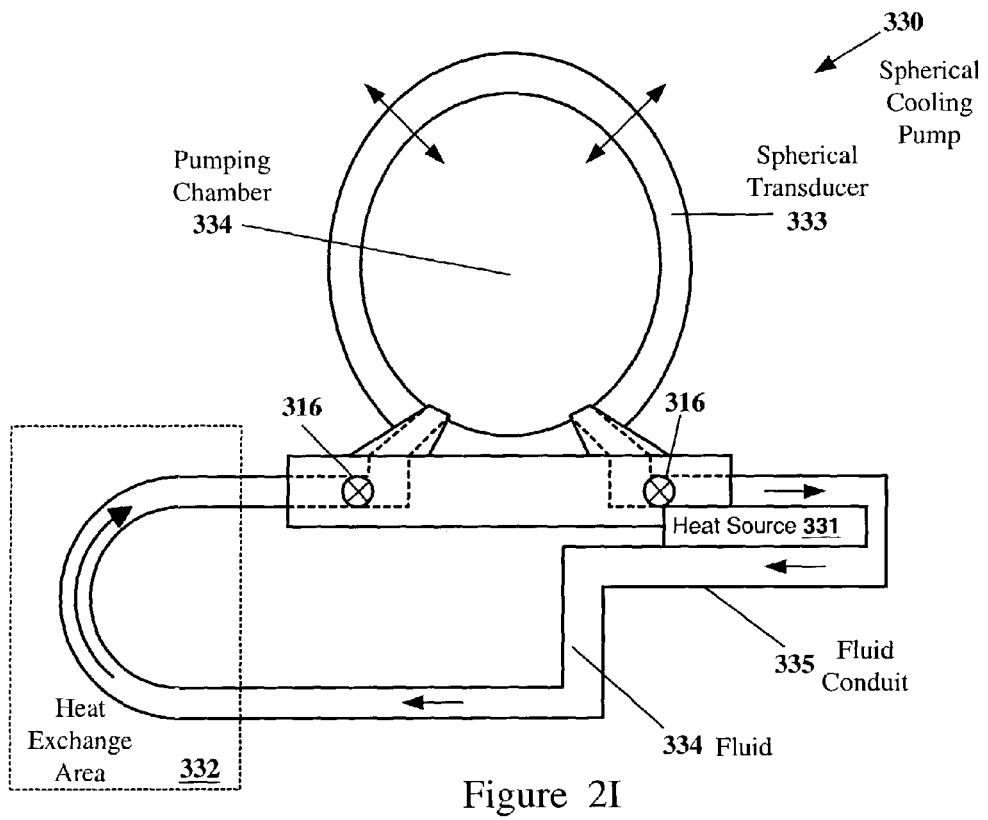
FIG. 2I illustrates an Electroactive Polymer (EPAM) spherical pumping device for circulating a cooling fluid over a heat source.

FIG. 2I illustrates an Electroactive Polymer (EPAM) spherical pumping device 330 for circulating a fluid over a heat source 331 to remove heat energy from the heat source 331. The spherical pumping device includes a spherically shaped EPAM transducer 333 that forms the bounding surface of a pumping chamber 334. The present invention is not limited to spherically shaped EPAM transducers 333 and transducers that deform into a variety general 3-D shapes may also be used.

The spherical cooling pump 330 may be part of a thermal control system for regulating a temperature of a heat source 331. In one embodiment, the heat source may be located in a computing device. For instance, the heat source may be a microprocessor. As part of the thermal control system, the spherical cooling pump 330 is connected to a closed fluid conduit 335 carrying a fluid 336. In operation, a voltage is applied to the spherical EPAM transducer 333 that causes an EPAM polymer in the transducer to deflect outwardly and a volume of the pumping chamber 334 to increase. The volume change draws the fluid 336 into the chamber. When the voltage is removed or reduced to the transducer 333, the EPAM polymer deflects inwardly forcing fluid 336 from the pumping chamber 334 into the fluid conduit 335.

In the thermal control system for the heat source 331, the fluid 336 is designed to flow past the heat source where heat energy is transferred from the heat source 331 to the fluid 336 to cool the heat source 331. The heated fluid flows from the heat source 331 to a heat exchanging area 332 where heat energy is transferred from the fluid 336. The cooled fluid may then be circulated by the spherical cooling pump 330 to pass by the heat source 331 and to pick up heat energy from the heat source.

In one embodiment, the fluid conduit 335 may include an expansion valve that induces a phase change, such as from a liquid state to a gaseous state, which is common in refrigeration systems. The phase change may be used to remove energy from the fluid 336. In another embodiment, the fluid 336 may change phase states, such as from a liquid to a gas, when the volume of the pumping chamber is expanded. The phase change may result in cooling the fluid. Further, a fluid, such as a gas, may be expanded in the pumping chamber to reduce its temperate prior to it being pumped past the heat source.

In a particular embodiment, the spherical transducer may also act as a heat exchanging area. The EPAM polymer may be designed as multi-layer structure with conducting layers used to conduct energy away from the fluid 336 in the pumping chamber 334. In other embodiments, the EPAM polymer may include an insulating layer, such in the case where the fluid 336 has been chilled prior to entering the chamber 334, to prevent the fluid from being heated by an environment surrounding the pumping chamber 334.

Figure 2J:
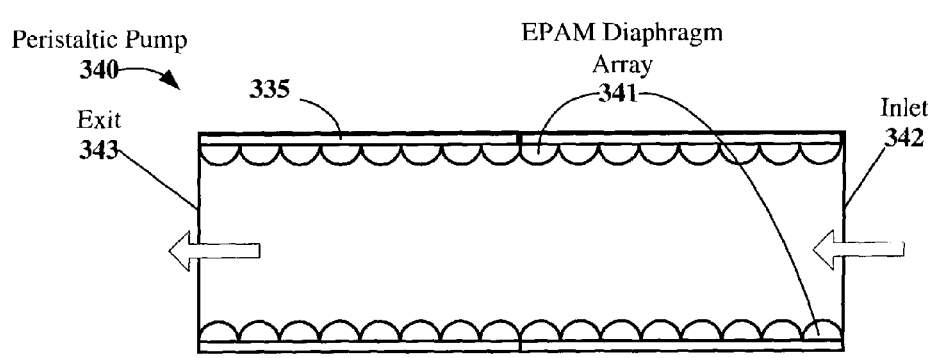
FIG. 2J illustrates one embodiment of an Electroactive Polymer (EPAM) peristaltic pumping device.

FIG. 2J illustrates one embodiment of an Electroactive Polymer (EPAM) peristaltic pumping device. The peristaltic pumping device 340 includes a fluid conduit 335 with an inlet 342 and exit 343 and a plurality of EPAM diaphragms 341 located on the inner surface of the fluid conduit 335. The diaphragms arrays may be individually controlled to generate a wave like motion, i.e., a peristaltic motion that propels fluid from the inlet 342 to the exit 343. For instance, the diaphragms may be deflected as a function of time starting from inlet 342 and progressing to the exit. This wave like motion entrains fluid towards the exit as the diaphragms are deflected in their wave pattern.

Figure 2K:
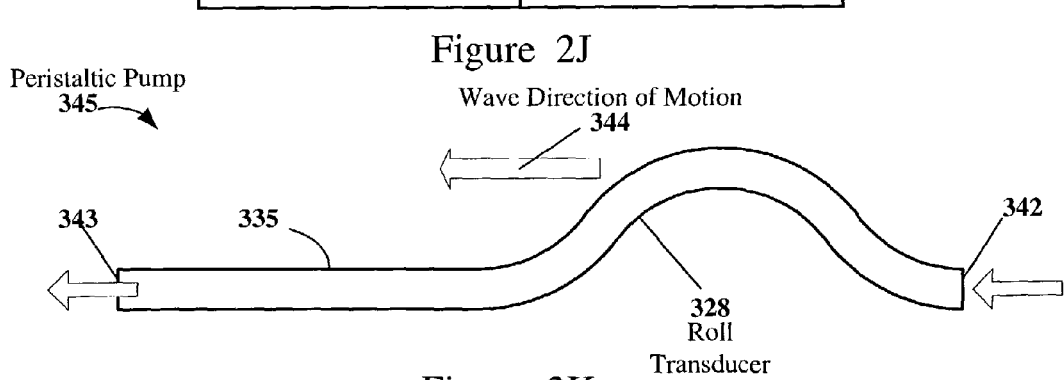
FIG. 2K illustrates one embodiment of an Electroactive Polymer (EPAM) wave motion pumping device.

FIG. 2K illustrates a second embodiment of an Electroactive Polymer (EPAM) peristaltic pumping device 345. The peristaltic pumping device 345 is comprised of a fluid conduit 335 that is a hollow EPAM roll transducer 328 (see FIGS. 4A–4E and 4K–4M). The roll transducer may be actuated to generate a wave (e.g., a hump in the transducer) that travels down the transducer in direction 344 as a function of time. As the wave moves down the transducer 328, it may push fluid ahead of it. Thus, the fluid may be moved from the inlet 342 to the exit 343. After the wave has traveled to the exit, it may be regenerated at the inlet 342 in a repeating pattern to generate continuous pumping.

In another embodiment, a diameter change, such as a narrowing in the diameter, may implemented as a wave that travels down conduit. To generate a wave, the narrow diameter may be implemented at different locations as a function of time along the conduit. As the location where the conduit is narrowed moves down conduit, fluid may be pushed a head of the location where the conduit is narrowed to produce a peristaltic pumping motion.

One advantage of the pumps described with respect to FIGS. 2I, 2J and 2K is that pumping may be performed without a separate motor. For instance, in FIGS. 2I, 2J, and 2K, the motion of the EPAM polymer used for pumping in the transducers is generated by applying a voltage from a power source, such as from a battery, to the EPAM polymer. In a traditional piston-driven pump, the motion of the piston is driven by a separate motor, such as an electric motor. The motor adds addition weight to the system. Further, motors usually are typically only efficient at a limited number of operating conditions, such as a rotational speed. Therefore, additional gearing may be required to use energy from the motor at a rate different from its optimal operating condition. Thus, the EPAM pumping devices of the present invention have a capability to be much lighter than traditional pumping systems via the elimination of a separate motor and its associated mechanical linkages.

Figure 2M:
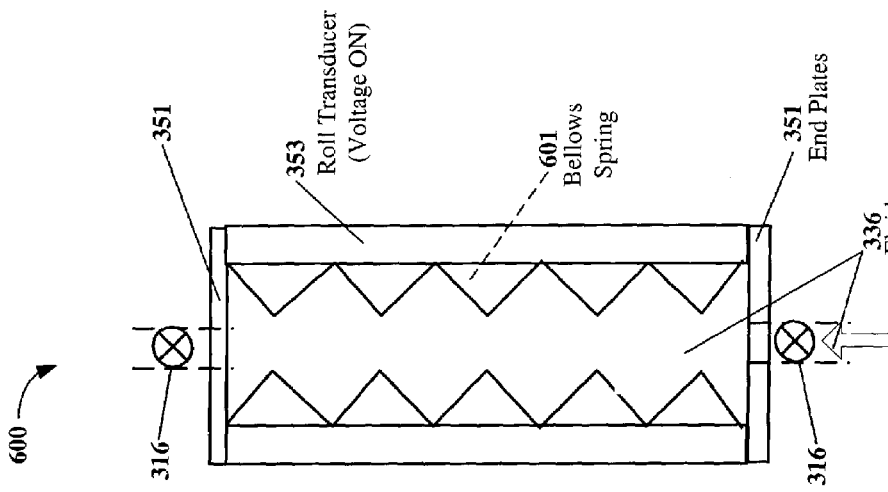
FIGS. 2L and 2M illustrate an embodiment of a bellows spring roll transducer.
Figure 2L:
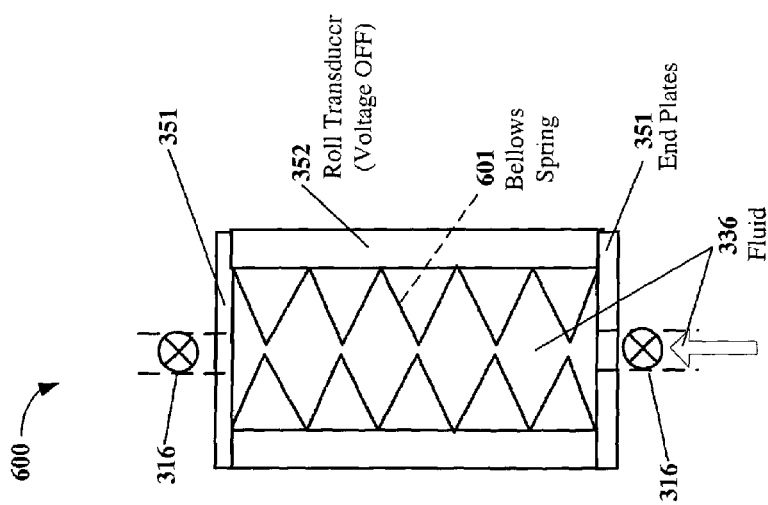

FIGS. 2L and 2M illustrate cross section of an embodiment of a bellows spring roll transducer 600. The bellows spring roll actuator 600 may be used as a pump, a valve or both. For the bellow spring roll actuator fabrication, an EPAM material, such as an acrylic film(s) may be pre-strained and rolled onto a bellows spring 601. The bellows spring 601 may form a closed chamber. The spring 601 holds the EPAM film in tension. The end structures 351 may be used to seal off the top of the bellows spring. In some embodiments, an end structure may not be required. A fluid conduit may extend through of the end structures to allow a fluid 336 to enter into the chamber formed by the bellows spring 601.

When the EPAM film is actuated in the transducer 353 the spring may expand in longitudinal length as the EPAM film lengthens and the inside diameter of the spring 601 may increase. The increase in diameter of the spring allows greater flow rate in the device if fluid is already under pressure. Thus, by adding or removing voltage from the EPAM in the transducers, the flow rate may be controlled by changing the diameter of the bellows springs 601. For pumping, check valves 316 may be added to transducer 600 as shown. When the EPAM film is unactuated the roll shortens in length and the diameter between the springs decreases. This motion may be used to force fluid out of the chamber in the bellows spring 601.

Figures 3A, 3B:
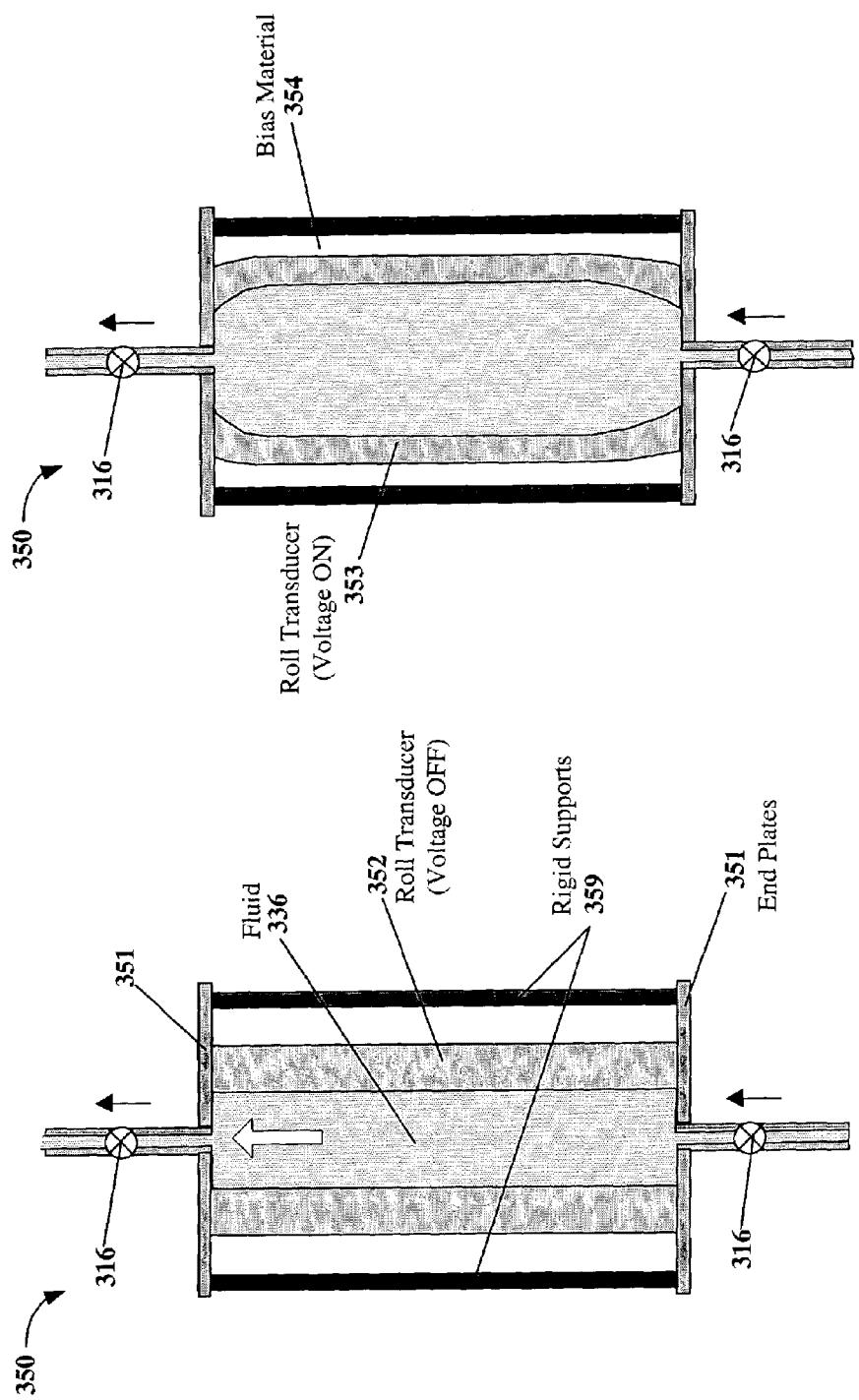
FIGS. 3A and 3B illustrate a first embodiment of an EPAM tube pumping device.

FIGS. 3A and 3B illustrate a first embodiment of an EPAM tube-type pump device 350. The tube pumping device may comprise one or more electroactive polymer transducers. The pump can be made using one or more rolls of electroactive polymer (EPAM) film arranged in a roll transducer 352. The EPAM film may or may not be pre-strained.

By way of an example, FIG. 3A shows a cross-sectional view of an EP tube-type pump 350 where a tube of electroactive polymer is attached at both ends on rigid end structures 351. The tube can be made by rolling EPAM or made directly using dip coating processes. In a preferred embodiment, the EP tube is stretched axially to provide high pre-strain in the axial direction. The forces of pre-strain are supported by rigid rods 395 attached to the end structures on the outside or inside of the tube. With high pre-strain, the diameter of the tube will be contracted in the central portion due to Poisson contraction (not shown in FIG. 3A). Two one-way (check) valves 316 are attached to the inner chamber of the tube. Alternately, the valves 316 can be actuated valves and switched at appropriate times.

In one embodiment, a tubular housing may be used instead of the rigid rods 359. Between the roll transducer 352 and the tubular housing, a partial vacuum may be generated to generate an outward bias on the roll transducer 352. In another embodiment, a bias material 352, such as foam, may be used between the tubular housing and the roll transducer 352 to generate a restoring force in a direction opposite to the direction in which the transducer expands.

In FIG. 3B, when the EPAM is actuated by applying a voltage, the EPAM film becomes thinner and expands in circumference (radially), thus allowing more fluid 336 to flow into the inner chamber through one of the one-way valves 316. In FIG. 3A, when the voltage is turned off, the EPAM film in the transducer 352 contracts in circumference and forces fluid out through the other one-way valve at a higher pressure. Thus, continuous application of the voltage allows for continuous pumping by the tube pumping device.

The pump shown FIGS. 3A and 3B can be self-priming (draws a slight vacuum relative to the outside to pull fluid in) provided the thickness and tube geometry are such that the EPAM does not buckle. Alternately, if a positive pressure fluid (relative to the external surface of the tube) is available, the positive pressure can be used to provide actuation with a circumferential pre-strain or pre-load. Or as described above, a bias pressure may be applied to the roll transducer by adding a sealed housing around the roll transducer.

Figure 3E:
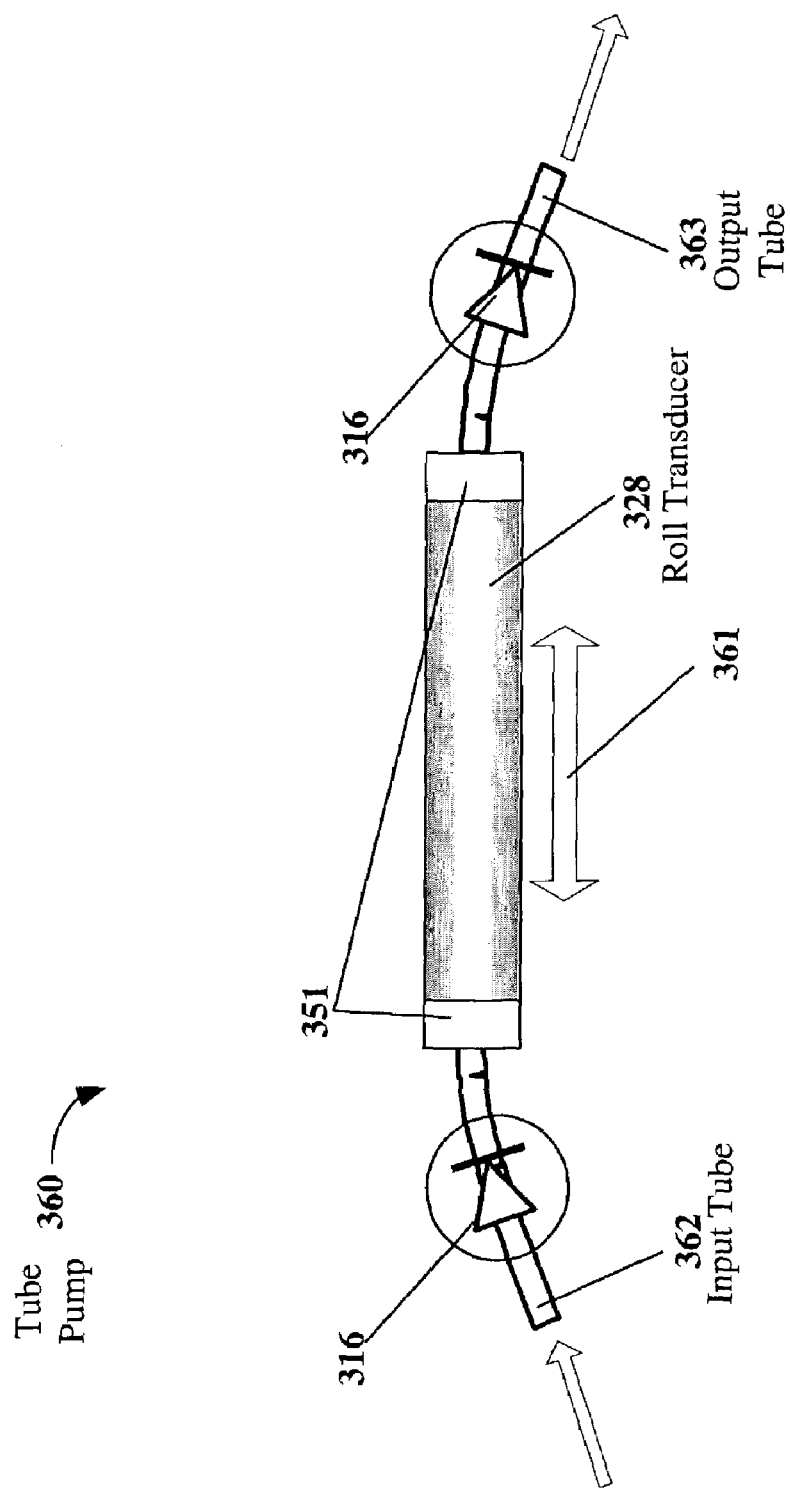
FIG. 3E illustrates a second embodiment of an EPAM tube pumping device.
Figure 3F:
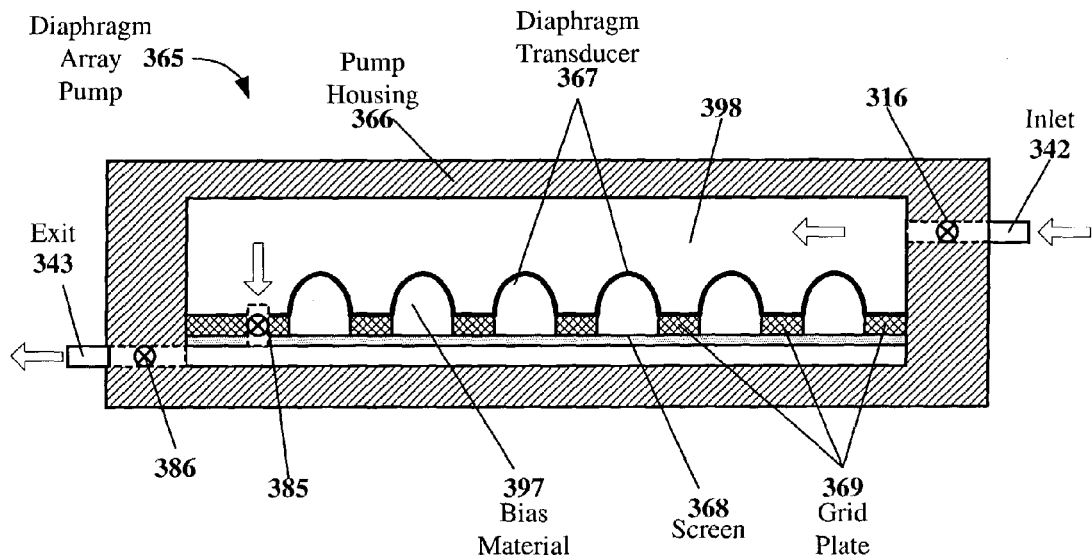
FIG. 3F illustrates an embodiment of a EPAM diaphragm array pump.
Figure 3G:
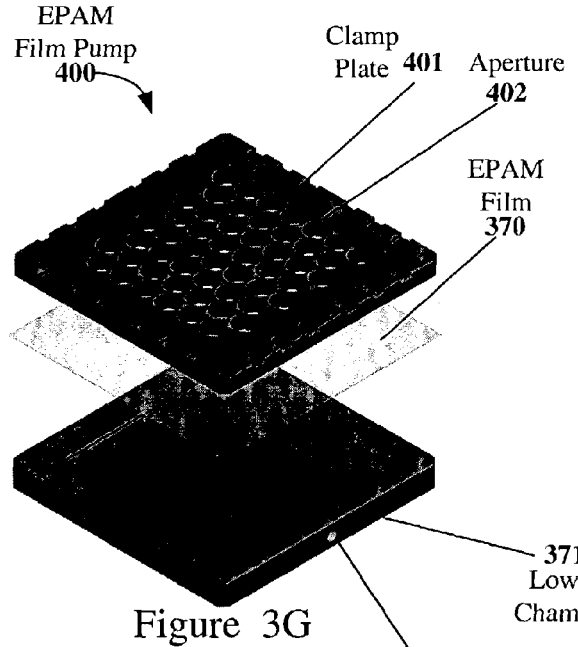
FIGS. 3G and 3H illustrate an embodiment of an EPAM film pump.
Figure 3H:
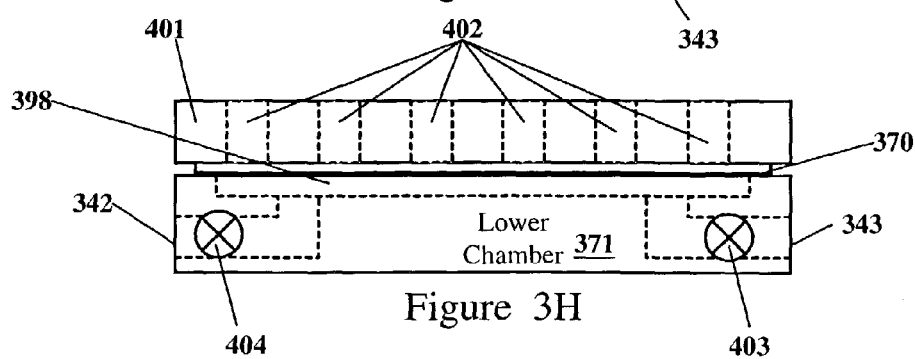
Figure 3I:
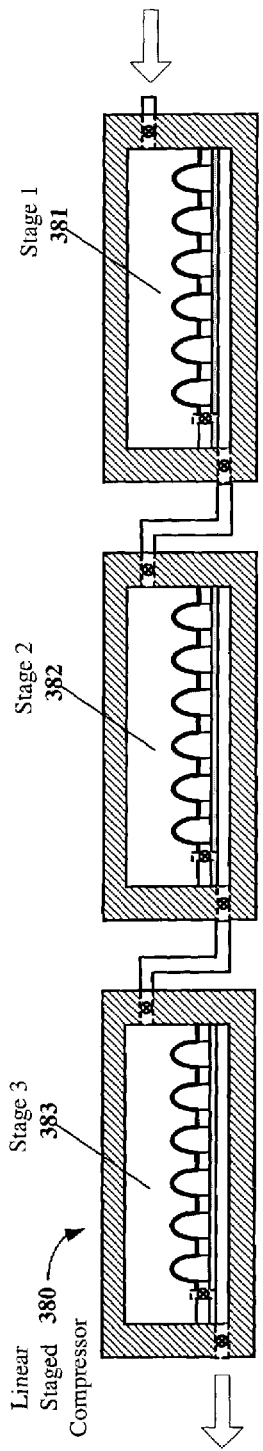
FIGS. 3I and 3J illustrate an embodiment of a multi-stage EPAM compressor or pumping device.
Figure 3J:
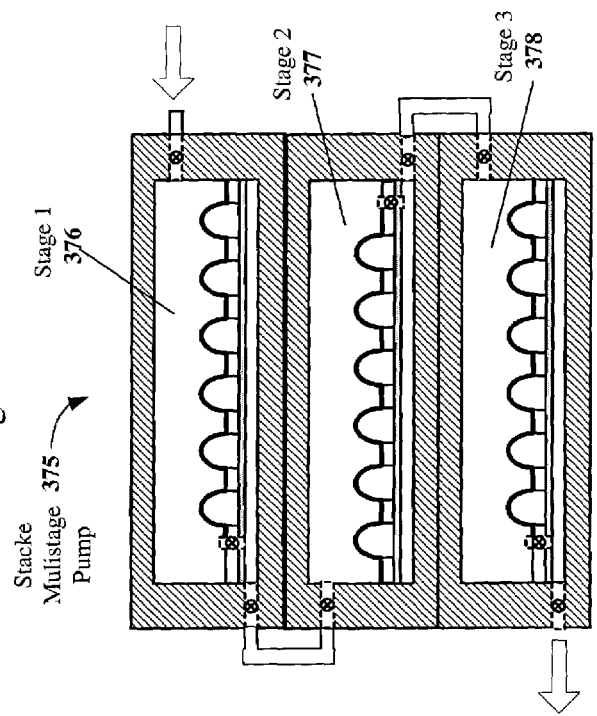

The pump 350 can be made in a cascade or series (multistage) to further increase pressure (see FIGS. 3I and 3J). For example, one could use a relatively low pressure self-priming pump to provide a positive pressure fluid to a second pump which provides higher pressures when actuated (typically 180 degrees out of phase with the first pump). The multistage pumps may be made up of elements that are connected end to end or stacked (see FIGS. 3I and 3J). Elements can also be cascaded by locating one element within another (similar to the way in which Russian dolls stack within one another). Tubular pump elements may be located concentrically within one another. The advantage of this internal or concentric cascading is that no part of a single element is exposed to the total pressure difference produced by the pump.

This embodiment provides easy fabrication of large, multilayer EPAM pumps, good coupling to EP actuation, and accommodates high pre-strain, which improves EPAM transducer performance. Also, the pump can naturally be made in a tube shape for an in-line pump with good packing geometry.

The pump in FIGS. 3A and 3B as well other pump embodiments described in the present application, may be used in many applications. For instance, the pump 350 may be used to pump fuel, such as to pump fuel in a fuel cell or fuel for combustion in a combustion chamber. The pumps may be used to move a fluid in a toy. For instance, the pump could pump fluid from a reservoir to make a doll appear to cry. The pumps may be used in refrigeration applications or as part of a thermal control system. The pumps may be used for medical applications, such as for drug delivery. For instance, in a biological application, the pump may used to deliver insulin and may include a sensor for measuring blood sugar levels so that the insulin can be delivered in a controlled manner. Other types of drugs could also be delivered in a controlled manner with an appropriate biological sensor for measuring a biologic parameter(s) of interest.

In general, the pumps can be used to transport fluid from one enclosure (e.g., a vessel, a well) to another, usually from an enclosure at a lower pressure to one at a higher pressure. In other cases, the fluid may be transported from a place at a lower potential energy to one at a higher potential energy such as delivering water uphill for irrigation. In yet other cases, pump may be used to move fluids within an open or closed structure (e.g., a pipe or an irrigation canal).

The tube geometry and the basic structure described herein can also be used to drive other devices including, for examples, linear actuators, hydraulic cylinders, and loudspeakers. For example, FIGS. 3C and 3D shows one embodiment that integrates the basic pump geometry described in FIGS. 3A and 3B to drive an internal hydraulic cylinder device 355. The hydraulic cylinder includes a roll transducer 352, end structures 351 and a cylinder between the end structures 351. The cylinder 359 and guide bearings/seal 357 may be used to guide an output shaft 356 that fits within the cylinder 359. The cylinder includes an aperture for allowing fluid 336 to flow into the cylinder. The guide bearings and seal 357 allow the output shaft to move in a smooth manner and to keep fluid within the hydraulic cylinder. The hydraulic cylinder 355 may include a force return mechanism 358 such as a spring.

When voltage is applied to the roll transducer in FIG. 3D, the roll transducer expands 353 and draws fluid 336 from the cylinder 359 and the output shaft 356 is drawn downwards. As voltage is removed from the roll transducer, fluid moves into the cylinder and pushes the output shaft upwards. The force mechanism 358 may also provide a force that moves the output shaft 356 upwards. When the voltage is off to the roll transducer 352, the output shaft is fully extended in FIG. 3C. The hydraulic cylinder via the extension of the output shaft 356 may be used to perform work on another object.

FIG. 3E illustrates a second embodiment of an EPAM tube pumping device. In this embodiment, the rigid support rods 359 in FIGS. 3A and 3B, may be replaced with one or more springs to provide axial pre-strain to the tube. The springs allow the tube to extend in length when actuated. In another embodiment, a tube-type pump comprising an electroactive polymer roll transducer may be used. The EPAM roll transducer is described in some detail with respect to FIGS. 4A–4E and 4K–4M. The EPAM roll transducers have also been described in detail in co-pending U.S. patent application Ser. No. 10/154,449 entitled "Rolled Electroactive Polymers," filed May 21, 2002, previously incorporated herein.

A pump or compressor based on the roll transducer 328 has a hole through its entire axis with appropriate hose connections on both ends (FIG. 3E). As shown in FIG. 3E, the EPAM roll transducer 328 can expand or contract axially by the application of a voltage while its diameter remains essentially unchanged. As such, the internal volume increases linearly with strain. By attaching one-way valves 316 on either end of the tube, a change in volume will impart a movement of fluid across the check valves 316 and fluid is forced to travel in one direction through the roll actuator 326. This EPAM tube-type pump provides a simple and robust design in a small package.

FIG. 3F illustrate an embodiment of a diaphragm array pump 365. The movement of the diaphragms in the transducers 367 may be used to alternately draw a fluid into a chamber and then expel it through an exit tube via one-way valves 316. The diaphragm-type EPAM transducers 367 have been described in detail in co-pending U.S. patent application Ser. No. 09/619,846, "Electroactive Polymer Devices," filed on Jul. 20, 2000; previously incorporated herein.

To influence the direction of deflection, the six diaphragm transducers 367 may be biased mechanically by one of several different means. For example, a spring-loaded plunger may be used to bias the diaphragm. In one embodiment, a spring-type design has been tested for low flow rates and pressures. The flow was approximately 40 ml/minute at about 1 kPa (Kilo-Pascal) using a single-layer electroactive polymer. The pumps may be cascaded to increase pressure above 2.5 kPa. The spring-type biasing may be suitable for low-power applications.

Other methods for biasing diaphragm-type transducers include the use of a bias material 397, such as foam, pressure (or vacuum), and a swelling agent (e.g., a small amount of silicone oil). Various means of biasing an EPAM film have been described in U.S. Pat. No. 6,343,129, "ELASTOMETRIC DIELECTRIC POLYMER FILM SONIC ACTUATOR," U.S. patent application Ser. No. 09/619,846, "Electroactive Polymer Devices," filed on Jul. 20, 2000, and U.S. patent application, Ser. No. 09/779,203, "MONOLITHIC ELECTROACTIVE POLYMERS," filed on Feb. 7, 2001; all of which are incorporated herein by reference for all purposes.

By way of an example, FIG. 3F shows a cross-sectional view of a self-priming pump comprising EPAM diaphragm transducers 367 where the EPAM diaphragms are biased using an insert of open pore foam 397. The pump 365 comprises a lower chamber 387, an upper chamber 398, a grid plate 369, six diaphragm transducers 367, three valves, 316, 385 and 396, and a screen 369 enclosed in a pump housing 366. The grid plate 369 includes apertures for accommodating the diaphragms. The screen 368 is used to hold the foam in place. In one embodiment, the foam may extend to the bottom of a lower chamber 387 and the screen may not be used.

As the EPAM diaphragms in the transducers contract, fluid is drawn through the valve 316 at the inlet 342 into a pumping chamber 398. The diaphragms then expand upon actuation which forces fluid to flow through valve 385. As the pressure builds in the area behind the diaphragms, fluid is pushed through the outlet valve 386, possibly to another stage (see FIGS. 3I and 3J).

One advantage of the configuration shown in FIG. 3F is that it is self-priming (i.e., it can pull in liquid), and it is self-priming in a way that the biasing means only needs to supply sufficient bias force to pull liquid from the top input chamber to the bottom exit chamber through the one-way valve. It does not need to supply substantial bias force, even though the power stroke of the electroactive polymer (contraction) can supply high output pressure or alternately high suction input pressure.

FIGS. 3G and 3H illustrate an embodiment of an EPAM film pump 400. FIG. 3G shows a perspective view of the pump 400 and FIG. 3H shows a cross section through the inlet 342 and outlet 343. The pump 400 may comprise a clamp plate 401 with a plurality of apertures 402 (e.g., 52 are shown in FIG. 3G) an EPAM film 370 which may be comprised of one or more layers and a lower chamber 371. The lower chamber may include an inlet 342, an outlet, check valves 403 and 404 for controlling a flow direction and fluid conduits that lead to and from a pumping chamber 398. The pumping chamber is formed by an indentation in a top of the lower chamber 371 and the EPAM film 370. The pump 400 may also include conditioning electronics and a power supply, which are not shown. The pumps shown in FIGS. 3G and 3H can use diaphragm biasing means known in the prior art, or if the inlet pressure is higher than the external ambient diaphragm pressure, then the fluid itself may be used for diaphragm biasing.

A fluid, such as air, enters through the inlet 342 in the lower chamber 371. The fluid is acted upon by the EPAM film 370 (e.g., thermodynamic work is performed on the fluid) in the pumping chamber 398, and is pushed out through a second opening in the lower chamber to exit 343. The clamp plate 401 determines the geometry of the active EPAM film. In the embodiment shown in FIGS. 3G and 3H, there are 52 openings, each with a diameter of 0.375 inches (9.53 mm), resulting in a total film active area of 5.74 in$^2$ (3700 mm$^2$). To allow fluid to pass through the chamber, there is a 1 mm gap between the film and a bottom plate of the lower chamber. The 1 mm gap is the height of the pumping chamber when the EPAM film is flat. Larger gaps may be used for pumping incompressible fluids, whereas smaller gaps minimize "dead space" when pumping compressible fluids and allow the EPAM to more effectively pressurize the compressible fluid.

In one embodiment, the clamp plate 401 and the lower chamber 371 may each measure a height of approximately 0.375 inches for a total height of 0.75 inches of the pump 400. The clamp plate and the lower chamber may measure a length of 4 inches and a width of 4 inches. Thus, a foot print area of the pumping device is 16 in$^2$. In other embodiments, the total height may be increased or decreased from 0.75 inches and the foot print area may be increased or decreased from 16 in$^2$. The clamp plate and lower chamber may serve as a housing for the device or the clamp plate and lower chamber may be enclosed in a separate housing.

One advantage of the diaphragm array pump 365 (FIG. 3F) or the EPAM film pump 400 (FIGS. 3F and 3G) is that good pumping efficiencies may be obtained for devices that are substantially flat. One measure of the flatness of a pumping device is a ratio of its height divided by the product of its foot print area. For a rectangular shaped pumping device the foot print area is the product of a length times a width of the device. For comparison purposes, a non-dimensional flatness measure may be generated by normalizing by the height of the device to obtain a flatness parameter equal to a (height)$^2$/(foot print area). For a rectangular enclosure or housing, the foot print area is a length times a width of the rectangle. For a cubic-shaped enclosure or housing, the flatness parameter generates a value of 1.

In traditional pumps, packaging requirements for a motor and for a pumping mechanism may generate a flatness parameter that approaches 1 or is greater than 1. In the present invention, the flatness parameter may be much less than 1. For instance, for one embodiment of the EPAM film pump 400 in FIGS. 3G and 3H, the height of the device is 0.75 inches and the foot print area is 16 in$^2$. Thus, the flatness parameter for this embodiment is proximately 0.035. Device for performing thermodynamic work of the present invention with a flatness parameter much less than this value are also feasible, such as less than 0.01. For devices where space is at a premium, like electronic devices such as laptop computers, the ability to produce a device for performing thermodynamic work with a small flatness parameter may be advantageous.

In some embodiments of present invention, the devices for performing thermodynamic work may be used in micro-electro-mechanical systems (MEMS). The MEMS devices may be fabricated on substrates such as silicon. For these applications, the capability of fabricating a device for performing thermodynamic work on a fluid with a small flatness parameter may be advantageous.

FIGS. 3I and 3J illustrate an embodiment of a multi-stage EPAM compressor or pumping device. For all embodiments described herein, a multiple stage (multistage) pump or compressor can be built with check valves between the stages to increase the pressure after each stage. All of the stages can be identical, although in some cases, the first stage may need a mechanical bias. For some cases, different stages may be of different sizes, have different strokes, and comprise different layers of electroactive polymer film.

In FIG. 3I, a planar configuration for linear staged compressor 380 is shown. The linear staged compressor 380 includes three stages, 381, 382 and 383, that are aligned in the same plane. The multiple stages of the compressor may be connected via one or more of a barb fitting, tubing (i.e., a fluid conduit), and a check valve.

A fluid such as air may enter stage 381 and may be pumped up to higher pressure in each stage until it exits stage 383. Each stage may be driven 180 degrees out of phase with the stage on either side (i.e., upstream and downstream). This way, as one stage is compressing, the fluid can flow into the following (downstream) stage, which is at lower pressure. Check valves may be used to prevent fluid from flowing to the previous upstream stage, such as from stage 382 to stage 381. In general, a plurality of stages may be used with the present invention and the present invention is not limited to three stages.

In FIG. 3J a stacked configuration of a multi-stage pump 375 is shown. The multi-stage pump includes three stages 376, 377 and 378, stacked one on top of the other. The stages may be identical. A low flatness parameter for each stage that is possible with the pumps of the present invention may enable stacking configurations that are not possible with conventional pumps. Fluid flows from the first stage 376 downward to stage 377 and stage 378 and then exits an outlet on stage 378. For best operation with multi-stage pumps, one generally times the stroke of one stage relative to the stroke of the next stage. For example, one might have the compression stroke of one stage coincide with the expansion stroke of the next stage. For compressible fluids such as gases being compressed to high pressures, the stroke volumes of each stage are ideally matched to the changing volume of gas (for example, if the gas is compressed to half its original volume in a many-stage pump, the last stage may only have to pump roughly half the volume per stroke as the first stage).

In the embodiments described above, the electroactive polymer devices for performing thermodynamic work on a fluid can provide many advantages over conventional pump/compressor technologies including quieter operation (elimination of a piston-based system and subsequent use of small high frequency actuators, operating at frequencies outside the human audible range), lower cost (inexpensive materials, simpler design and fewer parts than an equivalent electric motor system), and higher efficiency.

Electroactive polymers scale very well; one could design large hydraulic actuators for heavy equipment or tiny radiators for integrated circuits. The pressures required for a particular application (e.g., refrigeration or air conditioning) may be scaled up by increasing the number of layers of polymer film per stage and/or the number of stages. Unlike conventional motor-driven pumps or compressors, an electroactive polymer pump can be driven at frequencies above or below the audible range.

3. Electroactive Polymer Devices 3.1 Transducers

Figure 4A:
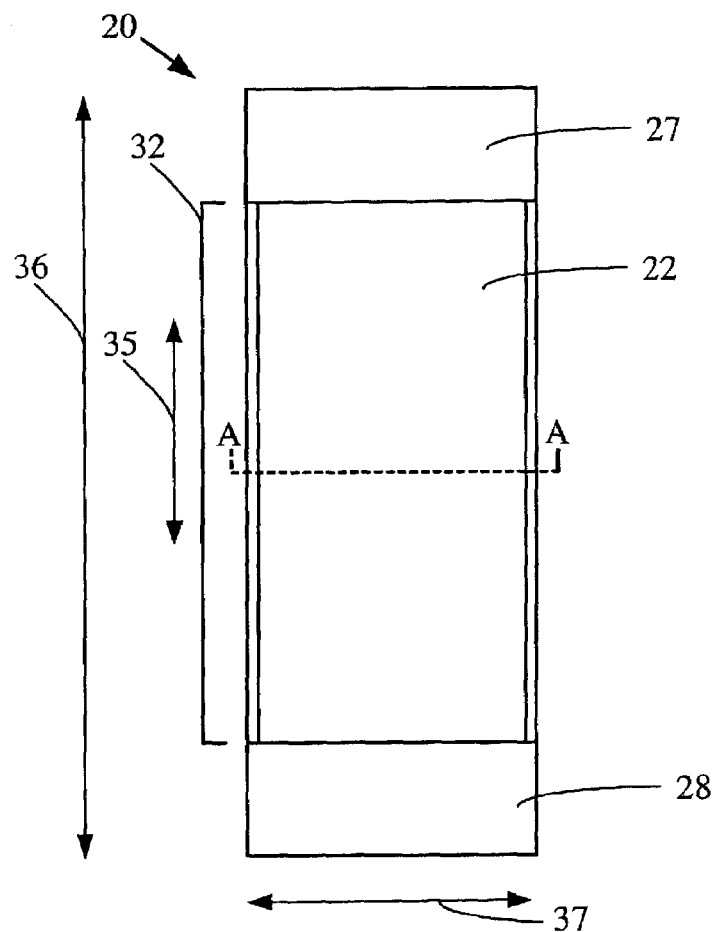
FIGS. 4A–4D illustrate a rolled electroactive polymer device in accordance with one embodiment of the present invention.
Figure 4B:
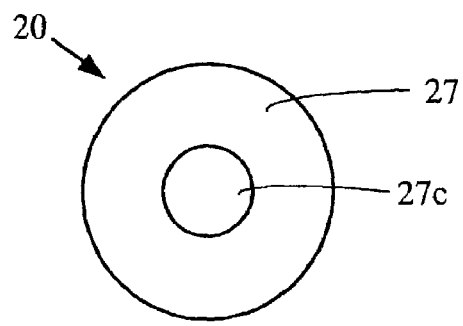
Figure 4C:
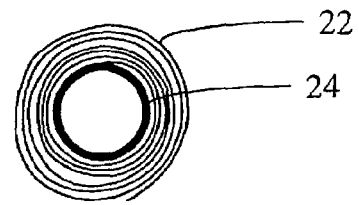
Figure 4D:
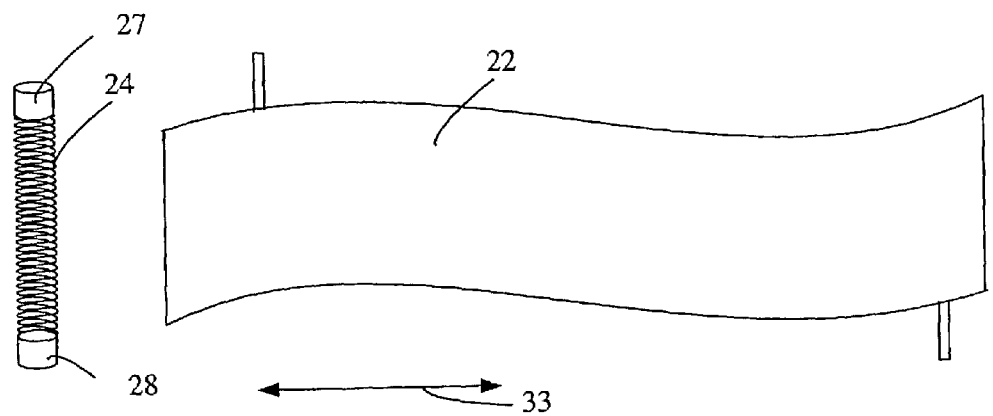

FIGS. 4A–2E show a rolled electroactive polymer device 20 in accordance with one embodiment of the present invention. The rolled electroactive polymer device may be used for actuation in EPAM devices for performing thermodynamic work on a fluid and may also act as part of a fluid conduit or other types of structures immersed in an external or internal flowfield that is used with the devices for performing thermodynamic work. The rolled electroactive polymer devices may provide linear and/or rotational/torsional motion for operating the EPAM devices. For instance, see the fan embodiment in FIG. 2H. FIG. 4A illustrates a side view of device 20. FIG. 4B illustrates an axial view of device 20 from the top end. FIG. 4C illustrates an axial view of device 20 taken through cross section A—A. FIG. 4D illustrates components of device 20 before rolling. Device 20 comprises a rolled electroactive polymer 22, spring 24, end pieces 27 and 28, and various fabrication components used to hold device 20 together.

As illustrated in FIG. 4C, electroactive polymer 22 is rolled. In one embodiment, a rolled electroactive polymer refers to an electroactive polymer with, or without electrodes, wrapped round and round onto itself (e.g., like a poster) or wrapped around another object (e.g., spring 24). The polymer may be wound repeatedly and at the very least comprises an outer layer portion of the polymer overlapping at least an inner layer portion of the polymer. In one embodiment, a rolled electroactive polymer refers to a spirally wound electroactive polymer wrapped around an object or center. As the term is used herein, rolled is independent of how the polymer achieves its rolled configuration.

As illustrated by FIGS. 4C and 4D, electroactive polymer 22 is rolled around the outside of spring 24. Spring 24 provides a force that strains at least a portion of polymer 22. The top end 24a of spring 24 is attached to rigid endpiece 27. Likewise, the bottom end 24b of spring 24 is attached to rigid endpiece 28. The top edge 22a of polymer 22 (FIG. 4D) is wound about endpiece 27 and attached thereto using a suitable adhesive. The bottom edge 22b of polymer 22 is wound about endpiece 28 and attached thereto using an adhesive. Thus, the top end 24a of spring 24 is operably coupled to the top edge 22a of polymer 22 in that deflection of top end 24a corresponds to deflection of the top edge 22a of polymer 22. Likewise, the bottom end 24b of spring 24 is operably coupled to the bottom edge 22b of polymer 22 and deflection bottom end 24b corresponds to deflection of the bottom edge 22b of polymer 22. Polymer 22 and spring 24 are capable of deflection between their respective bottom top portions.

As mentioned above, many electroactive polymers perform better when prestrained. For example, some polymers exhibit a higher breakdown electric field strength, electrically actuated strain, and energy density when prestrained. Spring 24 of device 20 provides forces that result in both circumferential and axial prestrain onto polymer 22.

Spring 24 is a compression spring that provides an outward force in opposing axial directions (FIG. 4A) that axially stretches polymer 22 and strains polymer 22 in an axial direction. Thus, spring 24 holds polymer 22 in tension in axial direction 35. In one embodiment, polymer 22 has an axial prestrain in direction 35 from about 50 to about 300 percent. As will be described in further detail below for fabrication, device 20 may be fabricated by rolling a prestrained electroactive polymer film around spring 24 while it the spring is compressed. Once released, spring 24 holds the polymer 22 in tensile strain to achieve axial prestrain.

Spring 24 also maintains circumferential prestrain on polymer 22. The prestrain may be established in polymer 22 longitudinally in direction 33 (FIG. 4D) before the polymer is rolled about spring 24. Techniques to establish prestrain in this direction during fabrication will be described in greater detail below. Fixing or securing the polymer after rolling, along with the substantially constant outer dimensions for spring 24, maintains the circumferential prestrain about spring 24. In one embodiment, polymer 22 has a circumferential prestrain from about 100 to about 500 percent. In many cases, spring 24 provides forces that result in anisotropic prestrain on polymer 22.

Figure 4E:
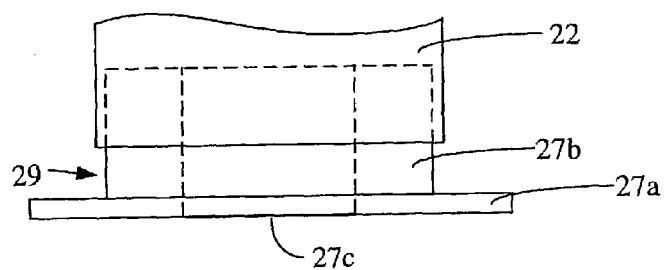
FIG. 4E illustrates an end piece for the rolled electroactive polymer device of FIG. 2A in accordance with one embodiment of the present invention.
Figure 4F:
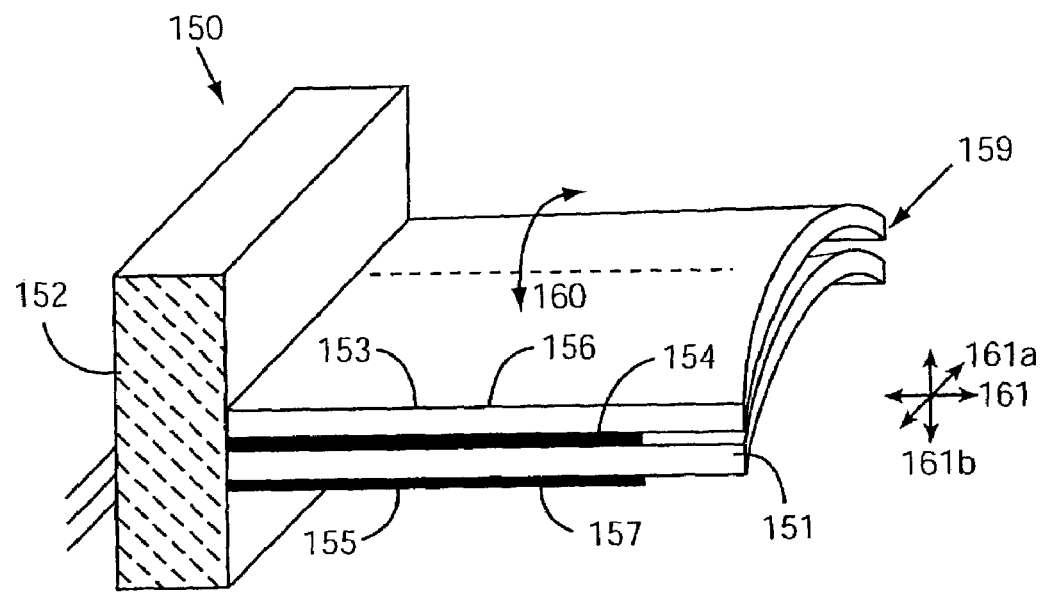
FIG. 4F illustrates a bending transducer for providing variable stiffness based on structural changes related to polymer deflection in accordance with one embodiment of the present invention.
Figure 4G:
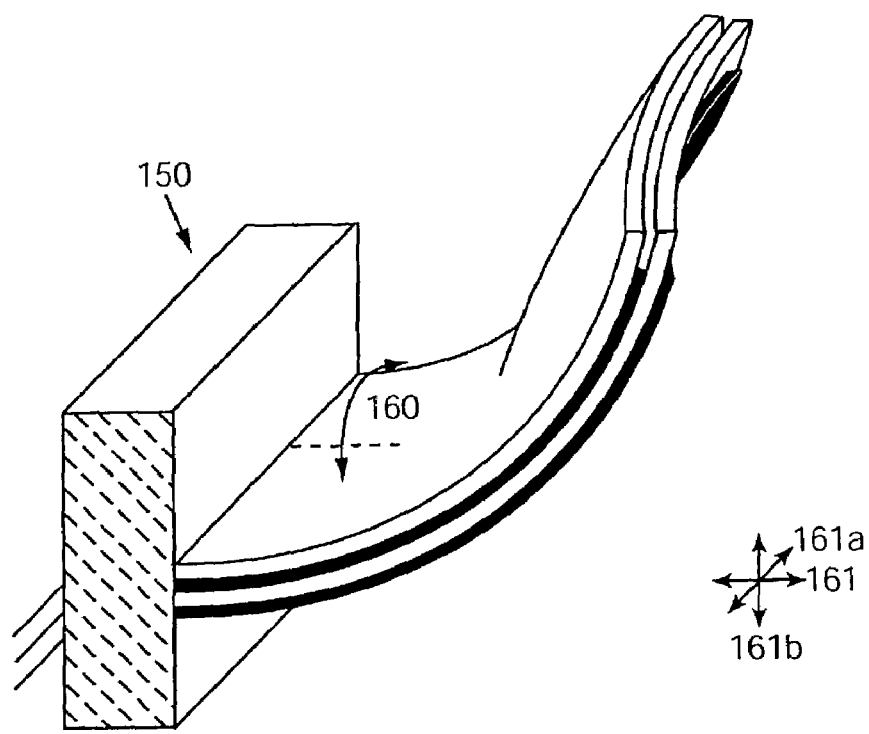
FIG. 4G illustrates the transducer of FIG. 4A with a 90 degree bending angle.

End pieces 27 and 28 are attached to opposite ends of rolled electroactive polymer 22 and spring 24. FIG. 4E illustrates a side view of end piece 27 in accordance with one embodiment of the present invention. Endpiece 27 is a circular structure that comprises an outer flange 27a, an interface portion 27b, and an inner hole 27c. Interface portion 27b preferably has the same outer diameter as spring 24. The edges of interface portion 27b may also be rounded to prevent polymer damage. Inner hole 27c is circular and passes through the center of endpiece 27, from the top end to the bottom outer end that includes outer flange 27a. In a specific embodiment, endpiece 27 comprises aluminum, magnesium or another machine metal. Inner hole 27c is defined by a hole machined or similarly fabricated within endpiece 27. In a specific embodiment, endpiece 27 comprises ½ inch end caps with a ⅜ inch inner hole 27c.

In one embodiment, polymer 22 does not extend all the way to outer flange 27a and a gap 29 is left between the outer portion edge of polymer 22 and the inside surface of outer flange 27a. As will be described in further detail below, an adhesive or glue may be added to the rolled electroactive polymer device to maintain its rolled configuration. Gap 29 provides a dedicated space on endpiece 27 for an adhesive or glue than the buildup to the outer diameter of the rolled device and fix to all polymer layers in the roll to endpiece 27. In a specific embodiment, gap 29 is between about 0 mm and about 5 mm.

The portions of electroactive polymer 22 and spring 24 between end pieces 27 and 28 may be considered active to their functional purposes. Thus, end pieces 27 and 28 define an active region 32 of device 20 (FIG. 4A). End pieces 27 and 28 provide a common structure for attachment with spring 24 and with polymer 22. In addition, each end piece 27 and 28 permits external mechanical and detachable coupling to device 20. For example, device 20 may be employed in a robotic application where endpiece 27 is attached to an upstream link in a robot and endpiece 28 is attached to a downstream link in the robot. Actuation of electroactive polymer 22 then moves the downstream link relative to the upstream link as determined by the degree of freedom between the two links (e.g., rotation of link 2 about a pin joint on link 1).

In a specific embodiment, inner hole 27c comprises an internal thread capable of threaded interface with a threaded member, such as a screw or threaded bolt. The internal thread permits detachable mechanical attachment to one end of device 20. For example, a screw may be threaded into the internal thread within end piece 27 for external attachment to a robotic element. For detachable mechanical attachment internal to device 20, a nut or bolt to be threaded into each end piece 27 and 28 and pass through the axial core of spring 24, thereby fixing the two end pieces 27 and 28 to each other. This allows device 20 to be held in any state of deflection, such as a fully compressed state useful during rolling. This may also be useful during storage of device 20 so that polymer 22 is not strained in storage.

In one embodiment, a stiff member or linear guide 30 is disposed within the spring core of spring 24. Since the polymer 22 in spring 24 is substantially compliant between end pieces 27 and 28, device 20 allows for both axial deflection along direction 35 and bending of polymer 22 and spring 24 away from its linear axis (the axis passing through the center of spring 24). In some embodiments, only axial deflection is desired. Linear guide 30 prevents bending of device 20 between end pieces 27 and 28 about the linear axis. Preferably, linear guide 30 does not interfere with the axial deflection of device 20. For example, linear guide 30 preferably does not introduce frictional resistance between itself and any portion of spring 24. With linear guide 30, or any other suitable constraint that prevents motion outside of axial direction 35, device 20 may act as a linear actuator or generator with output strictly in direction 35. Linear guide 30 may be comprised of any suitably stiff material such as wood, plastic, metal, etc.

Polymer 22 is wound repeatedly about spring 22. For single electroactive polymer layer construction, a rolled electroactive polymer of the present invention may comprise between about 2 and about 200 layers. In this case, a layer refers to the number of polymer films or sheets encountered in a radial cross-section of a rolled polymer. In some cases, a rolled polymer comprises between about 5 and about 100 layers. In a specific embodiment, a rolled electroactive polymer comprises between about 15 and about 50 layers.

In another embodiment, a rolled electroactive polymer employs a multilayer structure. The multilayer structure comprises multiple polymer layers disposed on each other before rolling or winding. For example, a second electroactive polymer layer, without electrodes patterned thereon, may be disposed on an electroactive polymer having electrodes patterned on both sides. The electrode immediately between the two polymers services both polymer surfaces in immediate contact. After rolling, the electrode on the bottom side of the electroded polymer then contacts the top side of the non-electroded polymer. In this manner, the second electroactive polymer with no electrodes patterned thereon uses the two electrodes on the first electroded polymer.

Other multilayer constructions are possible. For example, a multilayer construction may comprise any even number of polymer layers in which the odd number polymer layers are electroded and the even number polymer layers are not. The upper surface of the top non-electroded polymer then relies on the electrode on the bottom of the stack after rolling. Multilayer constructions having 2, 4, 6, 8, etc., are possible this technique. In some cases, the number of layers used in a multilayer construction may be limited by the dimensions of the roll and thickness of polymer layers. As the roll radius decreases, the number of permissible layers typically decrease is well. Regardless of the number of layers used, the rolled transducer is configured such that a given polarity electrode does not touch an electrode of opposite polarity. In one embodiment, multiple layers are each individually electroded and every other polymer layer is flipped before rolling such that electrodes in contact each other after rolling are of a similar voltage or polarity.

The multilayer polymer stack may also comprise more than one type of polymer For example, one or more layers of a second polymer may be used to modify the elasticity or stiffness of the rolled electroactive polymer layers. This polymer may or may not be active in the charging/discharging during the actuation. When a non-active polymer layer is employed, the number of polymer layers may be odd. The second polymer may also be another type of electroactive polymer that varies the performance of the rolled product.

In one embodiment, the outermost layer of a rolled electroactive polymer does not comprise an electrode disposed thereon. This may be done to provide a layer of mechanical protection, or to electrically isolate electrodes on the next inner layer. For example, inner and outer layers and surface coating may be selected to provide fluid compatibility as previously described. The multiple layer characteristics described above may also be applied non-rolled electroactive polymers, such as EPAM diaphragms previously described.

Device 20 provides a compact electroactive polymer device structure and improves overall electroactive polymer device performance over conventional electroactive polymer devices. For example, the multilayer structure of device 20 modulates the overall spring constant of the device relative to each of the individual polymer layers. In addition, the increased stiffness of the device achieved via spring 24 increases the stiffness of device 20 and allows for faster response in actuation, if desired.

In a specific embodiment, spring 24 is a compression spring such as catalog number 11422 as provided by Century Spring of Los Angeles, Calif. This spring is characterized by a spring force of 0.91 lb/inch and dimensions of 4.38 inch free length, 1.17 inch solid length, 0.360 inch outside diameter, 0.3 inch inside diameter. In this case, rolled electroactive polymer device 20 has a height 36 from about 5 to about 7 cm, a diameter 37 of about 0.8 to about 1.2 cm, and an active region between end pieces of about 4 to about 5 cm. The polymer is characterized by a circumferential prestrain from about 300 to about 500 percent and axial prestrain (including force contributions by spring 24) from about 150 to about 250 percent.

Although device 20 is illustrated with a single spring 24 disposed internal to the rolled polymer, it is understood that additional structures such as another spring external to the polymer may also be used to provide strain and prestrain forces. These external structures may be attached to device 20 using end pieces 27 and 28 for example.

FIG. 4F illustrates a bending transducer 150 for providing variable stiffness based on structural changes in accordance with one embodiment of the present invention. In this case, transducer 150 varies and controls stiffness in one direction using polymer deflection in another direction. In one embodiment, the bending transducer may be used to provide a driving force to a fluid (see FIGS. 2A–2D). Transducer 150 includes a polymer 151 fixed at one end by a rigid support 152. Attached to polymer 151 is a flexible thin material 153 such as polyimide or mylar using an adhesive layer, for example. The flexible thin material 153 has a modulus of elasticity greater than polymer 151. The difference in modulus of elasticity for the top and bottom sides 156 and 157 of transducer 150 causes the transducer to bend upon actuation. Electrodes 154 and 155 are attached to the opposite sides of the polymer 151 to provide electrical communication between polymer 151 and control electronics used to control transducer 150 deflection. Transducer 150 is not planar but rather has a slight curvature about axis 160 as shown. Direction 160 is defined as rotation or bending about a line extending axially from rigid support 152 through polymer 151. This curvature makes transducer 150 stiff in response to forces applied to the tip along any of the directions indicated by the arrows 161. In place of, or in addiction to forces, torques may be applied to the transducer. These torques may be applied about the axis indicated by the arrows of directions 161a and 161b.

FIG. 4G illustrates transducer 150 with a deflection in direction 161b that is caused by the application of a voltage to he electrodes 154 and 155. The voltage is applied to allow the bending forces to overcome the resistance presented by the curvature in the unactuated state. Effectively, the transducer 152 bends with a kink caused by the initial curvature. In this state, the stiffness in response to the forces or torques indicated by directions 161 is much less.

A mechanical interface may be attached to the distal portion 159 of transducer 150. Alternately, mechanical attachment may be made to the flexible thin material 153 to allow transducer 150 implementation in a mechanical device. For example, transducer 150 is well suited for use in applications such as lightweight space structures where folding of the structure, so that it can be stowed and deployed, is useful. In this example, the stiff condition of individual transducers (which form ribs in the structure) occurs when the structure is deployed. To allow for stowing, the transducers are actuated and the ribs may be bent. In another application, the transducers form ribs in the sidewall of pneumatic tires. In this application, the change in the stiffness of the ribs can affect the stiffness of the tires and thus the resultant handling of the vehicle that uses the tires. Similarly, the device may be implemented in a shoe and the change in stiffness of the ribs can affect the stiffness of the shoe.

Transducer 150 provides one example where actuation of an electroactive polymer causes low-energy changes in configuration or shape that affects stiffness of a device. Using this technique, it is indeed possible to vary stiffness using transducer 150 at greater levels than direct mechanical or electrical energy control. In another embodiment, deflection of an electroactive polymer transducer directly contributes to the changing stiffness of a device that the transducer is configured within.

Figure 4H:
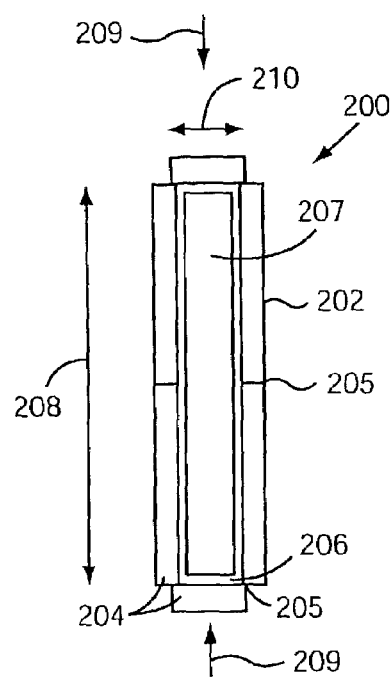
FIG. 4H illustrates a bow device suitable for providing variable stiffness in accordance with another embodiment of the present invention.
Figure 4I:
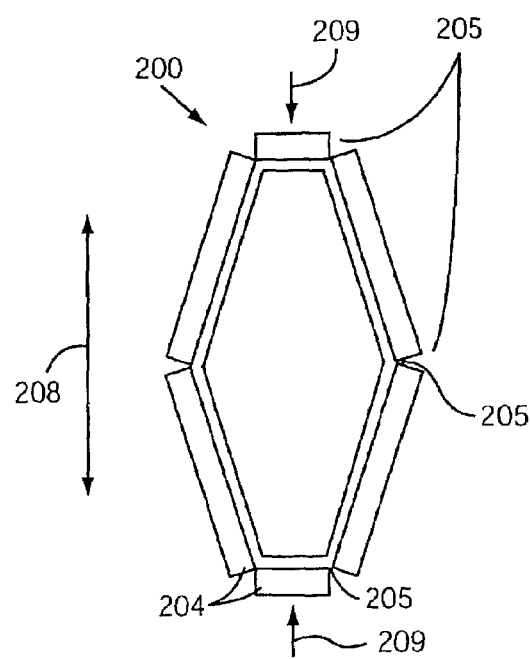
FIG. 4I illustrates the bow device of FIG. 4C after actuation.

FIG. 4H illustrates a bow device 200 suitable for providing variable stiffness in accordance with another embodiment of the present invention. Bow device 200 is a planar mechanism comprising a flexible frame 202 attached to a polymer 206. The frame 202 includes six rigid members 204 pivotally connected at joints 205. The members 204 and joints 205 couple polymer deflection in a planar direction 208 into mechanical output in a perpendicular planar direction 210. Bow device 200 is in a resting position as shown in FIG. 4H. Attached to opposite (top and bottom) surfaces of the polymer 206 are electrodes 207 (bottom electrode on bottom side of polymer 206 not shown) to provide electrical communication with polymer 206. FIG. 4I illustrates bow device 200 after actuation.

In the resting position of FIG. 4H, rigid members 204 provide a large stiffness to forces 209 in direction 208, according to their material stiffness. However, for the position of bow device 200 as shown in FIG. 4I, the stiffness in direction 208 is based on the compliance of polymer 202 and any rotational elastic resistance provided by joints 205. Thus, control electronics in electrical communication with electrodes 207 may be used to apply an electrical state that produces deflection for polymer 206 as shown in FIG. 4H, and its corresponding high stiffness, and an electrical state that produces deflection for polymer 206 as shown in FIG. 4I, and its corresponding low stiffness. In this, simple on/off control may be used to provide a large stiffness change using device 200.

In addition to stiffness variation achieved by varying the configuration of rigid members in device 200, stiffness for the position of FIG. 4I may additionally be varied using one of the open or closed loop stiffness techniques described in detail in co-pending U.S. application Ser. No. 10/053,511, filed on Jan. 16, 2002, by Kornbluh, et al and titled "Variable Stiffness Electroactive Polymers, which is incorporated herein in its entirety and for all purposes.

3.2 Multiple Active Areas

In some cases, electrodes cover a limited portion of an electroactive polymer relative to the total area of the polymer. This may be done to prevent electrical breakdown around the edge of a polymer, to allow for polymer portions to facilitate a rolled construction (e.g., an outside polymer barrier layer), to provide multifunctionality, or to achieve customized deflections for one or more portions of the polymer. As the term is used herein, an active area is defined as a portion of a transducer comprising a portion of an electroactive polymer and one or more electrodes that provide or receive electrical energy to or from the portion. The active area may be used for any of the functions described below. For actuation, the active area includes a portion of polymer having sufficient electrostatic force to enable deflection of the portion. For generation or sensing, the active area includes a portion of polymer having sufficient deflection to enable a change in electrostatic energy. A polymer of the present invention may have multiple active areas.

Figure 4J:
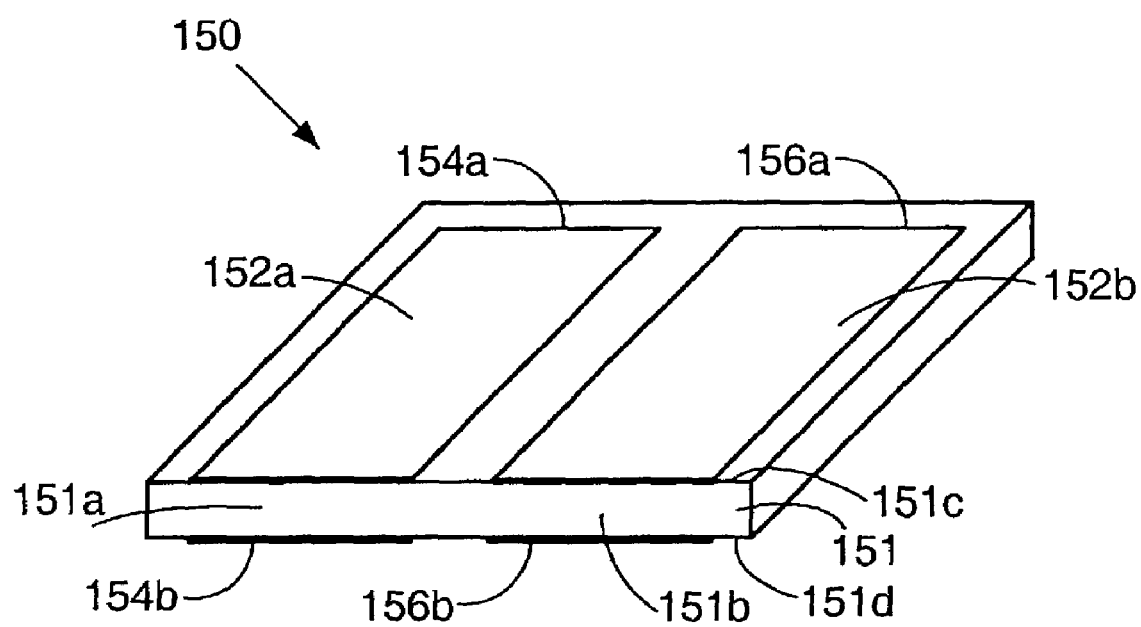
FIG. 4J illustrates a monolithic transducer comprising a plurality of active areas on a single polymer in accordance with one embodiment of the present invention.

In accordance with the present invention, the term "monolithic" is used herein to refer to electroactive polymers and transducers comprising a plurality of active areas on a single polymer. FIG. 4J illustrates a monolithic transducer 150 comprising a plurality of active areas on a single polymer 151 in accordance with one embodiment of the present invention. The monolithic transducer 150 converts between electrical energy and mechanical energy. The monolithic transducer 150 comprises an electroactive polymer 151 having two active areas 152*a* and 152*b*. Polymer 151 may be held in place using, for example, a rigid frame (not shown) attached at the edges of the polymer. Coupled to active areas 152*a* and 152*b* are wires 153 that allow electrical communication between active areas 152*a* and 152*b* and allow electrical communication with communication electronics 155.

Active area 152*a* has top and bottom electrodes 154*a* and 154*b* that are attached to polymer 151 on its top and bottom surfaces 151*c* and 151*d*, respectively. Electrodes 154*a* and 154*b* provide or receive electrical energy across a portion 151*a* of the polymer 151. Portion 151*a* may deflect with a change in electric field provided by the electrodes 154*a* and 154*b*. For actuation, portion 151*a* comprises the polymer 151 between the electrodes 154*a* and 154*b* and any other portions of the polymer 151 having sufficient electrostatic force to enable deflection upon application of voltages using the electrodes 154*a* and 154*b*. When active area 152*a* is used as a generator to convert from electrical energy to mechanical energy, deflection of the portion 151*a* causes a change in electric field in the portion 151*a* that is received as a change in voltage difference by the electrodes 154*a* and 154*b*.

Active area 152*b* has top and bottom electrodes 156*a* and 156*b* that are attached to the polymer 151 on its top and bottom surfaces 151*c* and 151*d*, respectively. Electrodes 156*a* and 156*b* provide or receive electrical energy across a portion 151*b* of the polymer 151. Portion 151*b* may deflect with a change in electric field provided by the electrodes 156*a* and 156*b*. For actuation, portion 151*b* comprises the polymer 151 between the electrodes 156*a* and 156*b* and any other portions of the polymer 151 having sufficient stress induced by the electrostatic force to enable deflection upon application of voltages using the electrodes 156*a* and 156*b*. When active area 152*b* is used as a generator to convert from electrical energy to mechanical energy, deflection of the portion 151*b* causes a change in electric field in the portion 151*b* that is received as a change in voltage difference by the electrodes 156*a* and 156*b*.

Active areas for an electroactive polymer may be easily patterned and configured using conventional electroactive polymer electrode fabrication techniques. Multiple active area polymers and transducers are further described in Ser. No. 09/779,203, which is incorporated herein by reference for all purposes. Given the ability to pattern and independently control multiple active areas allows rolled transducers of the present invention to be employed in many new applications; as well as employed in existing applications in new ways.

Figure 4K:
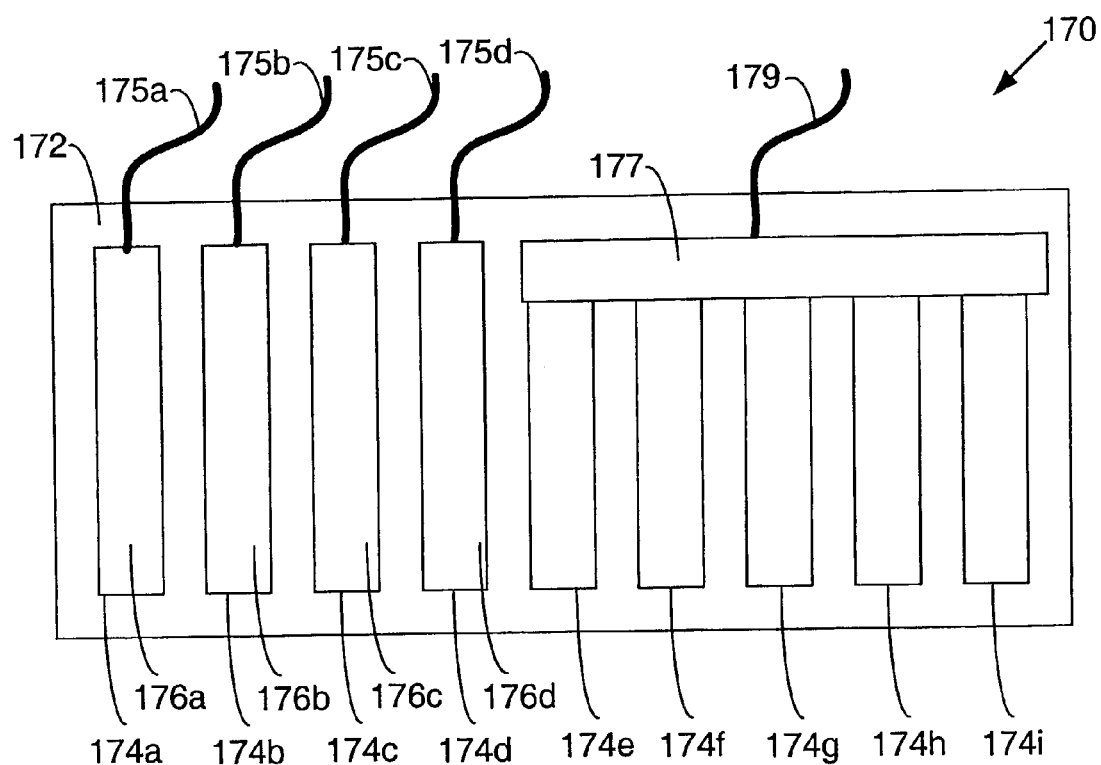
FIG. 4K illustrates a monolithic transducer comprising a plurality of active areas on a single polymer, before rolling, in accordance with one embodiment of the present invention.
Figures 4L, 4M:
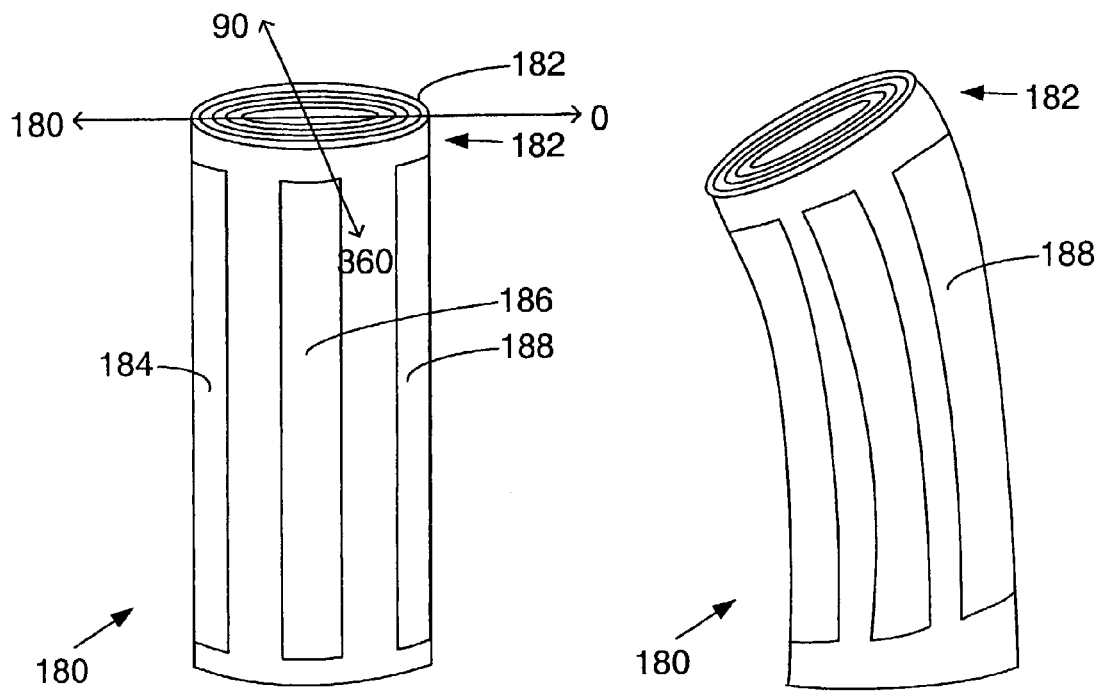
FIG. 4L illustrates a rolled transducer that produces two-dimensional output in accordance with one environment of the present invention.
FIG. 4M illustrates the rolled transducer of FIG. 4L with actuation for one set of radially aligned active areas.

FIG. 4K illustrates a monolithic transducer 170 comprising a plurality of active areas on a single polymer 172, before rolling, in accordance with one embodiment of the present invention. In present invention, the monolithic transducer 170 may be utilized in a rolled or unrolled configuration. Transducer 170 comprises individual electrodes 174 on the facing polymer side 177. The opposite side of polymer 172 (not shown) may include individual electrodes that correspond in location to electrodes 174, or may include a common electrode that spans in area and services multiple or all electrodes 174 and simplifies electrical communication. Active areas 176 then comprise portions of polymer 172 between each individual electrode 174 and the electrode on the opposite side of polymer 172, as determined by the mode of operation of the active area. For actuation for example, active area 176*a* for electrode 174*a* includes a portion of polymer 172 having sufficient electrostatic force to enable deflection of the portion, as described above.

Active areas 176 on transducer 170 may be configured for one or more functions. In one embodiment, all active areas 176 are all configured for actuation. In another embodiment suitable for use with robotic applications, one or two active areas 176 are configured for sensing while the remaining active areas 176 are configured for actuation. In this manner, a rolled electroactive polymer device using transducer 170 is capable of both actuation and sensing. Any active areas designated for sensing may each include dedicated wiring to sensing electronics, as described below.

At shown, electrodes 174*a–d* each include a wire 175*a–d* attached thereto that provides dedicated external electrical communication and permits individual control for each active area 176*a–d*. Electrodes 174*e–i* are all electrical communication with common electrode 177 and wire 179 that provides common electrical communication with active areas 176*e–i*. Common electrode 177 simplifies electrical communication with multiple active areas of a rolled electroactive polymer that are employed to operate in a similar manner. In one embodiment, common electrode 177 comprises aluminum foil disposed on polymer 172 before rolling. In one embodiment, common electrode 177 is a patterned electrode of similar material to that used for electrodes 174*a–i*, e.g., carbon grease.

For example, a set of active areas may be employed for one or more of actuation, generation, sensing, changing the stiffness and/or damping, or a combination thereof. Suitable electrical control also allows a single active area to be used for more than one function. For example, active area 174*a* may be used for actuation and variable stiffness control of a fluid conduit. The same active area may also be used for generation to produce electrical energy based on motion of the fluid conduit. Suitable electronics for each of these functions are described in further detail below. Active area 174b may also be flexibly used for actuation, generation, sensing, changing stiffness, or a combination thereof. Energy generated by one active area may be provided to another active area, if desired by an application. Thus, rolled polymers and transducers of the present invention may include active areas used as an actuator to convert from electrical to mechanical energy, a generator to convert from mechanical to electrical energy, a sensor that detects a parameter, or a variable stiffness and/or damping device that is used to control stiffness and/or damping, or combinations thereof.

In one embodiment, multiple active areas employed for actuation are wired in groups to provide graduated electrical control of force and/or deflection output from a rolled electroactive polymer device. For example, a rolled electroactive polymer transducer many have 50 active areas in which 20 active areas are coupled to one common electrode, 10 active areas to a second common electrode, another 10 active areas to a third common electrode, 5 active areas to a fourth common electrode in the remaining five individually wired. Suitable computer management and on-off control for each common electrode then allows graduated force and deflection control for the rolled transducer using only binary on/off switching. The biological analogy of this system is motor units found in many mammalian muscular control systems. Obviously, any number of active areas and common electrodes may be implemented in this manner to provide a suitable mechanical output or graduated control system.

3.3 Multiple Degree of Freedom Devices

In another embodiment, multiple active areas on an electroactive polymer are disposed such subsets of the active areas radially align after rolling. For example, the multiple the active areas may be disposed such that, after rolling, active areas are disposed every 90 degrees in the roll. These radially aligned electrodes may then be actuated in unity to allow multiple degree of freedom motion for a rolled electroactive polymer device. Similarly, multiple degrees of freedom may be obtained for unrolled electroactive polymer devices, such as those described with respect to FIGS. 4F and 4G. Thus, the rolled polymer devices are one embodiment of multi degrees of freedom that may be obtained with transducer configuration of the present invention.

FIG. 4L illustrates a rolled transducer 180 capable of two-dimensional output in accordance with one environment of the present invention. Transducer 180 comprises an electroactive polymer 182 rolled to provide ten layers. Each layer comprises four radially aligned active areas. The center of each active area is disposed at a 90 degree increment relative to its neighbor. FIG. 4L shows the outermost layer of polymer 182 and radially aligned active areas 184, 186, and 188, which are disposed such that their centers mark 90 degree increments relative to each other. A fourth radially aligned active area (not shown) on the backside of polymer 182 has a center approximately situated 180 degrees from radially aligned active area 186.

Radially aligned active area 184 may include common electrical communication with active areas on inner polymer layers having the same radial alignment. Likewise, the other three radially aligned outer active areas 182, 186, and the back active area not shown, may include common electrical communication with their inner layer counterparts. In one embodiment, transducer 180 comprises four leads that provide common actuation for each of the four radially aligned active area sets.

FIG. 4M illustrates transducer 180 with radially aligned active area 188, and its corresponding radially aligned inner layer active areas, actuated. Actuation of active area 188, and corresponding inner layer active areas, results in axial expansion of transducer 188 on the opposite side of polymer 182. The result is lateral bending of transducer 180, approximately 180 degrees from the center point of active area 188. The effect may also be measured by the deflection of a top portion 189 of transducer 180, which traces a radial arc from the resting position shown in FIG. 4L to his position at shown in FIG. 4M. Varying the amount of electrical energy provided to active area 188, and corresponding inner layer active areas, controls the deflection of the top portion 189 along this arc. Thus, top portion 189 of transducer 180 may have a deflection as shown in FIG. 4L, or greater, or a deflection minimally away from the position shown in FIG. 4L. Similar bending in an another direction may be achieved by actuating any one of the other radially aligned active area sets.

Combining actuation of the radially aligned active area sets produces a two-dimensional space for deflection of top portion 189. For example, radially aligned active area sets 186 and 184 may be actuated simultaneously to produce deflection for the top portion in a 45 degree angle corresponding to the coordinate system shown in FIG. 4L. Decreasing the amount of electrical energy provided to radially aligned active area set 186 and increasing the amount of electrical energy provided to radially aligned active area set 184 moves top portion 189 closer to the zero degree mark. Suitable electrical control then allows top portion 189 to trace a path for any angle from 0 to 360 degrees, or follow variable paths in this two dimensional space.

Transducer 180 is also capable of three-dimensional deflection. Simultaneous actuation of active areas on all four sides of transducer 180 will move top portion 189 upward. In other words, transducer 180 is also a linear actuator capable of axial deflection based on simultaneous actuation of active areas on all sides of transducer 180. Coupling this linear actuation with the differential actuation of radially aligned active areas and their resulting two-dimensional deflection as just described above, results in a three dimensional deflection space for the top portion of transducer 180. Thus, suitable electrical control allows top portion 189 to move both up and down as well as trace two-dimensional paths along this linear axis.

Although transducer 180 is shown for simplicity with four radially aligned active area sets disposed at 90 degree increments, it is understood that transducers of the present invention capable of two- and three-dimensional motion may comprise more complex or alternate designs. For example, eight radially aligned active area sets disposed at 45 degree increments. Alternatively, three radially aligned active area sets disposed at 120 degree increments may be suitable for 2D and 3-D motion.

In addition, although transducer 180 is shown with only one set of axial active areas, the structure of FIG. 4L is modular. In other words, the four radially aligned active area sets disposed at 90 degree increments may occur multiple times in an axial direction. For example, radially aligned active area sets that allow two- and three-dimensional motion may be repeated ten times to provide a wave pattern that may be impressed on a fluid flow.

4. Sensing

Electroactive polymers of the present invention may also be configured as a sensor. Generally, electroactive polymer sensors of this invention detect a "parameter" and/or changes in the parameter. The parameter is usually a physical property of an object such as its temperature, density, strain, deformation, velocity, location, contact, acceleration, vibration, volume, pressure, mass, opacity, concentration, chemical state, conductivity, magnetization, dielectric constant, size, etc. In some cases, the parameter being sensed is associated with a physical "event". The physical event that is detected may be the attainment of a particular value or state of a physical or chemical property. In biological systems, the physical property may be a biological parameter of the system such as a blood sugar level in the human circulation system or a drug concentration.

An electroactive polymer sensor is configured such that a portion of the electroactive polymer deflects in response to the change in a parameter being sensed. The electrical energy state and deflection state of the polymer are related. The change in electrical energy or a change in the electrical impedance of an active area resulting from the deflection may then be detected by sensing electronics in electrical communication with the active area electrodes. This change may comprise a capacitance change of the polymer, a resistance change of the polymer, and/or resistance change of the electrodes, or a combination thereof. Electronic circuits in electrical communication with electrodes detect the electrical property change. If a change in capacitance or resistance of the transducer is being measured for example, one applies electrical energy to electrodes included in the transducer and observes a change in the electrical parameters.

In one embodiment, deflection is input into an active area sensor in some manner via one or more coupling mechanisms. In one embodiment, the changing property or parameter being measured by the sensor corresponds to a changing property of the electroactive polymer, e.g. displacement or size changes in the polymer, and no coupling mechanism is used. Sensing electronics in electrical communication with the electrodes detect change output by the active area. In some cases, a logic device in electrical communication with sensing electronics of sensor quantifies the electrical change to provide a digital or other measure of the changing parameter being sensed. For example, the logic device may be a single chip computer or microprocessor that processes information produced by sensing electronics. Electroactive polymer sensors are further described in Ser. No. 10/007,705, which is incorporated herein by reference for all purposes.

An active area may be configured such that sensing is performed simultaneously with actuation of the active area. For a monolithic transducer, one active area may be responsible for actuation and another for sensing. Alternatively, the same active area of a polymer may be responsible for actuation and sensing. In this case, a low amplitude, high frequency AC (sensing) signal may be superimposed on the driving (actuation) signal. For example, a 1000 Hz sensing signal may be superimposed on a 10 Hz actuation signal. The driving signal will depend on the application, or how fast the actuator is moving, but driving signals in the range from less than 0.1 Hz to about 1 million Hz are suitable for many applications. In one embodiment, the sensing signal is at least about 10 times faster than the motion being measured. Sensing electronics may then detect and measure the high frequency response of the polymer to allow sensor performance that does not interfere with polymer actuation.

Similarly, if impedance changes are detected and measured while the electroactive polymer transducer is being used as a generator, a small, high-frequency AC signal may be superimposed on the lower-frequency generation voltage signal. Filtering techniques may then separate the measurement and power signals.

Active areas of the present invention may also be configured to provide variable stiffness and damping functions. In one embodiment, open loop techniques are used to control stiffness and/or damping of a device employing an electroactive polymer transducer; thereby providing simple designs that deliver a desired stiffness and/or damping performance without sensor feedback. For example, control electronics in electrical communication with electrodes of the transducer may supply a substantially constant charge to the electrodes. Alternately, the control electronics may supply a substantially constant voltage to the electrodes. Systems employing an electroactive polymer transducer offer several techniques for providing stiffness and/or damping control. An exemplary circuit providing stiffness/damping control is provided below.

While not described in detail, it is important to note that active areas and transducers in all the figures and discussions for the present invention may convert between electrical energy and mechanical energy bi-directionally (with suitable electronics). Thus, any of the rolled polymers, active areas, polymer configurations, transducers, and devices described herein may be a transducer for converting mechanical energy to electrical energy (generation, variable stiffness or damping, or sensing) and for converting electrical energy to mechanical energy (actuation, variable stiffness or damping, or sensing). Typically, a generator or sensor active area of the present invention comprises a polymer arranged in a manner that causes a change in electric field in response to deflection of a portion of the polymer. The change in electric field, along with changes in the polymer dimension in the direction of the field, produces a change in voltage, and hence a change in electrical energy.

Often the transducer is employed within a device that comprises other structural and/or functional elements. For example, external mechanical energy may be input into the transducer in some manner via one or more mechanical transmission coupling mechanisms. For example, the transmission mechanism may be designed or configured to receive flow-generated mechanical energy and to transfer a portion of the flow-generated mechanical energy to a portion of a polymer where the transferred portion of the flow generated mechanical energy results in a deflection in the transducer. The flow-generated mechanical energy may produce an inertial force or a direct force where a portion of the inertial force or a portion of the direct force is received by the transmission mechanism.

5. Conditioning Electronics

Devices of the present invention may also rely on conditioning electronics that provide or receive electrical energy from electrodes of an active area for one of the electroactive polymer functions mentioned above. Conditioning electronics in electrical communication with one or more active areas may include functions such as stiffness control, energy dissipation, electrical energy generation, polymer actuation, polymer deflection sensing, control logic, etc.

For actuation, electronic drivers may be connected to the electrodes. The voltage provided to electrodes of an active area will depend upon specifics of an application. In one embodiment, an active area of the present invention is driven electrically by modulating an applied voltage about a DC bias voltage. Modulation about a bias voltage allows for improved sensitivity and linearity of the transducer to the applied voltage. For example, a transducer used in an audio application may be driven by a signal of up to 200 to 100 volts peak to peak on top of a bias voltage ranging from about 750 to 2000 volts DC.

Suitable actuation voltages for electroactive polymers, or portions thereof, may vary based on the material properties of the electroactive polymer, such as the dielectric constant, as well as the dimensions of the polymer, such as the thickness of the polymer film. For example, actuation electric fields used to actuate polymer 12 in FIG. 4A may range in magnitude from about 0 V/m to about 440 MV/m. Actuation electric fields in this range may produce a pressure in the range of about 0 Pa to about 10 MPa. In order for the transducer to produce greater forces, the thickness of the polymer layer may be increased. Actuation voltages for a particular polymer may be reduced by increasing the dielectric constant, decreasing the polymer thickness, and decreasing the modulus of elasticity, for example.

Figure 4N:
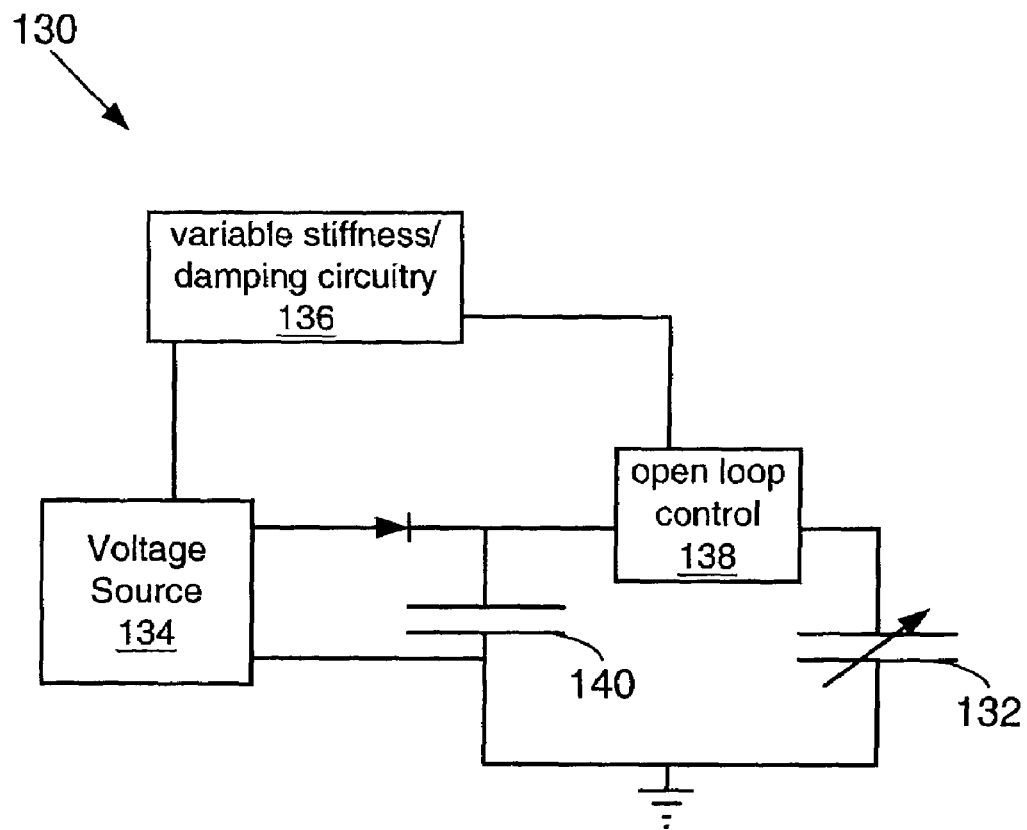
FIG. 4N illustrates an electrical schematic of an open loop variable stiffness/damping system in accordance with one embodiment of the present invention.

FIG. 4N illustrates an electrical schematic of an open loop variable stiffness/damping system in accordance with one embodiment of the present invention. System 130 comprises an electroactive polymer transducer 132, voltage source 134, control electronics comprising variable stiffness/damping circuitry 136 and open loop control 138, and buffer capacitor 140.

Voltage source 134 provides the voltage used in system 130. In this case, voltage source 134 sets the minimum voltage for transducer 132. Adjusting this minimum voltage, together with open loop control 138, adjusts the stiffness provided by transducer 132. Voltage source 134 also supplies charge to system 130. Voltage source 134 may include a commercially available voltage supply, such as a low-voltage battery that supplies a voltage in the range of about 1–15 Volts, and step-up circuitry that raises the voltage of the battery. In this case, voltage step-down performed by step-down circuitry in electrical communication with the electrodes of transducer 132 may be used to adjust an electrical output voltage from transducer 132. Alternately, voltage source 134 may include a variable step-up circuit that can produce a variable high voltage output from the battery. As will be described in further detail below, voltage source 134 may be used to apply a threshold electric field as described below to operate the polymer in a particular stiffness regime.

The desired stiffness or damping for system 130 is controlled by variable stiffness/damping circuitry 136, which sets and changes an electrical state provided by control electronics in system 130 to provide the desired stiffness/damping applied by transducer 132. In this case, stiffness/damping circuitry 36 inputs a desired voltage to voltage source 134 and/or inputs a parameter to open loop control 138. Alternately, if step-up circuitry is used to raise the voltage source 134, circuitry 136 may input a signal to the step-up circuitry to permit voltage control.

As transducer 132 deflects, its changing voltage causes charge to move between transducer 132 and buffer capacitor 140. Thus, externally induced expansion and contraction of transducer 132, e.g., from a vibrating mechanical interface, causes charge to flow back and forth between transducer 132 and buffer capacitor 140 through open loop control 138. The rate and amount of charge moved to or from transducer 132 depends on the properties of buffer capacitor 140, the voltage applied to transducer 132, any additional electrical components in the electrical circuit (such as a resistor used as open loop control 138 to provide damping functionality as current passes there through), the mechanical configuration of transducer 132, and the forces applied to or by transducer 132. In one embodiment, buffer capacitor 140 has a voltage substantially equal to that of transducer 132 for zero displacement of transducer 132, the voltage of system 130 is set by voltage source 134, and open loop control 138 is a wire; resulting in substantially free flow of charge between transducer 132 and buffer capacitor 140 for deflection of transducer 132.

Open loop control 138 provides a passive (no external energy supplied) dynamic response for stiffness applied by transducer 132. Namely, the stiffness provided by transducer 132 may be set by the electrical components included in system 130, such as the control electronics and voltage source 134, or by a signal from control circuitry 136 acting upon one of the electrical components. Either way, the response of transducer 132 is passive to the external mechanical deflections imposed on it. In one embodiment, open loop control 138 is a resistor. One can also set the resistance of the resistor to provide an RC time constant relative to a time of interest, e.g., a period of oscillation in the mechanical system that the transducer is implemented in. In one embodiment, the resistor has a high resistance such that the RC time constant of open loop control 138 and transducer 132 connected in series is long compared to a frequency of interest. In this case, the transducer 132 has a substantially constant charge during the time of interest. A resistance that produces an RC time constant for the resistor and the transducer in the range of about 5 to about 30 times the period of a frequency of interest may be suitable for some applications. For applications including cyclic motion, increasing the RC time constant much greater than the mechanical periods of interest allows the amount of charge on electrodes of transducer 132 to remain substantially constant during one cycle. In cases where the transducer is used for damping, a resistance that produces an RC time constant for the resistor and the transducer in the range of about 0.1 to about 4 times the period of a frequency of interest may be suitable. As one of skill in the art will appreciate, resistances used for the resistor may vary based on application, particularly with respect to the frequency of interest and the size (and therefore capacitance C) of the transducer 132.

In one embodiment of a suitable electrical state used to control stiffness and/or damping using open loop techniques, the control electronics apply a substantially constant charge to electrodes of transducer 132, aside from any electrical imperfections or circuit details that minimally affect current flow. The substantially constant charge results in an increased stiffness for the polymer that resists deflection of transducer 132. One electrical configuration suitable for achieving substantially constant charge is one that has a high RC time constant, as described. When the value of the RC time constant of open loop control 138 and transducer 132 is long compared to the frequency of interest, the charge on the electrodes for transducer 132 is substantially constant. Further description of stiffness and/or damping control is further described in commonly owned patent application Ser. No. 10/053,511, which is described herein for all purposes.

For generation, mechanical energy may be applied to the polymer or active area in a manner that allows electrical energy changes to be removed from electrodes in contact with the polymer. Many methods for applying mechanical energy and removing an electrical energy change from the active area are possible. Rolled devices may be designed that utilize one or more of these methods to receive an electrical energy change. For generation and sensing, the generation and utilization of electrical energy may require conditioning electronics of some type. For instance, at the very least, a minimum amount of circuitry is needed to remove electrical energy from the active area. Further, as another example, circuitry of varying degrees of complexity may be used to increase the efficiency or quantity of electrical generation in a particular active area or to convert an output voltage to a more useful value.

Figure 5A:
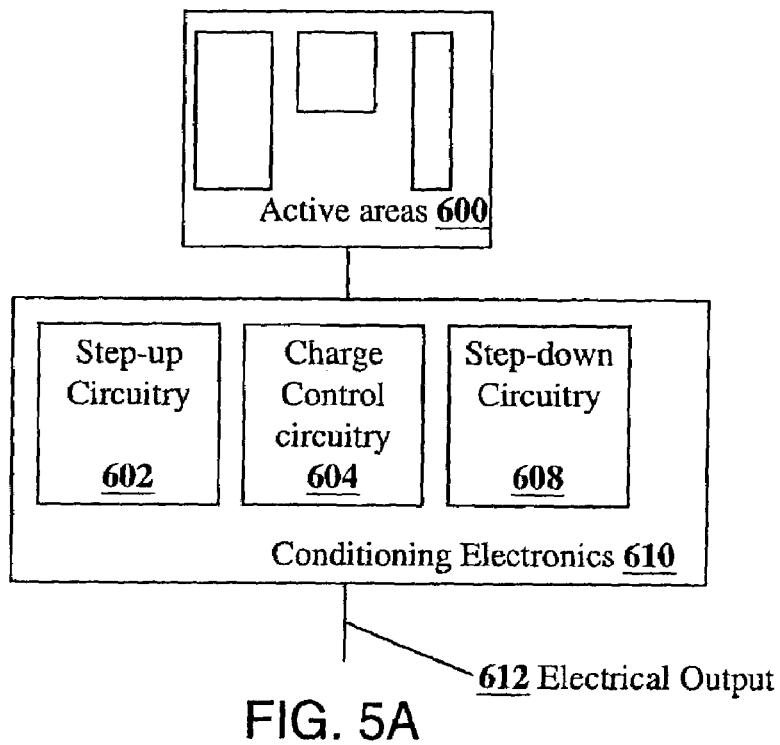
FIG. 5A is block diagram of one or more active areas connected to power conditioning electronics.

FIG. 5A is block diagram of one or more active areas 600 on a transducer that connected to power conditioning electronics 610. Potential functions that may be performed by the power conditioning electronics 610 include but are not limited to 1) voltage step-up performed by step-up circuitry 602, which may be used when applying a voltage to active areas 600, 2) charge control performed by the charge control circuitry 604 which may be used to add or to remove charge from the active areas 600 at certain times, 3) voltage step-down performed by the step-down circuitry 608 which may be used to adjust an electrical output voltage to a transducer. All of these functions may not be required in the conditioning electronics 610. For instance, some transducer devices may not use step-up circuitry 602, other transducer devices may not use step-down circuitry 608, or some transducer devices may not use step-up circuitry and step-down circuitry. Also, some of the circuit functions may be integrated. For instance, one integrated circuit may perform the functions of both the step-up circuitry 602 and the charge control circuitry 608.

Figure 5B:
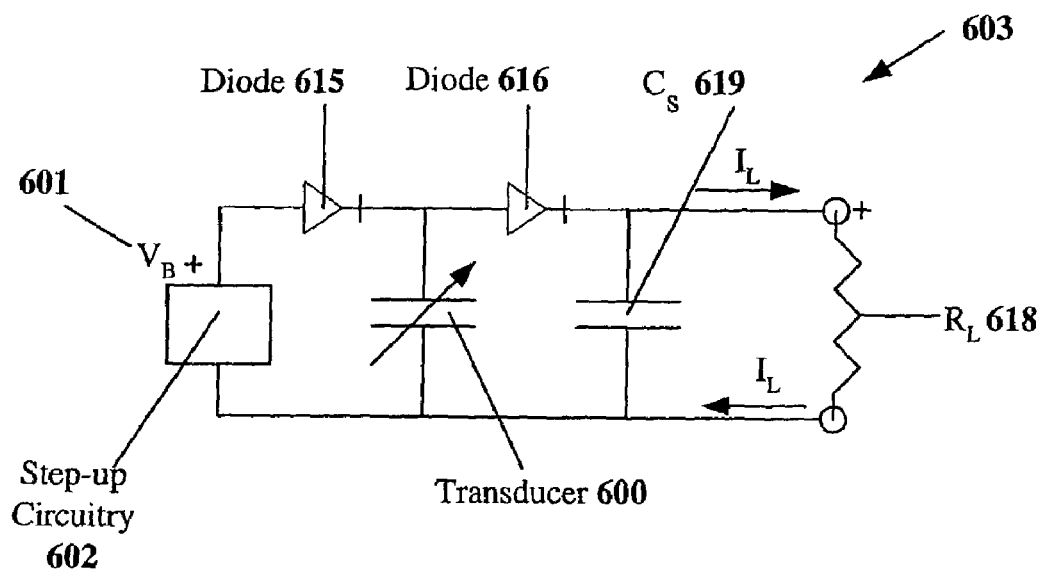
FIG. 5B is a circuit schematic of a device employing a rolled electroactive polymer transducer for one embodiment of the present invention.

FIG. 5B is a circuit schematic of an rolled device 603 employing a transducer 600 for one embodiment of the present invention. As described above, transducers of the present invention may behave electrically as variable capacitors. To understand the operation of the transducer 603, operational parameters of the rolled transducer 603 at two times, $t_1$ and $t_2$ may be compared. Without wishing to be constrained by any particular theory, a number of theoretical relationships regarding the electrical performance the generator 603 are developed. These relationships are not meant in any manner to limit the manner in which the described devices are operated and are provided for illustrative purposes only.

At a first time, $t_1$, rolled transducer 600 may possess a capacitance, $C_1$, and the voltage across the transducer 600 may be voltage 601, $V_B$. The voltage 601, $V_B$, may be provided by the step-up circuitry 602. At a second time $t_2$, later than time $t_1$, the transducer 600 may posses a capacitance $C_2$ which is lower than the capacitance $C_1$. Generally speaking, the higher capacitance C1 occurs when the polymer transducer 600 is stretched in area, and the lower capacitance C2 occurs when the polymer transducer 600 is contracted or relaxed in area. Without wishing to bound by a particular theory, the change in capacitance of a polymer film with electrodes may be estimated by well known formulas relating the capacitance to the film's area, thickness, and dielectric constant.

The decrease in capacitance of the transducer 600 between $t_1$ and $t_2$ will increase the voltage across the transducer 600. The increased voltage may be used to drive current through diode 616. The diode 615 may be used to prevent charge from flowing back into the step-up circuitry at such time. The two diodes, 615 and 616, function as charge control circuitry 604 for transducer 600 which is part of the power conditioning electronics 610 (see FIG. 5A). More complex charge control circuits may be developed depending on the configuration of the generator 603 and the one or more transducers 600 and are not limited to the design in FIG. 5B.

A transducer may also be used as an electroactive polymer sensor to measure a change in a parameter of an object being sensed. Typically, the parameter change induces deflection in the transducer, which is converted to an electrical change output by electrodes attached to the transducer. Many methods for applying mechanical or electrical energy to deflect the polymer are possible. Typically, the sensing of electrical energy from a transducer uses electronics of some type. For instance, a minimum amount of circuitry is needed to detect a change in the electrical state across the electrodes.

Figure 6:
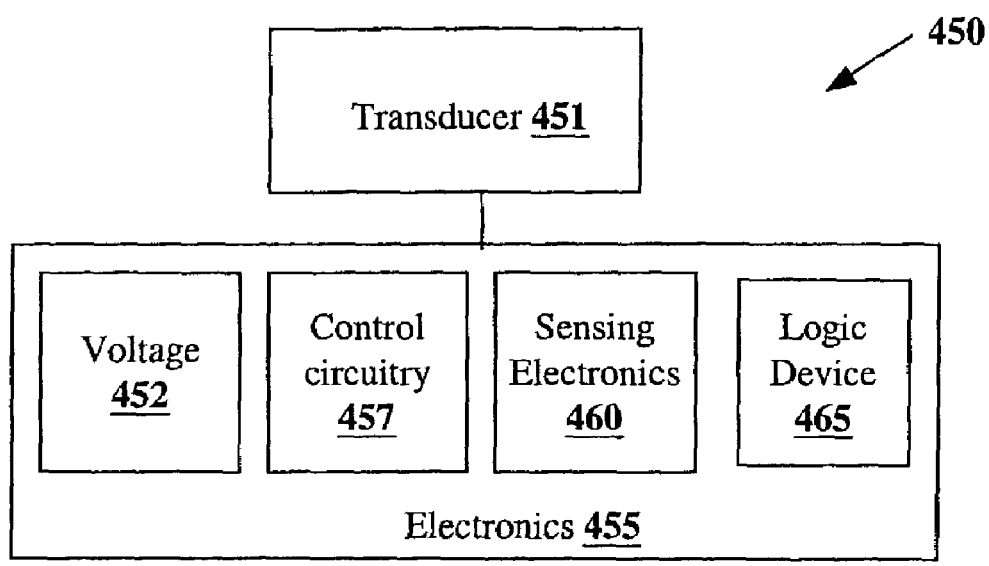
FIG. 6 is a schematic of a sensor employing an electroactive polymer transducer according to one embodiment of the present invention.

FIG. 6 is a schematic of a sensor 450 employing a transducer 451 according to one embodiment of the present invention. As shown in FIG. 6, sensor 450 comprises transducer 451 and various electronics 455 in electrical communication with the electrodes included in the transducer 451. Electronics 455 are designed or configured to add, remove, and/or detect electrical energy from transducer 451. While many of the elements of electronics 455 are described as discrete units, it is understood that some of the circuit functions may be integrated. For instance, one integrated circuit may perform the functions of both the logic device 465 and the charge control circuitry 457.

In one embodiment, the transducer 451 is prepared for sensing by initially applying a voltage between its electrodes. In this case, a voltage, $V_I$, is provided by the voltage 452. Generally, $V_I$ is less than the voltage required to actuate transducer 451. In some embodiments, a low-voltage battery may supply voltage, $V_I$, in the range of about 1–15 Volts. In any particular embodiment, choice of the voltage, $V_I$ may depend on a number of factors such as the polymer dielectric constant, the size of the polymer, the polymer thickness, environmental noise and electromagnetic interference, compatibility with electronic circuits that might use or process the sensor information, etc. The initial charge is placed on transducer 451 using electronics control sub-circuit 457. The electronics control sub-circuit 457 may typically include a logic device such as single chip computer or microcontroller to perform voltage and/or charge control functions on transducer 451. The electronics control sub-circuit 457 is then responsible for altering the voltage provided by voltage 452 to initially apply the relatively low voltage on transducer 451.

Sensing electronics 460 are in electrical communication with the electrodes of transducer 451 and detect the change in electrical energy or characteristics of transducer 451. In addition to detection, sensing electronics 460 may include circuits configured to detect, measure, process, propagate, and/or record the change in electrical energy or characteristics of transducer 451. Electroactive polymer transducers of the present invention may behave electrically in several ways in response to deflection of the electroactive polymer transducer. Correspondingly, numerous simple electrical measurement circuits and systems may be implemented within sensing electronics 460 to detect a change in electrical energy of transducer 451. For example, if transducer 451 operates in capacitance mode, then a simple capacitance bridge may be used to detect changes in transducer 451 capacitance. In another embodiment, a high resistance resistor is disposed in series with transducer 451 and the voltage drop across the high resistance resistor is measured as the transducer 451 deflects. More specifically, changes in transducer 451 voltage induced by deflection of the electroactive polymer are used to drive current across the high resistance resistor. The polarity of the voltage change across resistor then determines the direction of current flow and whether the polymer is expanding or contracting. Resistance sensing techniques may also be used to measure changes in resistance of the polymer included or changes in resistance of the electrodes. Some examples of these techniques are described in commonly owned patent application Ser. No. 10/007,705, which was previously incorporated by reference.

6. Applications

Provided below are several exemplary applications for some of the transducers and devices for performing thermodynamic work on a fluid described above. The exemplary applications described herein are not intended to limit the scope of the present invention. As one skilled in the art will appreciate, transducers of the present invention may find use in countless applications requiring conversion between electrical and mechanical energy.

Figure 7A:
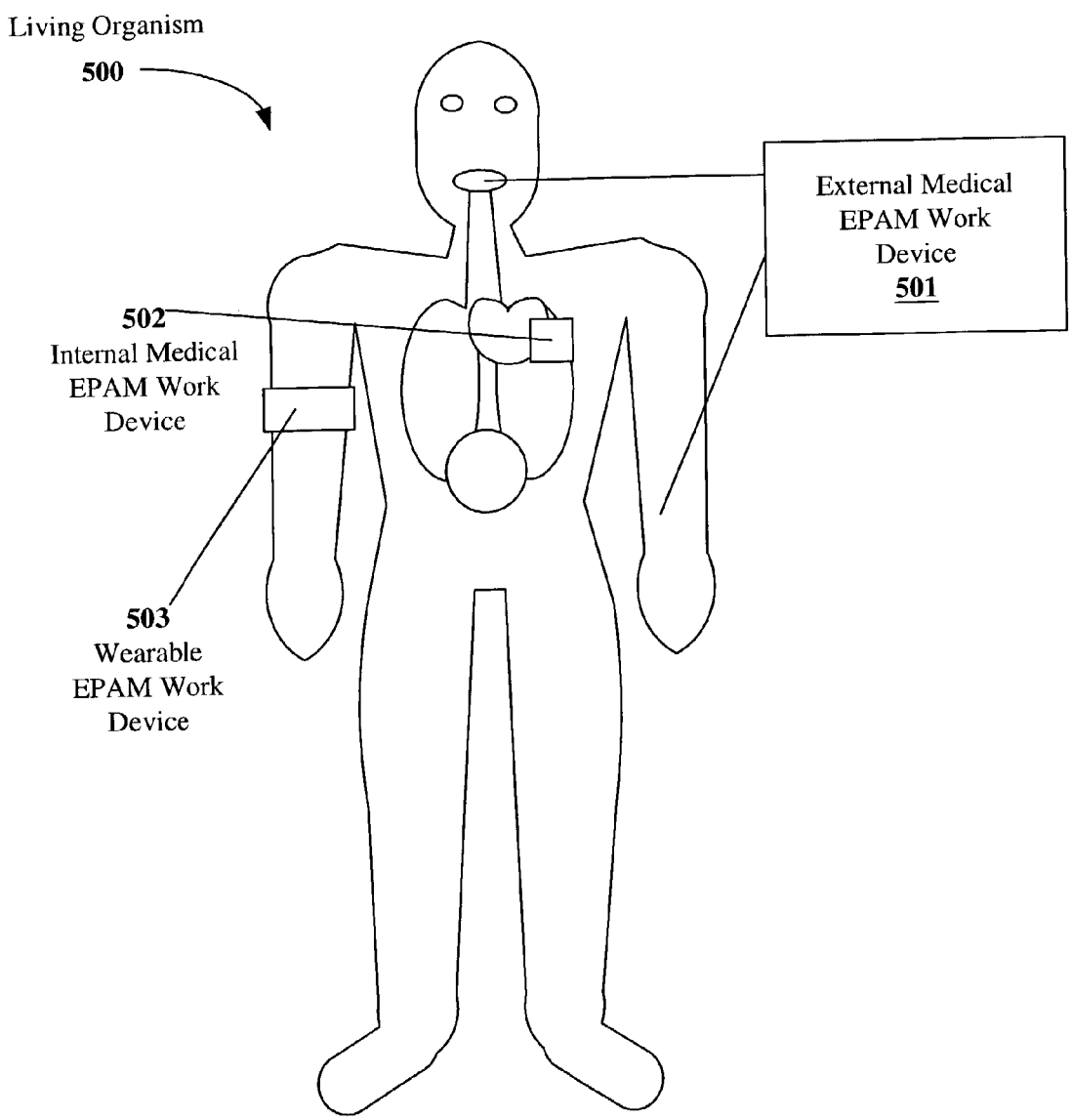
FIG. 7A is a block diagram of a human connected to EPAM devices that perform thermodynamic work on a fluid.

FIG. 7A is a block diagram of a host 500, such as a human or animal, connected to EPAM devices that perform thermodynamic work on a fluid. The EPAM devices of the present invention may be used to provide a driving force to a fluid in medical applications. In general, the EPAM devices may be used to move any fluids used in medical treatment of a host, such as a human or an animal, such as blood, air, drugs in a pharmaceutical composition, lymph, food, spinal fluid, waste fluid (e.g., urine), stomach fluid, etc. In particular, the EPAM devices may be incorporated into medical devices that perform cardiac assistance, such as pumping blood in replace of or in conjunction with a heart. The EPAM device may be used medical devices for providing air to a human body, such as ventilators and pulmonary assist devices to aid people with difficult breathing.

In yet other embodiments, the EPAM device may be used to provide thermodynamic work to fluids as part of 1) a dialysis devices (e.g., pumping the fluids into and out of the body), 2) a plasmaphoresis device (e.g., moving the plasma into and out of the body), 3) a blood pumping device (e.g., pumping blood into the body as part of a transfusion) and 4) a drug delivery device (e.g., pumping a drug from an IV or delivering a drug via a device implanted in the body).

The EPAM devices for performing thermodynamic work may be external to the body 501 (extra-corporal) and connected to the body in some manner. For instance, a dialysis machine or a device for circulating blood during a heart transplant operation that are connected to the body may use EPAM devices of the present invention. The EPAM devices may be located internally in the body. For instance, a medical device 502 for delivering a drug, such as insulin, may be implanted under the skin and use an EPAM device to pump the insulin into the body. In another embodiment, the implanted device 502 may be an artificial heart or a heart assisted device for aiding a damaged or diseased heart. In yet other embodiments, the EPAM devices for performing thermodynamic work on a fluid may be wearable. For instance, a person may wear a device 503, such as EPAM pumping device, for delivering a drug.

In other embodiments, the EPAM devices for performing thermodynamic work may be used in suits or apparatus used in extreme environments. For instance, the EPAM devices may be used to move and control fluids in dive suits, to circulate fluids in biological/chemical protection suits and to circulate fluids in fire protection suits. The circulated fluids may be used for thermal control, such as regulating and cooling body temperature as well as to provide a breathable fluid. The fluids may be circulated within a space defined within the suit or within conduits residing in the materials used for the suits.

Figure 7B:
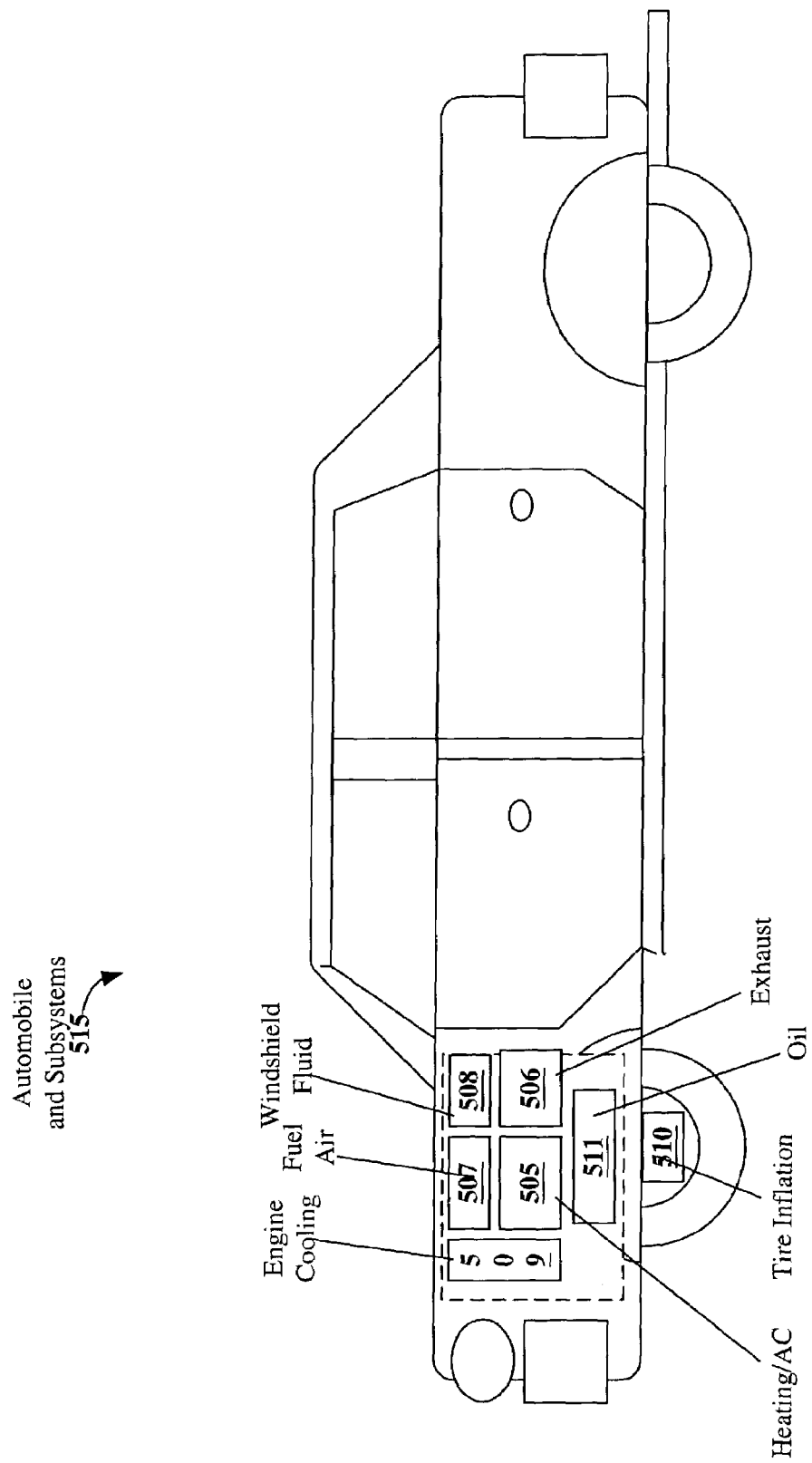
FIG. 7B is a block diagram of automobile and automobile subsystems that employ EPAM devices that perform thermodynamic work on a fluid.

FIG. 7B is a block diagram of automobile and automobile subsystems 515 that employ EPAM devices that perform thermodynamic work on a fluid. In general, the EPAM devices for performing thermodynamic work may be used to perform thermodynamic work on any fluids used in an automotive subsystem. In particular, the EPAM devices may be used in the engine cooling subsystem 509 to pump fluids in internal conduits, such as air or water, that are used to cool the engine. The EPAM devices may be used in cooling fans or devices used to move air externally over engine parts, such as the engine block or the radiator.

In yet other embodiments, the EPAM devices may be used in the windshield fluid system to pump windshield wiper fluid to the windshield. The EPAM devices may be used in the fuel/air system 507 as part of a fuel pump used to bring fuel to the engine or as part of an air pump/compressor system used in the engine. The EPAM devices may be used in the heating/AC system 505 to move heated or cooled air to the passenger compartment, to pump refrigerants or as part of cooling fans for the refrigeration system. The EPAM devices may be used as part of an engine/oil system 511 as a component in an oil pump. The EPAM devices may be used as part of the exhaust/pollution control system 506 to move exhaust gasses through the system.

In a particular embodiment, the EPAM devices may be used as part of the tire system 510 to add compressed air to the tire. The tire pump may be located on each of the tires allowing the tire to self-regulate its own tire pressure. The EPAM tire pump may be connected to sensor(s) that measures the pressure in the tire, road conditions (e.g., dry, wet, icy, etc.) and environmental conditions (e.g., temperature). From the sensor data, the EPAM tire pump 510 may determine the proper tire pressure and adjust the pressure of the tire while the automobile is being driven, at the start of a trip and/or during stops. The tire pump may be connected to a sensor control system in the automobile.

Figure 7C:
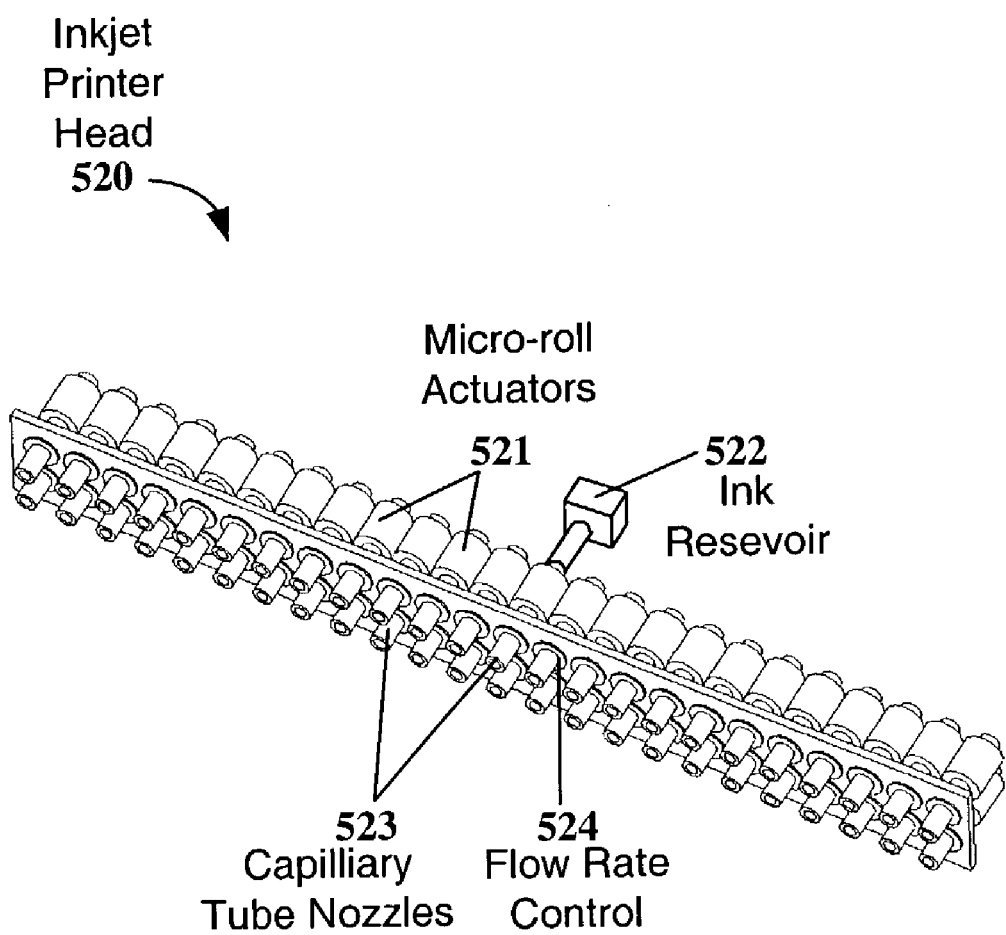
FIG. 7C is a block diagram of an EPAM device for performing thermodynamic work on a fluid in an inkjet printer.

FIG. 7C is a block diagram of an EPAM device for performing thermodynamic work on a fluid in an inkjet printer head 520. The inkjet printer head may include a plurality capillary tube nozzles 523, which may be constructed from the EPAM material. An EPAM valve 524 may be used with each nozzle to control flow into the nozzle 523. An EPAM micro-roll actuator 521 may be used to pump ink for each nozzle from an ink reservoir 522 and to pressurize the ink prior to release from the nozzle 523. Details of EPAM valves and nozzles that may be used with the present invention are described in co-pending U.S. application Ser. No. 10/383,005, filed on Mar. 5, 2003, by Heim, et al., and entitled, "Electroactive Polymer Devices for Controlling Fluid Flow, previously described herein.

In one embodiment, integrated EPAM device may perform the functions of a pump, a valve and a nozzle. The single EPAM element may perform the pressurizing of the fluid (e.g., ink), then may open the valve 524 of the spray nozzle 523 (also called a pintle) at the end or at some timed portion of the stroke of the pump portion of the EPAM device. The pressurized liquid may then be atomized as it flows through the nozzle. This embodiment may be used where precise metering of an atomized spray is needed, such as inkjet head or fuel injectors in an automobile.

7. Conclusion

While this invention has been described in terms of several preferred embodiments, there are alterations, permutations, and equivalents that fall within the scope of this invention which have been omitted for brevity's sake. For example, although the present invention has been described in terms of several specific electrode materials, the present invention is not limited to these materials and in some cases may include air as an electrode. In addition, although the present invention has been described in terms of circular rolled geometries, the present invention is not limited to these geometries and may include rolled devices with square, rectangular, or oval cross sections and profiles. It is therefore intended that the scope of the invention should be determined with reference to the appended claims.

What is claimed is:

1. A device for performing thermodynamic work on a fluid, the device comprising:
   one or more transducers, each transducer comprising at least two electrodes and an electroactive polymer in electrical communication with the at least two electrodes, wherein a portion of the electroactive polymer is arranged to deflect from a first position to a second position in response to a change in electric field, and wherein the electroactive polymer has an elastic modulus below about 100 MPa; and
   at least one surface in contact with a fluid and operatively coupled to the one or more transducers, wherein the deflection of the portion of the electroactive polymer causes the thermodynamic work to be imparted to the fluid and wherein the thermodynamic work is transmitted to the fluid via the at least one surface.

2. The device of claim 1, further comprising:
   a chamber for receiving the fluid wherein a bounding surface of the chamber includes the at least one surface.

3. The device of claim 2, wherein the chamber is formed from one of a bladder or a bellows.

4. The device of claim 3, wherein the deflection of the portion of the electroactive polymer squeezes the bladder or bellows to reduce a volume of the bladder or the bellows.

5. The device of claim 3, wherein the deflection of the portion of the electroactive polymer stretches the bladder or bellows to increase a volume of the bladder or the bellows.

6. The device of claim 3, wherein the chamber is formed from a cylinder and a piston wherein the one surface is a portion of a piston head.

7. The device of claim 2, wherein the deflection of the portion of the electroactive polymer causes a change in a volume of the chamber.

8. The device of claim 7, wherein the change in the volume in the chamber compresses the fluid.

9. The device of claim 7, wherein the change in the volume in the chamber expands the fluid.

10. The device of claim 7, wherein the change in the volume in the chamber causes a thermodynamic phase change in at least a portion of the fluid.

11. The device of claim 7, wherein the change in volume in the chamber draws fluid into the chamber.

12. The device of claim 7, wherein the change in volume in the chamber expels fluid from the chamber.

* * * * *